United States Patent [19]

Nagaoka et al.

[11] Patent Number: 5,981,559
[45] Date of Patent: Nov. 9, 1999

[54] AZOLE DERIVATIVE WITH LEUKOTRIENE (LTS) ANTAGONIZING ACTIVITY AND THROMBOXANE (TX) $A_2$ ANTAGONIZING ACTIVITY

[75] Inventors: Noriko Nagaoka; Masaki Yokota; Hiroaki Akane; Yasuhito Arakida; Yasuo Isomura, all of Ibaraki, Japan

[73] Assignee: Yamanouchi Pharmaceutical Co., Ltd., Tokyo, Japan

[21] Appl. No.: 08/809,466

[22] PCT Filed: Oct. 12, 1995

[86] PCT No.: PCT/JP95/02085

§ 371 Date: Aug. 15, 1997

§ 102(e) Date: Aug. 15, 1997

[87] PCT Pub. No.: WO96/11916

PCT Pub. Date: Apr. 25, 1996

[30] Foreign Application Priority Data

Oct. 14, 1994 [JP] Japan .................................... 6-249488
Oct. 18, 1994 [JP] Japan .................................... 6-251121

[51] Int. Cl.[6] ................ A61K 31/425; A61K 31/44; C07D 277/26; C07D 277/64
[52] U.S. Cl. .................. 514/367; 514/340; 514/342; 514/365; 514/369; 514/374; 514/375; 514/376; 546/269.7; 546/271.4; 546/271.7; 546/370.1; 548/152; 548/171; 548/178; 548/179; 548/181; 548/202; 548/203; 548/204; 548/221; 548/217; 548/229; 548/235
[58] Field of Search ....................... 548/152, 171, 548/178, 179, 181, 202, 203, 204; 546/269.7; 514/365, 367, 342

[56] References Cited

U.S. PATENT DOCUMENTS 5,273,986 12/1993 Holland et al. ..................... 514/365

*Primary Examiner*—Laura L. Stockton
*Attorney, Agent, or Firm*—Sughrue, Mion, Zinn, Macpeak & Seas, PLLC

[57] ABSTRACT

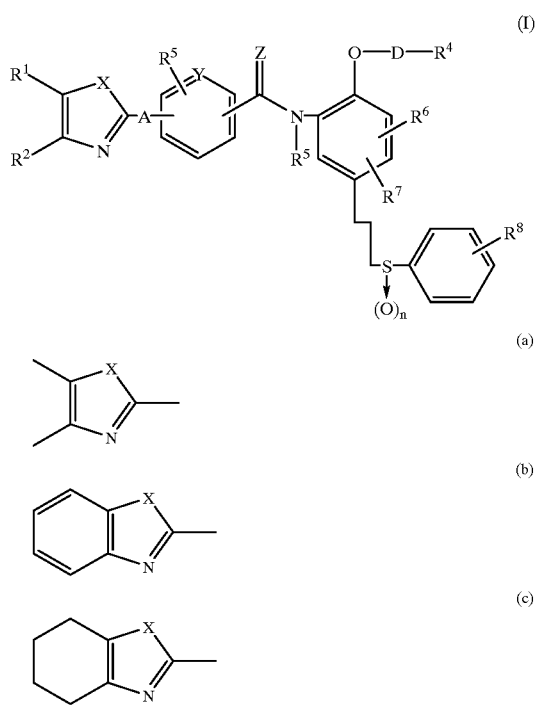

An azole derivative represented by general formula (I) or a pharmaceutically acceptable salt thereof, having both of a leukotriene antagonistic effect and a thromboxane A2 antagonistic effect and being useful in preventing or treating allergic diseases, ischemic heart diseases or ischemic brain diseases, and a medicinal composition containing the same as the active ingredient, wherein $R^1$ and $R^2$ may be the same or different and represent each hydrogen, cycloalkyl, etc., or $R^1$ and $R^2$ together with (a) may form a fused ring (b) or (c) which may be substituted by optionally substituted lower alkyl, amino, etc.; $R^3$, $R^6$, $R^7$, $R^8$ may be the same or different and represent each hydrogen, amino, etc.; $R^4$ represents cyano, tetrazolyl, —$COOR^9$, etc.; $R^5$ represents hydrogen or lower alkyl; D represents optionally substituted lower alkylene; X and Z may be the same or different and represent each oxygen or sulfur; Y represents —N= or —CH=; A represents —O—B—, —B—O—, —S—B—, —B—S— or —B— (B being lower alkylene or lower alkenylene); and n is 0, 1, or 2.

11 Claims, No Drawings

AZOLE DERIVATIVE WITH LEUKOTRIENE (LTS) ANTAGONIZING ACTIVITY AND THROMBOXANE (TX) A₂ ANTAGONIZING ACTIVITY

This application is a 371 of PCT/JP95/02085 filed Oct. 12, 1995.

TECHNICAL FIELD

The present invention relates to a medicament, particularly to a novel azole derivative or a salt thereof which has both leukotriene (LTs) antagonizing activity and thromboxane (TX) A₂ antagonizing activity and is useful as an agent for the prevention or treatment of diseases in which these mediators are concerned, as well as to a pharmaceutical composition comprising said derivative and to an intermediate useful in producing said derivative.

BACKGROUND ART

Various cases are known in relation to asthma, which include dyspeptic asthma, allergic asthma, atopic asthma, bronchial asthma, bacterial asthma, cardiac asthma and the like. Particularly, there are a great number of patients of bronchial asthma among these cases, so that studies have been made on agents or methods for its prevention and treatment. The action mechanism of anti-bronchial asthmatic agents is considered from two viewpoints, i.e. bronchiectasis and anti-inflammation, and many therapeutic and preventive agents has been developed. As the aforementioned bronchodilators, $\beta_2$-stimulators, methylxanthine and cholinolytic agents may be exemplified, and steroids and mediator inhibitors may be exemplified as the anti-inflammatory agents. However, since the current antiasthmatic agents have disadvantages in that the bronchodilators have strong side effects and the anti-inflammatory agents have low efficacy in therapeutic and preventive effects in comparison with other agents, great concern has been directed toward the development of excellent asthma-preventing and treating agents which can supplement both of these disadvantages.

In recent years, among these anti-inflammatory agents, mediator inhibitors such as PAF antagonists, thromboxane A₂ (TXA₂) antagonists/synthesis inhibitors and leukotriene (LTs) antagonists have been applied to asthma and their efficacy is being recognized. However, it has been reported that the therapeutic effect of these agents on asthma (medium or more improvement of the efficacy of agents) is approximately around 50% when used alone (*Igakuno Ayumi* 168 (4), 295 (1994) and *Igakuno Ayumi* 164 (4), 225 (1993)), suggesting that the efficacy is not sufficient because of the difference in the type of mediator which takes the main role in each patient of asthma.

Recently, some compounds capable of inhibiting a plurality of mediators have been reported (for example, an unexamined published Japanese patent application (Kokai) No. 4-154766). However, their effects are not sufficient from the viewpoint of oral absorbability, so that great concern has been directed toward the creation of clinically useful agents which can effect well-balanced inhibition of a plurality of mediators and also are excellent in oral absorbability.

DISCLOSURE OF THE INVENTION

The object of the present invention is to provide a compound which can achieve well-balanced inhibition of two or more mediators (hereinafter, to be referred to as "multiple mediator inhibitor") and a pharmaceutical agent comprising said compound. The inventors of the present invention have conducted extensive studies based on an assumption that a multiple mediator inhibitor could be used as an agent effective for a broad range of allergic diseases such as asthma and the like, and, particularly, excellent effects could be expected as an antiasthmatic agent in the case of an inhibitor having both TXA₂ antagonism and LTs antagonism. As the results, it was found that a derivative represented by the following general formula (I) or a salt thereof, which is characterized in that it has a monocyclic or condensed ring azole ring and which is different from the structures of the known compounds, has the aforementioned two functions in a well-balanced manner and is also possessed of excellent oral absorbability and that it can be an antiasthmatic agent which is broadly useful as a multiple mediator inhibitor, thereby resulting in the accomplishment of the present invention.

Accordingly, the present invention relates to an azole derivative represented by the following general formula (I), a salt thereof and a pharmaceutical composition containing these compounds as an active ingredient, preferably a leukotriene and thromboxane A₂ antagonist.

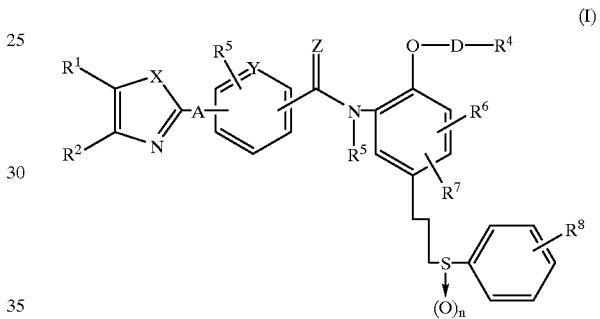

($R^1$ and $R^2$: these may be the same or different from each other and each represents a hydrogen atom, a cycloalkyl group, a lower alkyl group which may be substituted or an aryl group which may be substituted, or $R^1$ and $R^2$ may be combined with a ring

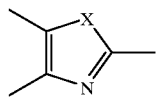

to form a condensed ring represented by a formula

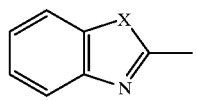

or a formula

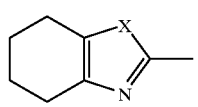

and these condensed rings may be substituted with a lower alkyl group which may be substituted, an amino group, a cyano group, a nitro group, a hydroxyl group, a halogen atom or a lower alkoxy group, $R^3$, $R^6$, $R^7$ and $R^8$: these may be the same or different from one another and each represents a hydrogen atom, an amino group, a cyano group, a nitro group, a hydroxyl group, a halogen atom, a lower alkoxy group or a lower alkyl group which may be substituted, $R^4$: a cyano group, a tetrazolyl group, a group represented by a formula —COOR$^9$ or a group represented by a formula

—E—NH—F—R$^{10}$, $R^9$: a hydrogen atom or an ester residue,

E: a single bond or a carbonyl group,

F: a single bond or a lower alkylene group, $R^{10}$: a hydrogen atom; a carbamoyl group; a mono- or di-lower alkylcarbamoyl group; a carboxyl group; a lower alkoxycarbonyl group; an arylcarbonyl group which may be substituted with a lower alkyl group; a lower alkanoyl group; a lower alkylsulfonyl group; or an arylsulfonyl group which may be substituted with a lower alkyl group, $R^5$: a hydrogen atom or a lower alkyl group, D: a lower alkylene group which may be substituted, X and Z: these may be the same or different from each other and each represents an oxygen atom (O) or a sulfur atom (S), Y: a nitrogen atom (—N═) or a methine group (—CH═), A: a group represented by the following formula —O—B—, —B—O—, —S—B—, —B—S— or —B—, B: a lower alkylene group or a lower alkenylene group, and n: 0, 1 or 2; the same shall apply hereinafter).

Among compounds represented by the aforementioned general formula (I), a preferred compound is a) an azole derivative, a pharmaceutically acceptable salt thereof, a hydrate thereof or a solvate thereof in which $R^4$ is
1) a tetrazolyl group,
2) a group represented by a formula —COOR$^9$ (R9 is a hydrogen atom or an ester residue), or
3) a group represented by the formula —E—NH—F—R$^{10}$ (wherein E is a single bond or a carbonyl group, F is a single bond or a lower alkylene group and R$^{10}$ is a hydrogen atom, a carbamoyl group, a carboxyl or a lower alkoxycarbonyl group, a lower alkanoyl group, a lower alkylsulfonyl group or an arylsulfonyl group which may be substituted with a lower alkyl group), b) an azole derivative, a pharmaceutically acceptable salt thereof, a hydrate thereof or a solvate thereof in which X is a sulfur atom, c) an azole derivative, a pharmaceutically acceptable salt thereof, a hydrate thereof or a solvate thereof in which Y is a methine group (—CH═), or d) an azole derivative, a pharmaceutically acceptable salt thereof, a hydrate thereof or a solvate thereof in which $R^1$ and $R^2$ may be the same or different from each other and each represents a hydrogen atom, a cycloalkyl group, a lower alkyl group, a phenyl group which may be substituted with a lower alkyl group, or $R^1$ and $R^2$ may be combined with a ring

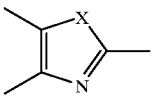

to form a condensed ring represented by a formula

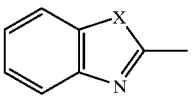

or a formula

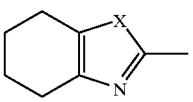

and these condensed rings may be substituted with a lower alkyl group which may be substituted with 1 to 3 halogen atoms, or with an amino group, a cyano group, a nitro group, a hydroxyl group, a halogen atom or a lower alkoxy group, D is a lower alkylene group which may be substituted with a halogen atom, and A is a group represented by a formula —B—O—, a formula —S—B—, a formula —B—S— or a formula —B— (wherein B is a lower alkylene group or a lower alkenylene group).

Particularly preferred compound is an azole derivative, a pharmaceutically acceptable salt thereof, a hydrate thereof or a solvate thereof in which $R^1$ and $R^2$ may be the same or different from each other and each represents a hydrogen atom, a cycloalkyl group, a lower alkyl group or phenyl group which may be substituted with a lower alkyl group, each of $R^3$, $R^6$ and $R^7$ is a hydrogen atom, $R^8$ is a halogen atom, $R^5$ is a hydrogen atom, D is a methylene group, X is a sulfur atom, Y is a methine group (—CH═), Z is an oxygen atom, A is a group represented by the formula —CH$_2$O— and n is 2.

The present invention also relates to a pharmaceutical composition which contains an azole derivative represented by the aforementioned general formula (I), a pharmaceutically acceptable salt thereof, a hydrate thereof or a solvate thereof as an active ingredient, particularly to an agent antagonizing both leukotriene and thromboxane A$_2$.

The present invention also relates to a 2-hydroxyaniline derivative represented by the following general formula (IVc) or a pharmaceutically acceptable salt thereof and a benzoic acid derivative represented by the following general formula (IIIa) or a pharmaceutically acceptable salt thereof, which are useful as production intermediates for compounds represented by the aforementioned general formula (I) or pharmaceutically acceptable salts thereof.

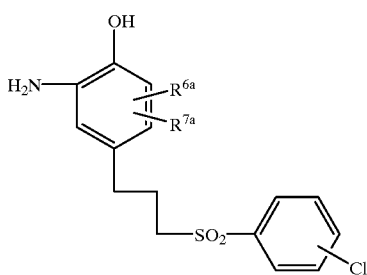

(IVc)

(In the above formula, $R^{6a}$ and $R^{7a}$ may be the same or different from each other and each represents a hydrogen atom or a halogen atom.)

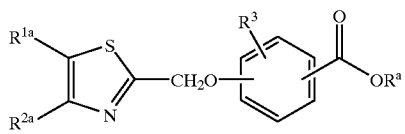

(IIIa)

(In the above formula, $R^{1a}$ and $R^{2a}$ may be the same or different from each other and each represents a hydrogen atom, a cycloalkyl group, a lower alkyl group or a phenyl group which may be substituted with a lower alkyl group, or $R^{1a}$ and $R^{2a}$ may be combined with a ring

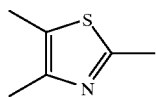

to form a condensed ring represented by a formula

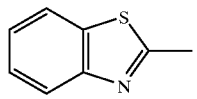

or a formula

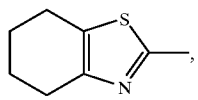

and these condensed rings may be substituted with a lower alkyl group which may be substituted with 1 to 3 halogen atoms, or with an amino group, a cyano group, a nitro group, a halogen atom or a lower alkoxy group, $R^3$ represents a hydrogen atom, an amino group, a cyano group, a nitro group, a hydroxyl group, a halogen atom, a lower alkoxy group or a lower alkyl group, and $R^a$ represents a hydrogen atom or a lower alkyl group.)

The following describes the compound of the present invention further in detail.

In the definition of general formulae of the present invention, the term "lower" means a straight or branched carbon chain having 1 to 6 carbon atoms unless otherwise noted.

In consequence, illustrative examples of the term "lower alkyl group" as used herein include methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methyl propyl and the like. An alkyl group having 1 to 4 carbon atoms are preferable, and a methyl and ethyl groups are more preferable.

The substituent in the term "lower alkyl group which may be substituted" as used herein may be nay general substituents which can be substituted on lower alkyl groups, and its illustrative examples include a halogen atom (for example, chlorine, bromine, fluorine or the like), a hydroxyl group, a lower alkoxy group (for example, methoxy, ethoxy, n-propoxy, i-propoxy or the like), an aryloxy group (for example, naphthyloxy, phenoxy or the like), a aralkyloxy group (for example, benzyloxy, phenetyloxy or the like), a mercapto group, a lower alkylthio group (for example, methylthio, ethylthio or the like), an arylthio group (for example, phenylthio, naphthylthio or the like), an aralkylthio group (for example, benzylthio, phenetylthio or the like), an amino group, a mono- or di-substituted amino group substituted with a lower alkyl group (for example, methylamino, ethylamino, dimethylamino, diethylamino or the like), a lower alkoxycarbonyl group (for example, methoxycarbonyl, ethoxycarbonyl or the like), a lower acyl group (for example, formyl, acetyl, propionyl, benzoyl or the like), an acyloxy group (for example, acetoxy, propionyloxy or the like), a carboxyl group, a carbamoyl group and an aryl group which may be substituted, and from 1 to 5, preferably from 1 to 3 hydrogen atoms of the lower alkyl group may optionally be substituted with these groups.

Illustrative examples of the "cycloalkyl group" are saturated hydrocarbon ring groups having 3 to 8 carbon atoms, such as cyclopropyl, cyclobutyl, cyclopentyl, cyclohexyl, cycloheptyl, cyclooctyl and the like, of which a cycloalkyl group having 3 to 7 carbon atoms is preferred.

The "aryl group" means a hydrocarbon ring aryl group, and its illustrative examples include phenyl, naphthyl and the like.

Examples of the substituent in the "aryl group which may be substituted" include an amino group, a cyano group, a nitro group, a hydroxyl group, a halogen atom, a lower alkoxy group and the aforementioned lower alkyl group which may be substituted.

As the "halogen atom", fluorine, chlorine, bromine and the like may be exemplified.

Examples of the "lower alkoxy group" include methoxy, ethoxy, propoxy, isopropoxy, butoxy, isobutoxy, sec-butoxy, tert-butoxy, pentyloxy (amyloxy), isopentyloxy, tert-pentyloxy, neopentyloxy, 1,2-dimethylpropoxy, 1-ethylpropoxy, hexyloxy and the like.

Examples of the "ester residue" include ester residues such as a lower alkyl, an aralkyl (benzyl, phenetyl, 1-naphthylmethyl or the like) and the like, or ester residues which are hydrolyzed by metabolism in the living body, such as a lower alkanoyloxy-lower alkyl group (acetyloxymethyl, acetyloxyethyl, tert-butanoyloxymethyl or the like), a lower alkenoyl-lower alkyl group (vinylcarbonylmethyl, vinylcarbonylethyl or the like), a cycloalkylcarbonyloxy-lower alkyl group (cyclopropylcarbonyloxymethyl, cyclobutylcarbonyloxy, cyclopentylcarbonyloxymethyl or the like), a lower alkenoyloxy-lower alkyl group (vinylcarbonyloxymethyl, vinylcarbonyloxyethyl or the like), a lower alkoxy-lower alkyl group (methoxymethyl, methoxyethyl, ethoxymethyl or the like), a lower alkoxy-lower alkoxy-lower alkyl group (methoxymethoxymethyl or the like), a lower alkoxycarbonyloxy-lower alkyl group (methoxycarbonyloxymethyl, ethoxycarbonylmethyl, tert-butoxycarbonyloxymethyl or the like), a benzoyloxy-lower alkyl group (benzoyloxymethyl, benzoyloxyethyl or the like), 2-oxotetrahydrofuran-5-yl group, a 2-oxo-5-lower alkyl-1,3-dioxolen-4-ylmethyl group

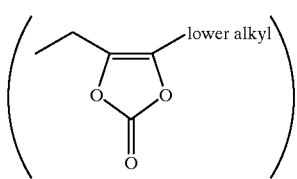

("lower alkyl group" in this formula is preferably methyl, ethyl, propyl, isopropyl, butyl or the like), tetrahydrofuranylcarbonyloxymethyl group, phthalidyl group and the like.

Preferred of these groups are lower alkyl, aralkyl, lower alkanoyloxy-lower alkyl, phthalidyl, 2-oxo-5-lower alkyl-1,3-dioxolen-4-ylmethyl and lower alkoxycarbonyloxy-lower alkyl groups. Particularly preferred are lower alkyl groups such as methyl, ethyl, propyl, isopropyl, butyl and the like.

The "lower alkylene group" is an alkylene group having 1 to 6 carbon atoms, and its illustrative examples include methylene, ethylene, methylmethylene

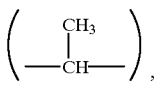

trimethylene, propylene

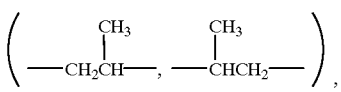

dimethylmethylene

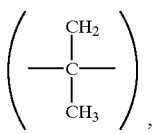

tetramethylene, 1-methyltrimethylene, 2-methyltrimethylene, 3-methyltrimethylene, 1-ethylethylene

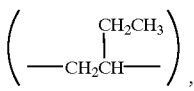

2-ethylethylene

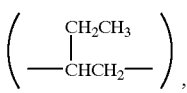

2,2-dimethylethylene

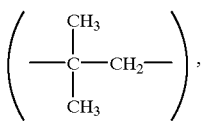

1,1-dimethylethylene

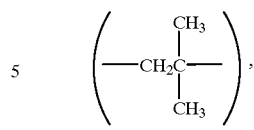

ethylmethylmethylene

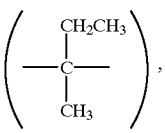

pentamethylene, 1-methyltetramethylene, 2-methyltetramethylene, 3-methyltetramethylene, 4-methyltetramethylene, 1,1-dimethyltrimethylene, 2,2-dimethyltrimethylene, 3,3-dimethyltrimethylene, 1,3-dimethyltrimethylene, 2,3-dimethyltrimethylene, 1,2-dimethyltrimethylene, 1,1,2-trimethylethylene, diethylmethylene, hexamethylene, 1-methylpenta- methylene, 1,1-dimethyltetramethylene, 2,2-dimethyltetramethylene and the like. Alkylene groups having 1 to 3 carbon atoms such as methylene, ethylene, propylene, methylmethylene and dimethylmethylene are preferred and a methylene group is more preferred.

The "mono- or di-lower alkylcarbamoyl group" in $R^{10}$ means a group in which 1 or 2 hydrogen atoms of the carbamoyl group are substituted with the aforementioned lower alkyl group, and its preferred examples are mono- or di-$C_{1-4}$ alkylcarbamoyl groups such as methylcarbamoyl, ethylcarbamoyl, propylcarbamoyl, isopropylcarbamoyl, dimethylcarbamoyl and diethylcarbamoyl.

The "lower alkoxycarbonyl group" means a group in which the aforementioned lower alkoxy group is linked to the carbonyl group, such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl, tert-pentyloxycarbonyl and hexyloxycarbonyl.

The arylcarbonyl group of the "arylcarbonyl group which may be substituted with a lower alkyl group" means a hydrocarbon ring arylcarbonyl group, and its illustrative examples include benzoyl and naphthoyl.

These arylcarbonyl groups may be substituted with the aforementioned lower alkyl group and, in that case, they may be substituted preferably with an alkyl group having 1 to 3 carbon atoms, resulting in 2-methylbenzoyl, 3-methylbenzoyl, 4-methylbenzoyl, 2-ethylbenzoyl, 3-ethylbenzoyl, 4-ethylbenzoyl, 1-naphthoyl, 2-naphthoyl and the like.

Examples of the "lower alkanoyl group" include formyl, acetyl, propionyl, butylyl, isobutylyl, valeryl, isovaleryl, pivaloyl and the like. Preferred of these are formyl, acetyl and propionyl groups.

The "lower alkylsulfonyl group" means a group in which the sulfonyl group is linked to the aforementioned lower alkyl group, and its illustrative examples include methylsulfonyl, ethylsulfonyl, propylsulfonyl, isopropylsulfonyl, butylsulfonyl, pentylsulfonyl, hexylsulfonyl and the like. Preferred is an alkylsulfonyl group having 1 to 3 carbon atoms.

The arylsulfonyl group of the "arylsulfonyl group which may be substituted with a lower alkyl group" means a hydrocarbon ring arylsulfonyl group, and its illustrative examples include phenylsulfonyl and naphthylsulfonyl. These arylsulfonyl groups may be substituted with the aforementioned lower alkyl group. In that case, they may be substituted preferably with an alkyl group having 1 to 3 carbon atoms, thus resulting for example in 2-methylphenylsulfonyl, 3-methylphenylsulfonyl, 4-methylphenylsulfonyl, 2-ethylphenylsulfonyl, 3-ethylphenylsulfonyl, 4-ethylphenylsulfonyl, 2-propylphenylsulfonyl, 3-propylphenylsulfonyl and 4-propylphenylsulfonyl.

The lower alkylene group of the "lower alkylene group which may be substituted" in D is as defined in the foregoing, and examples of its substituent include a halogen atom, a hydroxyl group and a lower alkoxy group.

The "lower alkylene group" in B is as defined in the foregoing, and examples of the "lower alkenylene group" in B include vinylene, propenylene (—CH$_2$—CH=CH—, —CH=CH—CH$_2$—), butenylene (—CH$_2$—CH$_2$—CH=CH—, —CH$_2$—CH=CH—CH$_2$—, —CH=CH—CH$_2$—CH$_2$—) and the like. Preferred of these is vinylene group.

The compound of the present invention represented by the general formula (I) forms a salt. Salts of the compound (I) are included in the present invention, and illustrative examples of the salts include acid addition salts with inorganic acids such as hydrochloric acid, hydrobromic acid, hydroiodic acid, sulfuric acid, nitric acid, phosphoric acid and the like and organic acids such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid and the like, as well as acidic amino acids such as aspartic acid, glutamic acid and the like.

Examples of its base salts include inorganic base salts such as with sodium, potassium, magnesium, calcium, aluminum and the like and organic base salts such as with methylamine, ethylamine, ethanolamine and basic amino acids (e.g., lysin, arginine, ornithine and the like), as well as ammonium salt.

Also, the compound (I) of the present invention may have asymmetric carbon atom, double bond and the like in some cases depending on the type of substituents, so that the compound may exist in the form of stereoisomers such as optical isomers, geometrical isomers and the like based on their presence.

In consequence, these stereoisomers either in the isolated form or as a mixture are included in the present invention.

In addition, hydrates, various solvates and crystal polymorphism of the compound (I) are also included in the present invention.

The compound of the present invention can be synthesized, for example, by the following methods.

Production Method 1

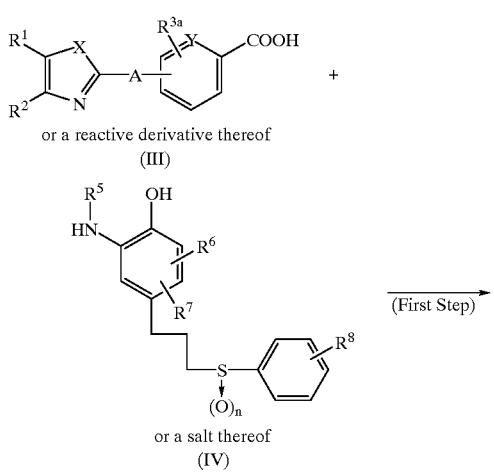

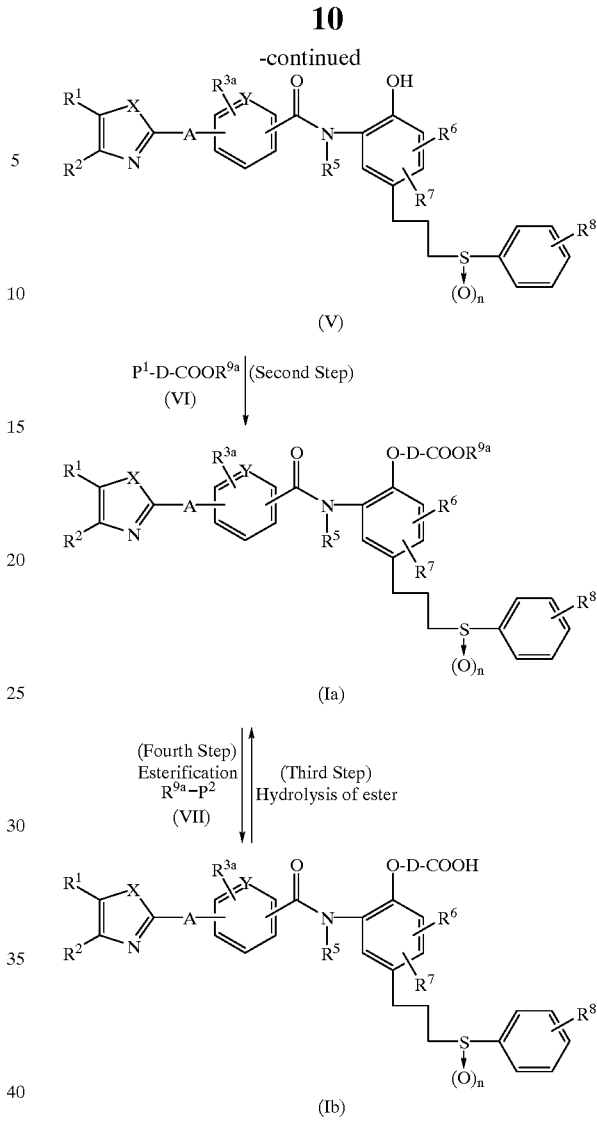

(In the above formulae, $P^1$ is a halogen atom or an organic sulfonate residue, $P^2$ is a hydroxyl group, a halogen atom or an organic sulfonate residue, $R^{3a}$ is a hydrogen atom, a halogen atom, a lower alkoxy group, a lower alkyl group which may be substituted, a cyano group, a nitro group, a protected hydroxyl group or a protected amino group and $R^{9a}$ is an ester residue. The same shall apply hereinafter.)

In the first step of the method 1, a carboxylic acid represented by the general formula (III) or a reactive derivative thereof and an amine represented by the general formula (IV) or a salt thereof are subjected to amidation in the usual way to give a compound represented by the general formula (V).

In this connection, examples of the protecting group of the amino group represented by $R^{3a}$ include p-nitrobenzyl, benzyl, benzhydrile, p-nitrobenzyloxycarbonyl and the like. Also, examples of the protecting group for the hydroxyl group include an arylmethoxy group such as benzyloxy or the like, an acyloxy group such as benzoyloxy, a lower alkanoyloxy or the like and a trialkylsilyl group.

Examples of the reactive derivative of the compound (III) include acid halides such as acid chloride and acid bromide; acid azide; active esters with 1-hydroxybenzotriazole, N-hydroxysuccinimide and the like; symmetric acid anhydride; and mixed anhydrides with alkylcarbonic acid, p-toluenesulfonic acid and the like.

When the compound (III) is reacted as a free carboxylic acid, it is advantageous to carry out the reaction in the presence of a condensing agent such as dicyclohexylcarbodiimide (DCC), 1-ethyl-3-(3'-dimethylaminopropyl) carbodiimide, 1,1'-carbonyldiimidazole or the like.

The reaction is carried out using the compound (III) or a reactive derivative thereof and the compound (IV) at almost equimolar ratio or by increasing one of them to an excess amount, in an organic solvent which is inert to the reaction such as pyridine, tetrahydrofuran, dioxane, ether, benzene, toluene, xylene, dichloromethane, dichloroethane, chloroform, dimethylformamide (DMF), ethyl acetate, acetonitrile or the like.

Depending on the type of the reactive derivative, it is advantageous in some cases to add a base such as triethylamine, pyridine, picoline, lutidine, N,N-dimethylaniline, potassium carbonate, sodium hydroxide or the like, from the viewpoint of smoothly carrying out the reaction. Pyridine can be used also as the solvent.

Also, depending on the type of solvent, e.g., when a high porality solvent such as DMF or the like is used, the reaction can be carried out smoothly by adding equal or larger amount of N-hydroxysuccinimide or N-hydroxybenzotriazole to the reaction solution in advance.

The reaction temperature varies depending on the type of the reactive derivative and is optionally decided.

In the second step, the compound (Ia) of the present invention is obtained by subjecting the amide compound (V) obtained in the first step to etherification with a halogenated alkyl compound or the like represented by the general formula (VI) in the usual way.

The etherification is carried out by subjecting the compound (V) and a halide (or a sulfonate) (VI) to substitution reaction in the presence of a base.

In this connection, examples of the halogen atom represented by $P^1$ or $P^2$ include iodine, bromine, chlorine, fluorine and the like, and examples of the organic sulfonate residue include alkylsulfonyloxy groups (e.g., methanesulfonyloxy, ethanesulfonyloxy and the like) and arylsulfonyloxy groups (e.g., benzenesulfonyloxy, toluene(especially p-toluene) sulfonyloxy and the like).

When a halide is used as the compound (VI), it is advantageous to carried out the reaction using the compound (V) and the compound (VI) at almost equimolar ratio or by increasing one of them to an excess amount, at room temperature to a heating temperature or at a heat refluxing temperature, in an organic solvent which is inert to the reaction such as N,N-dimethylformamide, dimethyl sulfoxide, acetone, methyl ethyl ketone, methanol, ethanol, isopropanol, dichloromethane, dichloroethane, chloroform, ether, tetrahydrofuran, dioxane or the like or water or a mixed solvent thereof.

In some cases, the reaction can be carried out smoothly by the addition of a secondary or tertiary base such as pyridine, picoline, N,N-dimethylaniline, N-methylmorpholine, trimethylamine, triethylamine, dimethylamine or the like or an inorganic base such as sodium hydride, sodium hydroxide, potassium hydroxide, n-butyl lithium, potassium-t-butoxide, potassium carbonate, sodium carbonate, sodium bicarbonate or the like.

When a sulfonate is used as the compound (VI), it is desirable to carry out the reaction in the solvents inert to the reaction as described above, in the same amounts described above and at a cooling to room temperature.

In the third step, the compound (Ib) of the present invention is obtained by hydrolyzing the ester moiety of the compound (Ia) of the present invention obtained in the second step.

A usual method in which hydrolysis is carried out in the presence of a base such as sodium carbonate, sodium hydroxide or the like or an acid such as trifluoroacetic acid, hydrochloric acid or the like can be employed in this reaction, and it is desirable to carry out the reaction under a temperature condition of from room temperature to 100° C.

In the fourth step, the compound (Ia) of the present invention is produced by the esterification of the compound (Ib) of the present invention which is a carboxylic acid. This step is carried out by the usual esterification method using esterification agent such as an alcohol or a halide thereof, a sulfate, a diazo compound or the like, which can be easily understood by those skilled in the art, including the necessity of protection, deprotection, hydrolysis, reduction and the like.

In addition, a sulfinyl or sulfonyl compound as a member of the compound of the present invention can be produced by oxidizing corresponding sulfide or sulfinyl compound in the usual way.

Production Method 2

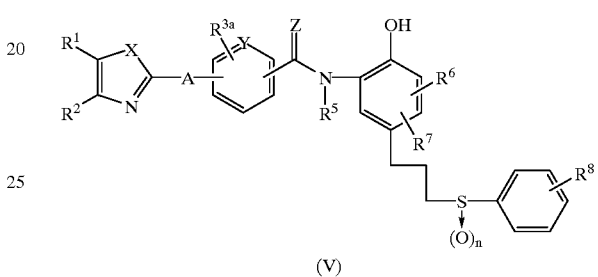

(V)

i) $P^1$-D-CN (VIII)
ii) $R_3SnN_3$ or $NaN_3$(IX)

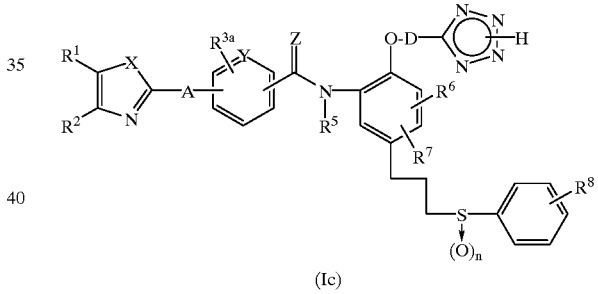

(Ic)

(In the above formulae, R is a lower alkyl group or an aryl group. The same shall apply hereinafter.)

In the production method 2, the compound (Ic) of the present invention is produced by allowing the compound represented by the general formula (V) to react i) with a cyano compound represented by (VIII) and then ii) with a trialkyltin azide, triaryltin azide or sodium azide represented by the general formula (IX).

When the cyano compound of i) is used, the reaction-inert organic solvents described in the first step of the production method 1 may be used under the same reaction conditions.

With regard to the reaction of ii), the synthesis can be effected by carrying out the reaction at room temperature to reflux condition for several days to several hours in an inert solvent such as benzene, toluene or the like in the presence of a trialkyl tin or a triaryl tin. The synthesis can also be effected by carrying out several hours to several days of stirring at room temperature to reflux condition in dimethylformamide in the presence of sodium azide and ammonium chloride.

Production Method 3

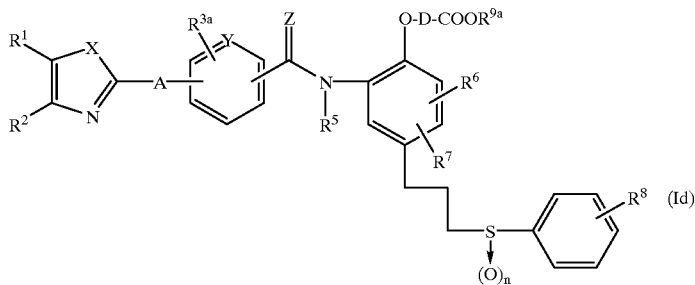

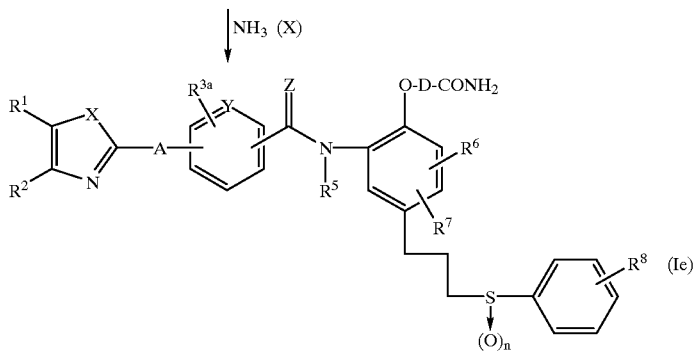

In the production method 3, the compound (Ie) of the present invention is produced by allowing the compound (Id) of the present invention to react with ammonia (X).

The compound (Ie) of the present invention is produced by carrying out the reaction using the compound (Id) and the compound (X) at equimolar ratio or by increasing one of them to an excess amount, at ice-cooled or room temperature to ice-cooled or heat refluxing temperature in an organic solvent inert to the reaction, such as methanol, ethanol, tetrahydrofuran, ether, dioxane, 2-propanol, benzene, toluene, xylene, N,N-dimethylformamide, dimethyl sulfoxide, dichloromethane, chloroform, pyridine or the like or water or a mixed solvent thereof.

Alternatively, the compound (Ie) of the present invention can be synthesized from the compound (Ib) by the general amidation reaction described in the first step of the production method 1 or from the compound (V) and a compound of formula $P^1$—D—$CONH_2$ (wherein $P^1$ is a halogen atom (chlorine, bromine or iodine) or an organic sulfonate residue) in the same manner as the case of the second step of the production method 1.

Production Method 4

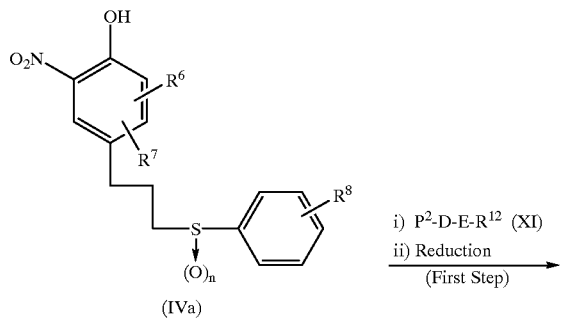

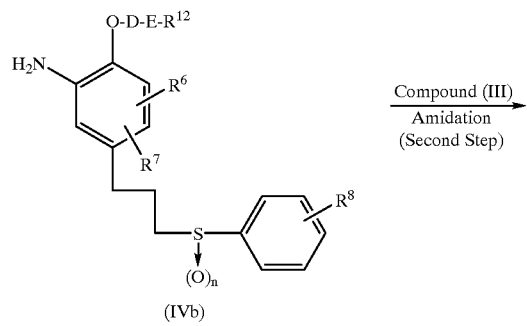

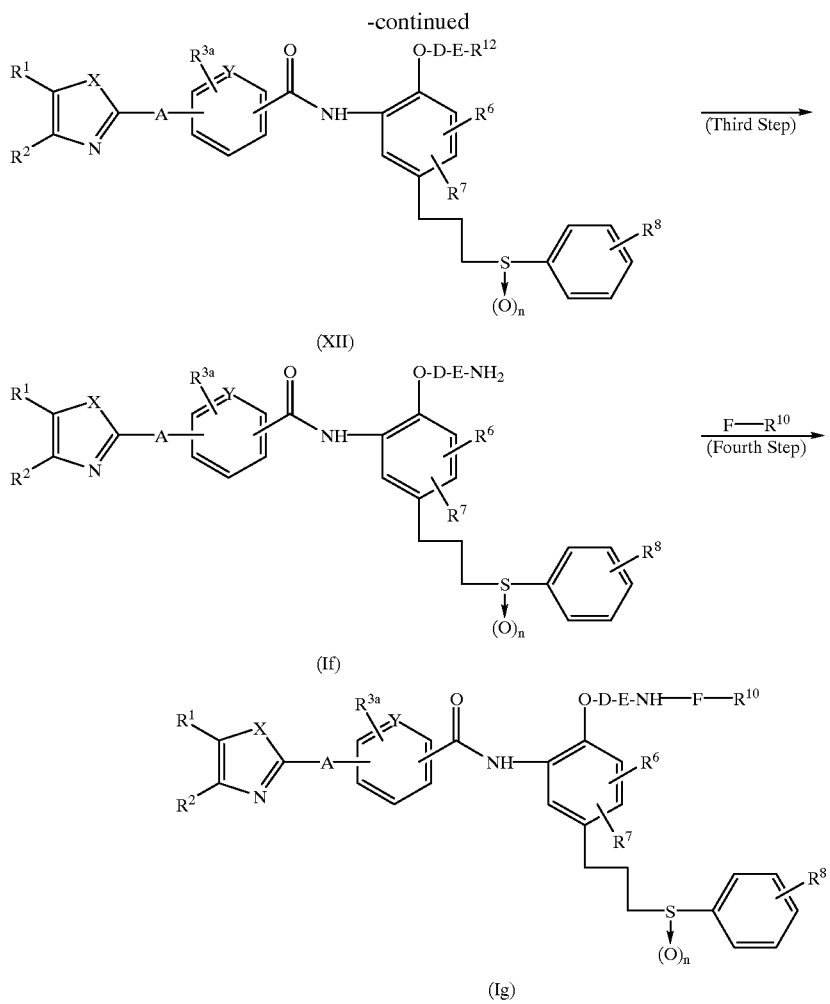

(In the above formulae, $R^{12}$ is a group from which an amino group can be derived. The same shall apply hereinafter.)

In the production method 4, the compounds (If) and (Ig) of the present invention are obtained by subjecting an amine or a salt thereof (IVb) which is obtained by the etherification of a phenol derivative represented by the general formula (IVa) and the subsequent reduction to amidation with the compound (III), followed by conversion into an amino group, N-alkylation, N-acylation and N-alkylsulfonylation.

In the first step, the amine derivative represented by the general formula (IVb) is obtained by i) subjecting the phenol derivative represented-by the general formula (IVa) to etherification with the compound (XI) and then ii) reducing the nitro group.

In this connection, a phthalimide group and the like may be exemplified as the group represented by $R^{12}$ from which an amino group can be derived.

The etherification of i) can be carried out in the same manner as the case of the second step of the production method 1 when $P^2$ is a halogen atom or an organic sulfonate residue.

When $P^2$ is a hydroxyl group, the reaction may be carried out at a temperature of from ice-cooled temperature to heat refluxing temperature in a solvent such as tetrahydrofuran (THF), diethyl ether, dioxane, benzene, toluene, xylene, N,N-dimethylformamide, acetonitrile, ethyl acetate or the like in the presence of a phosphorus compound represented by a formula $R_3P$ and a compound represented by $R^{13}OCO-N=N-COOR^{13}$ (wherein R is a lower alkyl group or an aryl group and $R^{13}$ is a lower alkyl group).

The reduction of a nitro group of ii) can be carried out in the usual way.

In the second step, the compound (XII) is obtained by the amidation of the amine compound (IVb) with the aforementioned compound (III), which can be carried out in the same manner as the case of the first step of the production method 1.

In the third step, the compound (If) of the present invention is obtained by allowing the compound (XII) to react with hydrazine, phenylhydrazine, a lower alkylamine compound or the like, thereby an amino group is derived from a amino group-derivable group. This reaction may be carried out using the compound (XII) and hydrazine, phenylhydrazine, a lower alkylamine or the like at equimolar ratio or using one of them in a slightly excess amount, at a temperature of from ice-cooled temperature to refluxing temperature in an organic solvent inert to the reaction, such as methanol, ethanol, 2-propanol, tetrahydrofuran (THF), dioxane, ether, N,N-dimethylformamide, benzene, toluene, xylene or the like.

In the fourth step, the compound (Ig) of the present invention is produced by subjecting the compound (If) to usual N-alkylation, acylation or sulfonylation. This step may be applied to the aforementioned compound (Ie).

Production Method 5

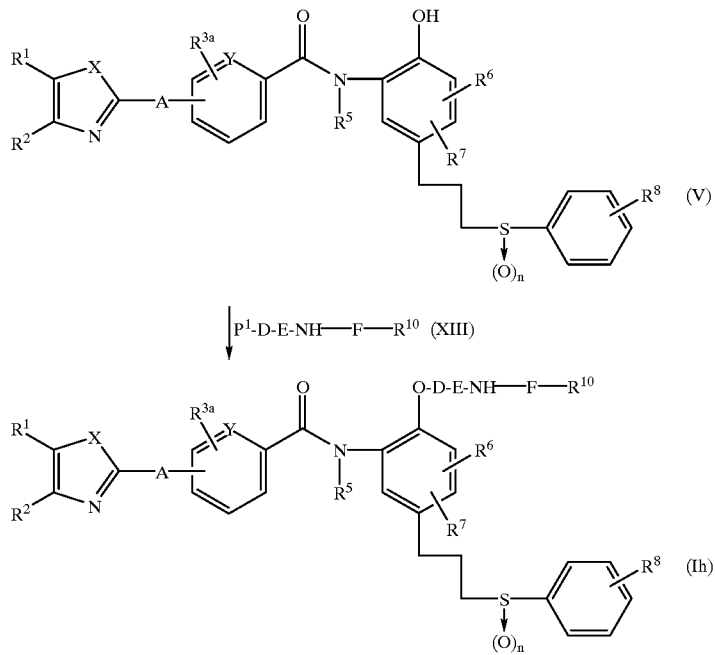

In the production method 5, the compound (Ih) of the present invention is obtained by allowing the compound (V) to react with a compound (XIII).

The reaction of this production method can be carried out in the same manner as in the case of the second step of the production method 1.

Alternatively, the compound (Ih) of the present invention can be synthesized from the compound (Ib) of the present invention by the general amidation reaction of the first step of the production method 1.

Production Method 6

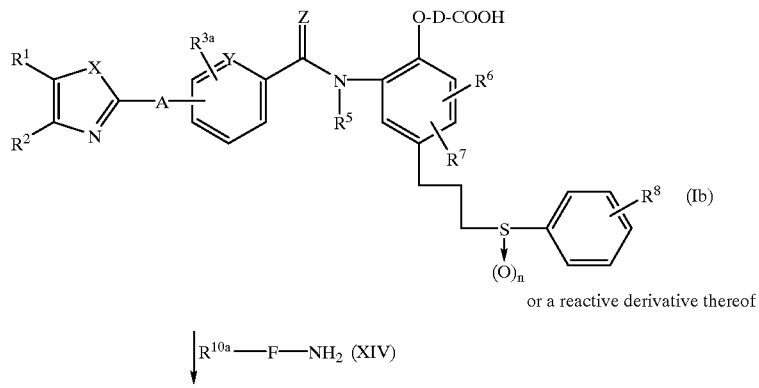

-continued

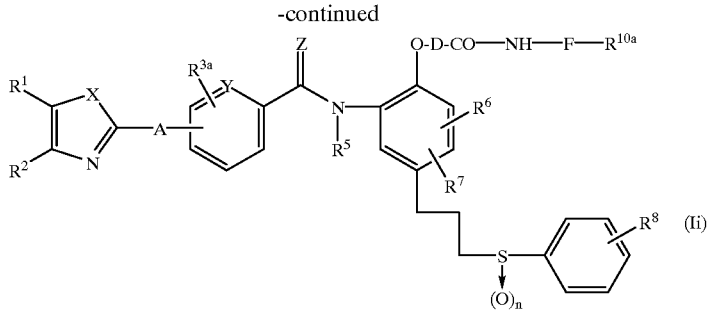

(In the above formulae, $R^{10a}$ is a group of $R^{10}$ other than a hydrogen atom. The same shall apply hereinafter.)

In the production method 6, the compound (Ii) of the present invention is obtained by allowing the compound (Ib) of the present invention or a reactive derivative thereof to react with an amine compound (XIV).

The reaction can be carried out in the same manner as the case of the first step of the production method 1.

Production Method 7

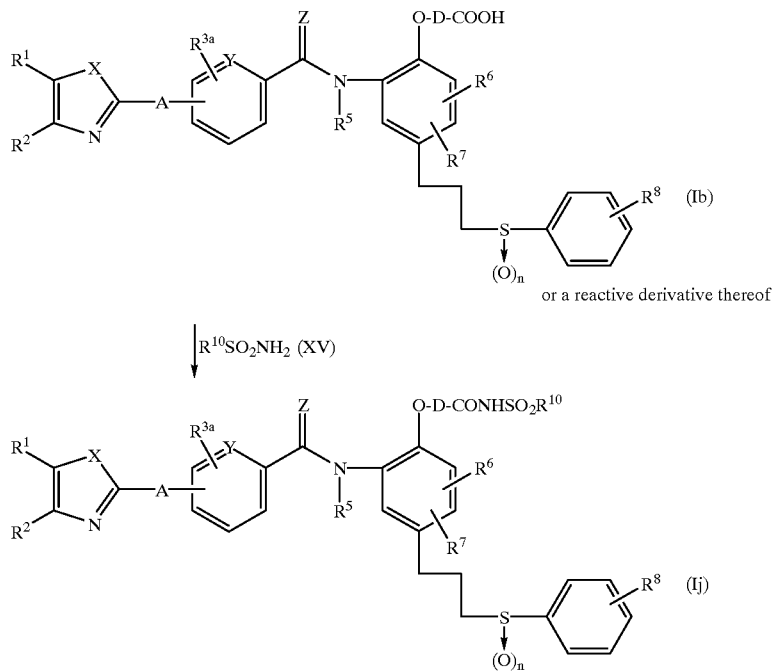

In the production method 7, the compound (Ij) of the present invention is obtained by allowing the compound (Ib) of the present invention or a reactive derivative thereof to react with a sulfonamide derivative represented by (XV) or the like.

The reaction is carried out using the compound (Ib) or a reactive derivative thereof and the compound (XV) at equimolar ratio or using one of then in a slightly excess amount, at ice-cooled or room temperature to heat refluxing temperature in the presence of an organic base such as 4-(dimethylamino)pyridine or the like or an inorganic base such as sodium hydroxide, potassium hydride or the like and, as occasion demands, by adding an appropriate dehydrating agent (for example, dicyclocarbodiimide or 1-(3-dimethylaminopropyl)-3-ethylcarbodiimide, or a hydrochloride or hydrobromide thereof).

As the solvent, an organic solvent inert to the reaction such as pyridine, THF, dioxane, diethyl ether, benzene, toluene, xylene, dichloromethane, dichloroethane, chloroform, DMF, ethyl acetate, acetonitrile or the like may be used.

Production Method 8

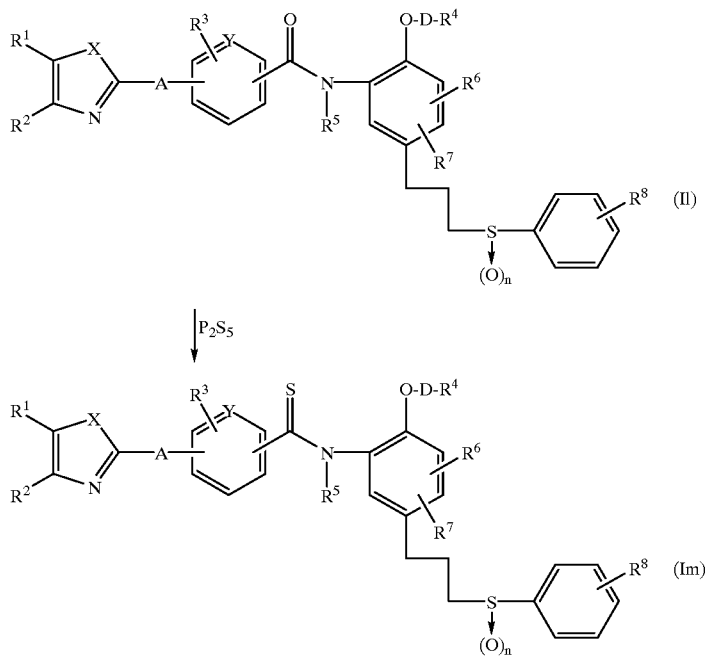

In the production method 8, a compound (Im) having a thiocarbonyl group is obtained from a compound (Il) having a carbonyl group. This reaction is carried out by allowing the compound (Il) to react with a phosphorus compound (e.g., diphosphorus pentasulfide or [2,4-bis(4-methoxyphenyl)-1, 3-dithia-2,4-diphosphethane-2,4-disulfide) in an amount corresponding to the reaction, at room temperature to heat refluxing temperature in an inert solvent such as 1,2-dimethoxyethane, chloroform, benzene or the like. In some cases, it is advantageous to add an inorganic base such as sodium bicarbonate or the like to the reaction system from the viewpoint of smooth progress of the reaction.

Production Method 9

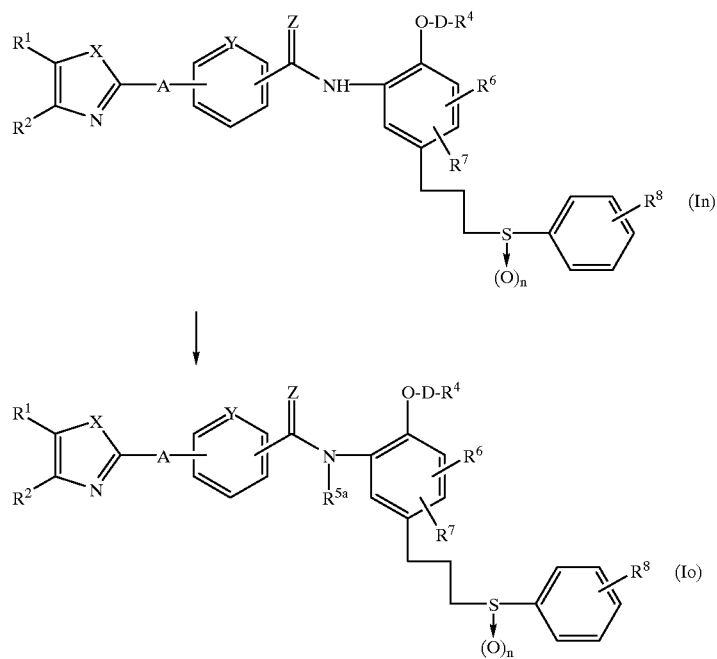

(In the above formulae, $R^{5a}$ is a lower alkyl group.)

In the production method 9, a compound (Io) is obtained by subjecting a compound (In) to N-alkylation reaction.

The reaction is carried out by stirring the amide compound (In) and an alkylating agent (for example, a halogenoalkane) in an amount corresponding to the reaction in a solvent inert to the reaction such as DMF, dimethyl sulfoxide, benzene or the like, at room temperature or with heating in the presence of an organic base such as 4-(dimethylamino)pyridine or the like or an inorganic base such as sodium hydroxide, potassium hydride or the like.

Production Method 10

In addition to the above production methods, the compound of the present invention can also be produced by modified methods known to those skilled in the art. For example, other compounds of interest of the present invention can be derived by a modified method of the production method 1 in which the starting compound (IV) is allowed to react with a compound from which a group represented by D-R$^4$ can be derived in advance according to the similar procedure to the second step of the production method 1, and then the resulting derivative of the compound (IV) is subjected to amidation reaction with a derivative of the compound (III) and, if necessary, further carrying out removal of the protecting group by hydrolysis, reduction or the like ad described in the foregoing.

Removal of Protecting Group

When R$^{3a}$ of the compounds (Ia), (Ib), (Ic), (Id), (Ie), (If), (Ig), (Ih), (Ii) and (Ij) of the present invention obtained by each of the aforementioned production methods is a protected hydroxyl group or a protected amino group, the protecting group is removed as occasion demands.

Removal of the hydroxyl group-protecting group can be carried out by 1) hydrolysis in the presence of an acid or base, 2) liquid ammonia reduction, 3) catalytic reduction using palladium-carbon or palladium hydroxide-carbon or 4) desilylation using an organic fluorine compound such as tetra-n-butylammonium fluoride or the like or an inorganic fluorine compound such as sodium fluoride, potassium fluoride, hydrofluoric acid or the like.

The hydrolysis of 1) may be a usual method in which hydrolysis is carried out in the presence of a base such as sodium carbonate, sodium hydroxide or the like or an acid such as trifluoroacetic acid, hydrochloric acid or the like, and the reaction is carried out preferably under a condition of from ice-cooled temperature to a temperature of 100° C.

The reduction method of 2) may be carried out by adding a compound having a hydroxyl group-protecting group to liquid ammonia, adding metallic sodium and then stirring the mixture.

The reduction method of 3) may be carried out at an ice-cooled temperature to a heating temperature in the presence of a catalyst such as palladium-carbon or palladium hydroxide-carbon.

The desilylation method of 4) may be carried out by allowing a compound having a hydroxyl group-protecting group to react with an organic fluorine compound such as tetra-n-butylammonium fluoride or the like or an inorganic fluorine compound such as sodium fluoride, potassium fluoride, hydrofluoric acid or the like in a solvent inert to the reaction, such as tetrahydrofuran, dichloromethane, DMF, benzene or the like.

Removal of the amino group-protecting group may be carried out by 1) reduction using zinc or iron, 2) liquid ammonia reduction or 3) catalytic reduction using palladium-carbon or palladium hydroxide-carbon.

The reduction method of 1) may be carried out by adding a compound having an amino group-protecting group to a buffer solution (an inert solvent is added, as occasion demands), further adding zinc in an amount corresponding to the reaction or in an excess amount and then stirring the mixture at an ice-cooled temperature to a heating temperature.

The reduction method of 2) may be carried out by adding a compound having an amino group-protecting group to liquid ammonia, adding metallic sodium and then stirring the mixture.

The reduction method of 3) may be carried out at an ice-cooled temperature to a heating temperature in the presence of a catalyst such as palladium-carbon or palladium hydroxide-carbon.

The reaction time of these reactions is optionally selected depending on the reaction conditions of starting compounds, reaction reagents and the like, but is generally from several tens of minutes to several tens of hours, preferably from several tens of minutes to several hours.

Starting materials for the production of the compound of the present invention can be produced easily using usual methods known to those skilled in the art. Typical production methods are described in the following.

Production Method of Compound (IV)

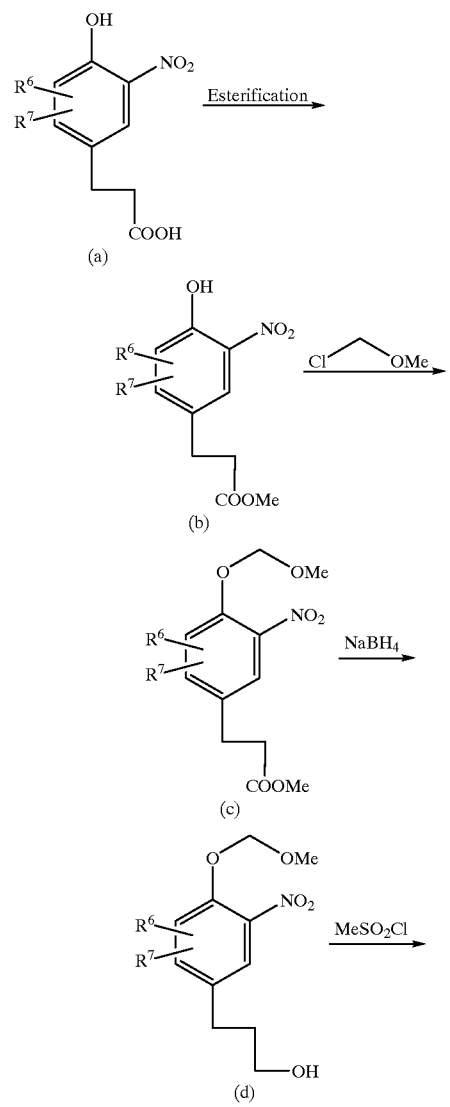

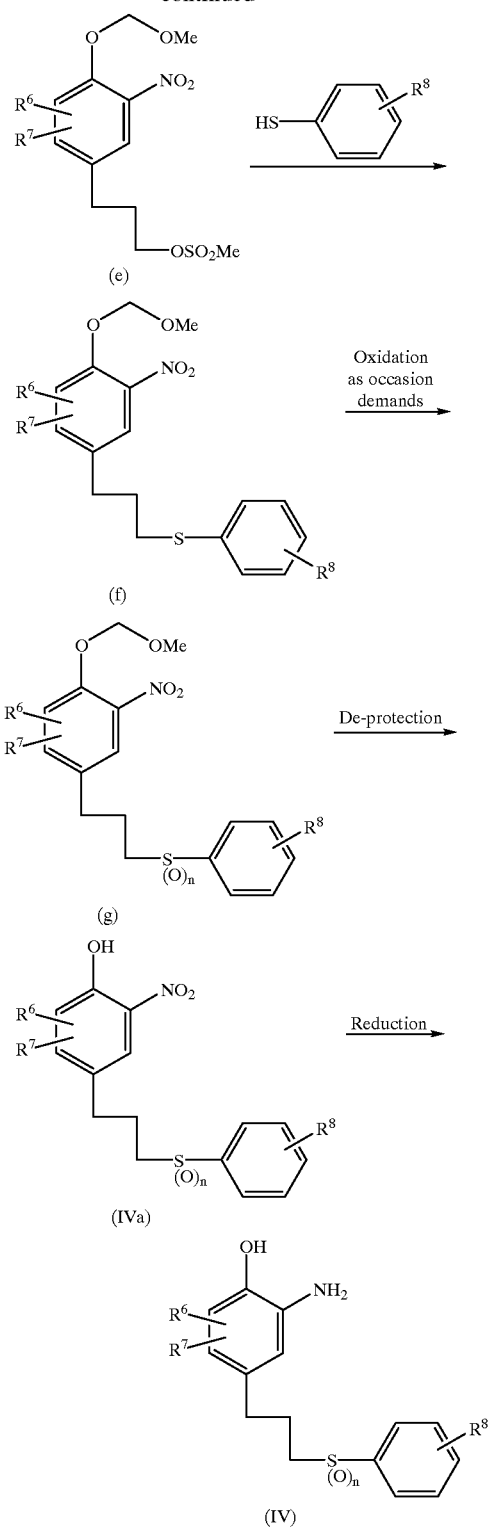

(Symbols in the above formulae are as defined in the foregoing.)

The alcohol compound (d) is obtained by subjecting the compound (a) to esterification in the usual way to protect the phenolic hydroxyl group with a methoxymethyl group and then reducing the ester. This is converted into methanesulfonic acid ester in the usual way and then allowed to react with benzenethiol, thereby obtaining the compound (f). After oxidizing the sulfide moiety as occasion demands, the methoxymethyl group is removed in the usual way and then the nitro group is reduced into an amino group to give the compound (IV) ($R^5$=H in this case).

Production Method of Compound (III)
(Case in which A is the formula —B—O—)

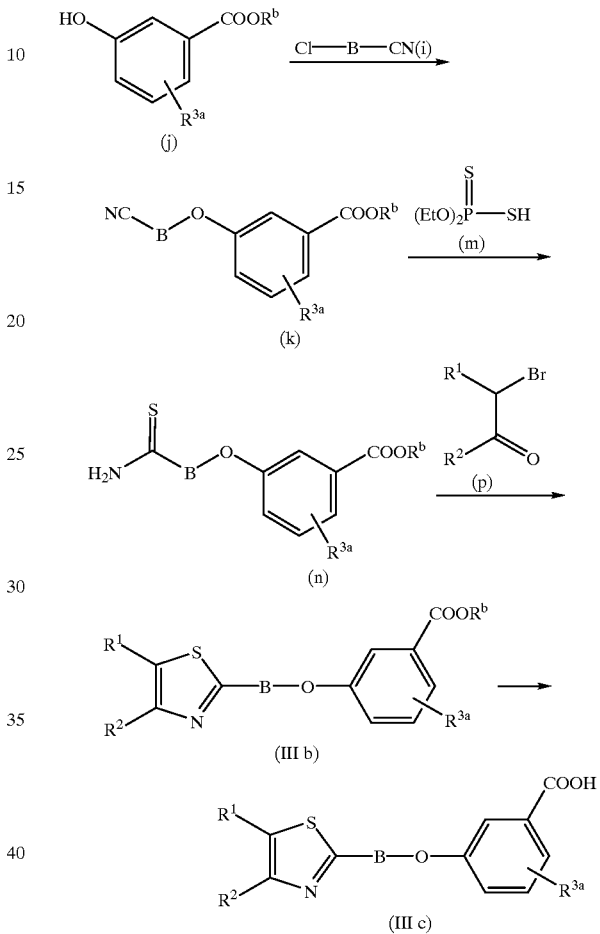

(In the above formulae, B, $R^1$ and $R^2$ are as defined in the foregoing, and $R^b$ is a lower alkyl group.)

The compound (j) is allowed to react with the compound (i) and then with the dithiophosphoric acid =O,O-diethyl (m) to give the compound (n) which is then allowed to react with the bromoketone (p), thereby obtaining the compound (IIIb). This compound is then hydrolyzed in the usual way to give the compound (IIIc).

The compound (III) can also be produced by conventional etherification or thioetherification reaction. A compound in which A is formula —CH=CH— can be produced by the method described in an unexamined published Japanese patent application (Kokai) No. 63-258854. By reducing this compound, a compound in which A is ethylene group can be obtained.

The compound of the present invention obtained in this manner is isolated and purified as a free compound, a salt thereof, a hydrate thereof, various solvates thereof such as a solvate with ethanol and the like, or as a polymorphic material. A pharmaceutically acceptable salt of the compound (I) can also be produced by subjecting the compound (I) to a conventional salt-forming reaction.

The isolation and purification are carried out by employing conventional chemical treatments such as extraction, fractional crystallization, various types of fractional chromatography and the like.

Various isomers can be separated by making use of the difference in physicochemical properties among isomers.

Also, an optical isomer in stereochemically pure form can be obtained by selecting an appropriate starting compound or by racemic resolution of a racemic compound (for example, a method in which a compound is converted into a diastereomer salt with a usual optically active acid or base and then subjected to optical resolution).

The compounds exemplified in the following can be synthesized by the aforementioned production methods, production methods which will be described later in the Examples, and the modified methods thereof known to those skilled in the art, without requiring special experiments.

A1) 4-[3-(4-chlorophenylsulfonyl)propyl]-2-[2-[2-(4-methyl-2-thiazolyl)vinyl]benzoylamino]phenoxyacetic acid
A2) 4-[3-(4-chlorophenylsulfonyl)propyl]-2-[2-[2-(5-ethyl-2-thiazolyl)vinyl]benzoylamino]phenoxyacetic acid
A3) 4-[3-(4-chlorophenylsulfonyl)propyl]-2-[2-[(5-phenyl-2-thiazolyl)methoxy]benzoylamino]phenoxyacetic acid
A4) 4-[3-(4-chlorophenylsulfonyl)propyl]-2-[2-[(4-phenyl-2-thiazolyl)thiomethyl]benzoylamino]phenoxyacetic acid
A5) 4-[3-(4-chlorophenylsulfonyl)propyl]-2-[2-[(5-phenyl-2-thiazolyl)methylthio]benzoylamino]phenoxyacetic acid
A6) 4-[3-(4-chlorophenylsulfonyl)propyl]-2-[3-[2-(5-methyl-2-thiazolyl)vinyl]benzoylamino]phenoxyacetic acid
A7) 4-[3-(4-chlorophenylsulfonyl)propyl]-2-[3-[2-(4-propyl-2-thiazolyl)vinyl]benzoylamino]phenoxyacetic acid
A8) 4-[3-(4-chlorophenylsulfonyl)propyl]-2-[3-[2-(5-phenyl-2-thiazolyl)vinyl]benzoylamino]phenoxyacetic acid
A9) 2-[3-[2-(5-t-butyl-2-thiazolyl)vinyl]benzoylamino]-4-[3-(4-chlorophenylsulfonyl)propyl]phenoxyacetic acid
A10) 4-[3-(4-chlorophenylsulfonyl)propyl]-2-[3-[2-(5-cyclohexyl-2-thiazolyl)vinyl]benzoylamino]phenoxyacetic acid
A11) 4-[3-(4-chlorophenylsulfonyl)propyl]-2-[3-[(4-cyclopentyl-2-thiazolyl)oxymethyl]benzoylamino]phenoxyacetic acid
A12) 4-[3-(4-chlorophenylsulfonyl)propyl]-2-[3-[(5-methyl-2-thiazolyl)oxymethyl]benzoylamino]phenoxyacetic acid
A13) 4-[3-(4-chlorophenylsulfonyl)propyl]-2-[3-[2-(4-phenyl-2-thiazolyl)oxymethyl]benzoylamino]phenoxyacetic acid
A14) 4-[3-(4-chlorophenylsulfonyl)propyl]-2-[3-[(5-phenyl-2-thiazolyl)methoxy]benzoylamino]phenoxyacetic acid
A15) 4-[3-(4-chlorophenylsulfonyl)propyl]-2-[3-[(5-ethyl-2-thiazolyl)methoxy]benzoylamino]phenoxyacetic acid
A16) 4-[3-(4-chlorophenylsulfonyl)propyl]-2-[3-[(5-methyl-2-thiazolyl)methoxy]benzoylamino]phenoxyacetic acid
A17) 4-[3-(4-chlorophenylsulfonyl)propyl]-2-[3-[(4-propyl-2-thiazolyl)methoxy]benzoylamino]phenoxyacetic acid
A18) 4-[3-(4-chlorophenylsulfonyl)propyl]-2-[3-[[4-(4-methylphenyl)-2-thiazolyl]methoxy]benzoylamino]phenoxyacetic acid
A19) 2-[3-[(5-t-butyl-2-thiazolyl)methoxy]benzoylamino]-4-[3-(4-chlorophenylsulfonyl)propyl]phenoxyacetic acid
A20) 2-[3-[(5-cyclobutyl-2-thiazolyl)methoxy]benzoylamino]-4-[3-(4-chlorophenylsulfonyl)propyl]phenoxyacetic acid
A21) 4-[3-(4-chlorophenylsulfonyl)propyl]-2-[3-[(5-phenyl-2-thiazolyl)thiomethyl]benzoylamino]phenoxyacetic acid
A22) 4-[3-(4-chlorophenylsulfonyl)propyl]-2-[3-[(5-isopropyl-2-thiazolyl)methylthio]benzoylamino]phenoxyacetic acid
A23) 4-[3-(4-chlorophenylsulfonyl)propyl]-2-[3-[(5-phenyl-2-thiazolyl)methylthio]benzoylamino]phenoxyacetic acid
A24) 4-[3-(4-chlorophenylsulfonyl)propyl]-2-[4-[2-(4-phenyl-2-thiazolyl)vinyl]benzoylamino]phenoxyacetic acid
A25) 4-[3-(4-chlorophenylsulfonyl)propyl]-2-[4-[2-(5-phenyl-2-thiazolyl)vinyl]benzoylamino]phenoxyacetic acid
A26) 4-[3-(4-chlorophenylsulfonyl)propyl]-2-[4-[2-(4-isopropyl-2-thiazolyl)vinyl]benzoylamino]phenoxyacetic acid
A27) 4-[3-(4-chlorophenylsulfonyl)propyl]-2-[4-[2-(5-methyl-2-thiazolyl)vinyl]benzoylamino]phenoxyacetic acid
A28) 4-[3-(4-chlorophenylsulfonyl)propyl]-2-[4-[(5-phenyl-2-thiazolyl)oxymethyl]benzoylamino]phenoxyacetic acid
A29) 2-[4-[(4-t-butyl-2-thiazolyl)oxymethyl]benzoylamino]-4-[3-(4-chlorophenylsulfonyl)propyl]phenoxyacetic acid
A30) 4-[3-(4-chlorophenylsulfonyl)propyl]-2-[4-[(4-phenyl-2-thiazolyl)methoxy]benzoylamino]phenoxyacetic acid
A31) 4-[3-(4-chlorophenylsulfonyl)propyl]-2-[4-[(5-phenyl-2-thiazolyl)methoxy]benzoylamino]phenoxyacetic acid
A32) 4-[3-(4-chlorophenylsulfonyl)propyl]-2-[4-[(4-isopropyl-2-thiazolyl)methoxy]benzoylamino]phenoxyacetic acid
A33) 4-[3-(4-chlorophenylsulfonyl)propyl]-2-[4-[(5-methyl-2-thiazolyl)methoxy]benzoylamino]phenoxyacetic acid
A34) 4-[3-(4-chlorophenylsulfonyl)propyl]-2-[4-[(5-isopropyl-2-thiazolyl)thiomethyl]benzoylamino]phenoxyacetic acid
A35) 4-[3-(4-chlorophenylsulfonyl)propyl]-2-[4-[(5-phenyl-2-thiazolyl)methylthio]benzoylamino]phenoxyacetic acid
A36) 4-[3-(4-chlorophenylsulfonyl)propyl]-2-[3-[2-(2-thiazolyl)vinyl]benzoylamino]phenoxyacetic acid
A37) 4-[3-(4-chlorophenylsulfonyl)propyl]-2-[3-[(2-thiazolyl)methoxy]benzoylamino]phenoxyacetic acid
A38) 3-[(4-cyclobutyl-2-thiazolyl)methylthio]-5'-[3-(4-chlorophenylsulfonyl)propyl]-2'-(1H-tetrazol-5-ylmethoxy)benzanilide
A39) 2-[3-[2-(4-cyclobutyl-2-thiazolyl)ethyl]benzoylamino]-4-[3-(4-chlorophenylsulfonyl)propyl]phenoxyacetic acid
A40) 2-[3-[(4-cyclobutyl-2-thiazolyl)methylthio]benzoylamino]-4-[3-(4-chlorophenylsulfonyl)propyl]phenoxyacetic acid
A41) 2-[3-[2-(4-tert-butyl-2-thiazolyl)ethyl]benzoylamino]-4-[3-(4-chlorophenylsulfonyl)propyl]phenoxyacetamide
A42) 2-[3-[(4-tert-butyl-2-thiazolyl)methylthio]benzoylamino]-4-[3-(4-chlorophenylsulfonyl)propyl]phenoxyacetamide
A43) 2-[3-[(4-cyclobutyl-2-thiazolyl)methoxy]benzoylamino]-4-[3-(4-chlorophenylsulfonyl)propyl]phenoxyacetamide
A44) 2-[3-[2-(4-cyclobutyl-2-thiazolyl)ethyl]benzoylamino]-4-[3-(4-chlorophenylsulfonyl)propyl]phenoxyacetamide A45) 2-[3-[(4-cyclobutyl-2-thiazolyl)methylthio]benzoylamino]-4-[3-(4-chlorophenylsulfonyl)propyl]phenoxyacetamide A46) 2-[2-[2-(5-chloro-2-benzothiazolyl)vinyl]benzoylamino]-4-[3-(4-chlorophenylsulfonyl)propyl]phenoxyacetic acid A47) 2-[2-[2-(2-benzothiazolyl)vinyl]benzoylamino]-4-[3-(4-chlorophenylsulfonyl)propyl]phenoxyacetic acid A48) 2-[2-[(5-chloro-2-benzothiazolyl)methoxy]benzoylamino]-4-[3-(4-chlorophenylsulfonyl)propyl]phenoxyacetic acid A49) 2-[2-[(2-benzothiazolyl)thiomethyl]benzoylamino]-4-[3-(4-chlorophenylsulfonyl)propyl]phenoxyacetic acid A50) 2-[2-[(5-bromo-2-benzothiazolyl)methylthio]benzoylamino]-4-[3-(4-chlorophenylsulfonyl)propyl]phenoxyacetic acid A51) 4-[3-(4-chlorophenylsulfonyl)propyl]-2-[3-[2-(5-fluoro-2-benzothiazolyl)vinyl]benzoylamino]phenoxyacetic acid A52) 4-[3-(4-chlorophenylsulfonyl)propyl]-2-[3-[2-(7-fluoro-2-benzothiazolyl)vinyl]benzoylamino]phenoxyacetic acid A53) 2-[3-[2-(4-chloro-2-benzothiazolyl)vinyl]benzoylamino]-4-[3-(4-chlorophenylsulfonyl)propyl]phenoxyacetic acid A54) 2-[3-[2-(6-chloro-2-benzothiazolyl)vinyl]benzoylamino]-4-[3-(4-chlorophenylsulfonyl)propyl]phenoxyacetic acid A55) 4-[3-(4-chlorophenylsulfonyl)propyl]-2-[3-[2-(5-trifluoromethyl-2-benzothiazolyl)vinyl]benzoylamino]phenoxyacetic acid A56) 2-[3-[(2-benzothiazolyl)oxymethyl]benzoylamino]-4-[3-(4-chlorophenylsulfonyl)propyl]phenoxyacetic acid A57) 2-[3-[(5-chloro-2-benzothiazolyl)oxymethyl]benzoylamino]-4-[3-(4-chlorophenylsulfonyl)propyl]phenoxyacetic acid A58) 2-[3-[(6-chloro-2-benzothiazolyl)oxymethyl]benzoylamino]-4-[3-(4-chlorophenylsulfonyl)propyl]phenoxyacetic acid A59) 2-[3-[(4-chloro-2-benzothiazolyl)methoxy]benzoylamino]-4-[3-(4-chlorophenylsulfonyl)propyl]phenoxyacetic acid A60) 2-[3-[(6-chloro-2-benzothiazolyl)methoxy]benzoylamino]4-[3-(4-chlorophenylsulfonyl)propyl]phenoxyacetic acid A61) 2-[3-[(5-bromo-2-benzothiazolyl)thiomethyl]benzoylamino]-4-[3-(4-chlorophenylsulfonyl)propyl]phenoxyacetic acid A62) 2-[3-[(5-chloro-2-benzothiazolyl)methylthio]benzoylamino]-4-[3-(4-chlorophenylsulfonyl)propyl]phenoxyacetic acid A63) 2-[3-[(2-benzothiazolyl)methylthio]benzoylamino]-4-[3-(4-chlorophenylsulfonyl)propyl]phenoxyacetic acid A64) 2-[3-[(2-benzoxazolyl)oxymethyl]benzoylamino]-4-[3-(4-chlorophenylsulfonyl)propyl]phenoxyacetic acid A65) 2-[3-[(2-benzoxazolyl)thiomethyl]benzoylamino]-4-[3-(4-chlorophenylsulfonyl)propyl]phenoxyacetic acid A66) 2-[3-[2-(2-benzoxazolyl)vinyl]benzoylamino]-4-[3-(4-chlorophenylsulfonyl)propyl]phenoxyacetic acid A67) 2-[3-[(5-chloro-2-benzoxazolyl)oxymethyl]benzoylamino]-4-[3-(4-chlorophenylsulfonyl)propyl]phenoxyacetic acid A68) 2-[3-[2-(5-chloro-2-benzoxazolyl)vinyl]benzoylamino]-4-[3-(4-chlorophenylsulfonyl)propyl]phenoxyacetic acid A69) 4-[3-(4-chlorophenylsulfonyl)propyl]-2-[4-[2-(4-fluoro-2-benzothiazolyl)vinyl]benzoylamino]phenoxyacetic acid A70) 2-[4-[2-(5-bromo-2-benzothiazolyl)vinyl]benzoylamino]-4-[3-(4-chlorophenylsulfonyl)propyl]phenoxyacetic acid A71) 4-[3-(4-chlorophenylsulfonyl)propyl]-2-[4-[2-(7-fluoro-2-benzothiazolyl)vinyl]benzoylamino]phenoxyacetic acid A72) 4-[3-(4-chlorophenylsulfonyl)propyl]-2-[4-[2-(5-trifluoromethyl-2-benzothiazolyl)vinyl]benzoylamino]phenoxyacetic acid A73) 2-[4-[(5-chloro-2-benzothiazolyl)oxymethyl]benzoylamino]-4-[3-(4-chlorophenylsulfonyl)propyl]phenoxyacetic acid A74) 2-[4-[(6-chloro-2-benzothiazolyl)oxymethyl]benzoylamino]-4-[3-(4-chlorophenylsulfonyl)propyl]phenoxyacetic acid A75) 2-[4-[(4-chloro-2-benzothiazolyl)methoxy]benzoylamino]-4-[3-(4-chlorophenylsulfonyl)propyl]phenoxyacetic acid A76) 4-[3-(4-chlorophenylsulfonyl)propyl]-2-[4-[(6-trifluoromethyl-2-benzothiazolyl)methoxy]benzoylamino]phenoxyacetic acid A77) 2-[4-[(5-chloro-2-benzothiazolyl)thiomethyl]benzoylamino]-4-[3-(4-chlorophenylsulfonyl)propyl]phenoxyacetic acid A78) 2-[4-[(5-chloro-2-benzothiazolyl)methylthio]benzoylamino]-4-[3-(4-chlorophenylsulfonyl)propyl]phenoxyacetic acid A79) 2-[4-[(2-benzoxazolyl)oxymethyl]benzoylamino]-4-[3-(4-chlorophenylsulfonyl)propyl]phenoxyacetic acid A80) 2-[4-[(2-benzoxazolyl)thiomethyl]benzoylamino]-4-[3-(4-chlorophenylsulfonyl)propyl]phenoxyacetic acid A81) 2-[4-[2-(2-benzoxazolyl)vinyl]benzoylamino]-4-[3-(4-chlorophenylsulfonyl)propyl]phenoxyacetic acid A82) 2-[4-[(5-chloro-2-benzoxazolyl)oxymethyl]benzoylamino]-4-[3-(4-chlorophenylsulfonyl)propyl]phenoxyacetic acid A83) 2-[4-[2-(5-bromo-2-benzoxazolyl)vinyl]benzoylamino]-4-[3-(4-chlorophenylsulfonyl)propyl]phenoxyacetic acid A84) 4-[3-(4-chlorophenylsulfonyl)propyl]-2-[2-[2-(4-fluoro-2-benzothiazolyl)vinyl]benzoylamino]phenoxyacetic acid A85) 4-[3-(4-chlorophenylsulfonyl)propyl]-2-[2-[(5-methoxy-2-benzoxazolyl)oxymethyl]benzoylamino]phenoxyacetic acid A86) 4-[3-(4-chlorophenylsulfonyl)propyl]-2-[2-[(6-nitro-2-benzothiazolyl)methylthio]benzoylamino]phenoxyacetic acid A87) 4-[3-(4-chlorophenylsulfonyl)propyl]-2-[2-[(7-methyl-2-benzoxazolyl)thiomethyl]benzoylamino]phenoxyacetic acid A88) 4-[3-(4-chlorophenylsulfonyl)propyl]-2-[3-[2-(4-ethyl-2-benzothiazolyl)vinyl]benzoylamino]phenoxyacetic acid A89) 4-[3-(4-chlorophenylsulfonyl)propyl]-2-[3-[(5-cyano-2-benzoxazolyl)oxymethyl]benzoylamino]phenoxyacetic acid A90) 4-[3-(4-chlorophenylsulfonyl)propyl]-2-[3-[(6-hydroxy-2-benzothiazolyl)methylthio]benzoylamino]phenoxyacetic acid A91) 2-[3-(7-chloro-2-benzoxazolyl)thiomethyl]benzoylamino]-4-[3-(4-chlorophenylsulfonyl)propyl]phenoxyacetic acid A92) 2-[3-(5-bromo-2-benzothiazolylmethoxy)benzoylamino]-4-[3-(4-chlorophenylsulfonyl)propyl]phenoxyacetic acid A93) 4-[3-(4-chlorophenylsulfonyl)propyl]-2-[4-[(6-trifluoromethyl-2-benzothiazolyl)methylthio]benzoylamino]phenoxyacetic acid A94) 4-[3-(4-chlorophenylsulfonyl)propyl]-2-[4-[(7-hydroxy-2-benzoxazolyl)thiomethyl]benzoylamino]phenoxyacetic acid A95) 5'-[3-(4-bromophenylsulfonyl)propyl]-3-[(4-tert-butyl-2-thiazolyl)methoxy]-2'-(1H-tetrazol-5-ylmethoxy)benzanilide A96) 3-[(4-tert-butyl-2-thiazolyl)methoxy]-5'-[3-(4-fluorophenylsulfonyl)propyl]-2'-(1H-tetrazol-5-ylmethoxy)benzanilide A97) 3-[(4-tert-butyl-2-thiazolyl)methoxy]-5'-[3-(4-iodophenylsulfonyl)propyl]-2'-(1H-tetrazol-5-ylmethoxy)benzanilide A98) 3-[(4-tert-butyl-2-thiazolyl)methoxy]-5'-[3-(4-methylphenylsulfonyl)propyl]-2'-(1H-tetrazol-5-ylmethoxy)benzanilide A99) 3-[(4-tert-butyl-2-thiazolyl)methoxy]-2'-(1H-tetrazol-5-ylmethoxy)-5'-[3-(4-trifluoromethylphenylsulfonyl)propyl]benzanilide A100) 5'-[3-(4-chlorophenylsulfonyl)propyl]-3-[(2-propyl)-2-thiazolylmethoxy]-2'-(1H-tetrazol-5-ylmethoxy)benzanilide A101) 5'-[3-(4-chlorophenylsulfonyl)propyl]-3-[4-(2-methylpropyl)-2-thiazolylmethoxy]-2'-(1H-tetrazol-5-ylmethoxy)benzanilide A102) 3-[4-cyclopropyl-2-thiazolylmethoxy]-5'-[3-(4-chlorophenylsulfonyl)propyl]-2'-(1H-tetrazol-5-ylmethoxy)benzanilide A103) 3-[4-cyclopentyl-2-thiazolylmethoxy]-5'-[3-(4-chlorophenylsulfonyl)propyl]-2'-(1H-tetrazol-5-ylmethoxy)benzanilide A104) 5'-[3-(4-chlorophenylsulfonyl)propyl]-3-[4-(2-propyl)-2-thiazolylmethylthio]-2'-(1H-tetrazol-5-ylmethoxy)benzanilide A105) 5'-[3-(4-chlorophenylsulfonyl)propyl]-3-[4-(2-methylpropyl)-2-thiazolylmethylthio]-2'-(1H-tetrazol-5-ylmethoxy)benzanilide A106) 3-[4-cyclopropyl-2-thiazolylmethylthio]-5-[3-(4-chlorophenylsulfonyl)propyl]-2'-(1H-tetrazol-5-ylmethoxy)benzanilide A107) 3-[4-cyclopentyl-2-thiazolylmethylthio]-5'-[3-(4-chlorophenylsulfonyl)propyl]-2'-(1H-tetrazol-5-ylmethoxy)benzanilide A108) 3-[4-cyclobutyl-2-thiazolylmethylthio]-5'-[3-(4-chlorophenylsulfonyl)propyl]-2'-(1H-tetrazol-5-ylmethoxy)benzanilide A109) 5'-[3-(4-chlorophenylsulfonyl)propyl]-3-[2-[4-(2-propyl)-2-thiazolyl]ethyl]-2'-(1H-tetrazol-5-ylmethoxy)benzanilide A110) 5'-[3-(4-chlorophenylsulfonyl)propyl]-3-[2-[4-(2-methylpropyl)-2-thiazolyl]ethyl]-2'-(1H-tetrazol-5-ylmethoxy)benzanilide A111) 3-[2-[4-cyclopropyl-2-thiazolyl]ethyl]-5'-[3-(4-chlorophenylsulfonyl)propyl]-2'-(1H-tetrazol-5-ylmethoxy)benzanilide A112) 3-[2-[4-cyclopentyl-2-thiazolyl]ethyl]-5'-[3-(4-chlorophenylsulfonyl)propyl]-2'-(1H-tetrazol-5-ylmethoxy)benzanilide A113) 5'-[3-(4-chlorophenylsulfonyl)propyl]-3-[2-[4-(2-propyl)-2-thiazolyl]vinyl]-2'-(1H-tetrazol-5-ylmethoxy)benzanilide A114) 5'-[3-(4-chlorophenylsulfonyl)propyl]-3-[2-[4-(2-methylpropyl)-2-thiazolyl]vinyl]-2'-(1H-tetrazol-5-ylmethoxy)benzanilide A115) 3-[2-[4-cyclopropyl-2-thiazolyl]vinyl]-5'-[3-(4-chlorophenylsulfonyl)propyl]-2'-(1H-tetrazol-5-ylmethoxy)benzanilide A116) 3-[2-[4-cyclopentyl-2-thiazolyl]vinyl]-5'-[3-(4-chlorophenylsulfonyl)propyl]-2'-(1H-tetrazol-5-ylmethoxy)benzanilide A117) 3-[2-[4-cyclobutyl-2-thiazolyl]vinyl]-5'-[3-(4-chlorophenylsulfonyl)propyl]-2'-(1H-tetrazol-5-ylmethoxy)benzanilide A118) 3-[2-[4-tert-butyl-2-thiazolyl]vinyl]-5'-[3-(4-chlorophenylsulfonyl)propyl]-2'-(1H-tetrazol-5-ylmethoxy)benzanilide A119) 5'-[3-(4-chlorophenylsulfonyl)propyl]-3-[4-(2-propyl)-2-thiazolyloxymethyl]-2'-(1H-tetrazol-5-ylmethoxy)benzanilide A120) 5'-[3-(4-chlorophenylsulfonyl)propyl]-3-[4-(2-methylpropyl)-2-thiazolyloxymethyl]-2'-(1H-tetrazol-5-ylmethoxy)benzanilide A121) 3-[4-cyclopropyl-2-thiazolyloxymethyl]-5'-[3-(4-chlorophenylsulfonyl)propyl]-2'-(1H-tetrazol-5-ylmethoxy)benzanilide A122) 3-[4-cyclopentyl-2-thiazolyloxymethyl]-5'-[3-(4-chlorophenylsulfonyl)propyl]-2'-(1H-tetrazol-5-ylmethoxy)benzanilide A123) 3-[4-cyclobutyl-2-thiazolyloxymethyl]-5'-[3-(4-chlorophenylsulfonyl)propyl]-2'-(1H-tetrazol-5-ylmethoxy)benzanilide A124) 3-[4-tert-butyl-2-thiazolyloxymethyl]-5'-[3-(4-chlorophenylsulfonyl)propyl]-2'-(1H-tetrazol-5-ylmethoxy)benzanilide A125) 5'-[3-(4-chlorophenylsulfonyl)propyl]-3-[4-(2-propyl)-2-thiazolylthiomethyl]-2'-(1H-tetrazol-5-ylmethoxy)benzanilide A126) 5'-[3-(4-chlorophenylsulfonyl)propyl]-3-[4-(2-methylpropyl)-2-thiazolylthiomethyl]-2'-(1H-tetrazol-5-ylmethoxy)benzanilide A127) 3-[4-cyclopropyl-2-thiazolylthiomethyl]-5'-[3-(4-chlorophenylsulfonyl)propyl]-2'-(1H-tetrazol-5-ylmethoxy)benzanilide A128) 3-[4-cyclopentyl-2-thiazolylthiomethyl]-5'-[3-(4-chlorophenylsulfonyl)propyl]-2'-(1H-tetrazol-5-ylmethoxy)benzanilide A129) 3-[4-cyclobutyl-2-thiazolylthiomethyl]-5'-[3-(4-chlorophenylsulfonyl)propyl]-2'-(1H-tetrazol-5-ylmethoxy)benzanilide A130) 3-[4-tert-butyl-2-thiazolylthiomethyl]-5'-[3-(4-chlorophenylsulfonyl)propyl]-2'-(1H-tetrazol-5-ylmethoxy)benzanilide

INDUSTRIAL APPLICABILITY

The compound of the present invention is an agent which has both of $TXA_2$ antagonizing activity and LTs antagonizing activity and is also possessed of excellent oral absorbability. In consequence, the compound of the present invention is useful as agents for the prevention and treatment of $TXA_2$-related diseases and LTs-related diseases, for example, as agents for the prevention and treatment of allergic diseases (such as bronchial asthma, allergic rhinitis, urticaria and the like), ischemic heart and brain diseases, thrombosis, angina pectoris, inflammatory and peptic ulcers and hepatic diseases. It is particularly useful for the prevention and treatment of allergic diseases (such as bronchial asthma, allergic rhinitis, urticaria and the like), ischemic heart and brain diseases and thrombosis in which both of the mediators are concerned.

Availability of the compound of the present invention was confirmed by the following test examples on its $TXA_2$ antagonism and LTs antagonism and its effects by oral administration.

Test Examples (1) Test Method for the Inhibition of Platelet Aggregation Induced by U-46619

Using a plastic syringe containing 1 volume of 3.8% sodium citrate aqueous solution, 9 volumes of blood was collected from the abdominal aorta of a male Hartley guinea pig of about 800 g in body weight. Platelet rich plasma (PRP) was obtained by subjecting the blood to 10 minutes of centrifugation at 270×g, and the remaining blood was further centrifuged at 1,100×g for 10 minutes to give platelet poor plasma (PPP). The PRP was diluted with PPP to control the platelet count to 500,000/μl, and platelet aggregation by a stable analog of $TXA_2$, U-46619 (a chemical name: 9,11-dideoxy-9α,11α-methanoepoxy-prostaglandin $F_2α$), was measured in accordance with the method of Bone and Cross (*Journal of Physiology*, vol.168, pp.178–195, 1963).

That is, changes in the light transmittance of PRP by U-46619 ($10^{-6}$ or M) was measured using NBS Hematracer. The compound was added 2 minutes before the addition of U-46619, and the $IC_{50}$ value (50% inhibition concentration) was calculated from the inhibition ratio based on the maximum light transmittance by U-46619. The results are shown in Table 1.

(2) Test Method for the Inhibition of Ileal Contraction by $LTD_4$ in Guinea Pig A male Hartley guinea pig of 500 to 700 g in body weight was sacrificed by head blow. The ileum was set in a Magnus vessel containing 10 ml of Tyrode solution aerated with a 95% $O_2$+5% $CO_2$ mixture gas at a tension of 1.0 g. The tension generated by the tissue was isometrically measured using a threton gage transducer. Ileal contraction reaction against $LTD_4$ ($10^{-9}$ M) was measured in the absence of the compound and then in the presence of the test compound in varied concentrations. Incubation time of the compound was set to 20 minutes. The results are shown in Table 1.

(3) Test Method for the Inhibition of U-46619 Induced Airway Resistance Increase in Guinea Pig by Oral Administration of Compounds A male Hartley guinea pig (500 to 800 g) was anesthetized with urethane (1.2 g/kg, i.p.) and fixed on the back to insert a tracheal cannula. Spontaneous respiration was stopped with gallamine (1 mg/kg, i.v.) and artificial respiration was carried out at a rate of 60 strokes/min, volume 1 ml/100 g body weight/cycle. After total jugular intravenous administration of U-46619 (3 μg/kg), the increasing airway resistance was measured by a respiration function measuring apparatus (Model 6, Buxco Electronics Inc.). In this case, test compound was orally administered 1 hour before the administration of U-46619, as a dimethyl sulfoxide solution or as a methyl cellulose suspension.

The results were calculated as the inhibition ratio of airway resistance at the time of the administration of 10 mg/kg of the compound. Results of typical compounds are shown in Table 2.

(4) Test Method for the Inhibition of $LTD_4$-Induced Vascular Permeability Acceleration by Oral Administration of Compounds A male Hartley guinea pig whose dorsal hair had been cut on the day before the test was subjected to intravenous administration of 1% Evans blue aqueous solution (1 ml/animal). Two minutes thereafter, $LTD_4$ (5 ng/site) was administered inside the dorsal skin of the guinea pig, and the guinea pig was sacrificed by decapitation 30 minutes thereafter. The skin where intracutaneous injection of $LTD_4$ was carried out was collected, and the pigment leaked into the skin was extracted. Amount of the leaked pigment was calculated by measuring its absorbance at 620 nm and used as the index of vascular permeability. The test compound was orally administered as a dimethyl sulfoxide solution 1 hour before the intracutaneous administration of $LTD_4$. The results were calculated as the inhibition ratio at the time of the administration of 10 mg/kg of the compound. Results of typical compounds are shown in Table 2.

(5) Test Method for the Inhibition of Airway Resistance Increase Induced by Antigen in Actively Sensitized Guinea Pig As the antigen, ovalbumin (OA) was administered together with $Al(OH)_3$ to a Hartley male guinea pig by intraperitoneal injection three times at intervals of 2 weeks to effect active sensitization. Under urethane anesthesia and artificial respiration, the antigen (OA) was administered by intravenous injection to the sensitized guinea pig 1 to 2 weeks after the final sensitization, and the airway resistance was measured with the passage of time. In this case, gallamine (1 mg/kg) was administered by intravenous injection 10 minutes before the administration of the antigen, and indomethacin (2 mg/kg) 3 minutes before and mepyramine (2 mg/kg) and propranolol (0.3 mg/kg) 2 minutes before the antigen administration. The test compound was oral administered 1 hour before the administration of antigen. By calculating change ratio of the airway resistance after the antigen administration, effect of the test compound was examined using its action to inhibit the airway resistance increase as the index. In this test, the compound of the present invention showed excellent action to inhibit the airway resistance increase.

TABLE 1

| Example No. | Test (1), $IC_{50}$, μM | Test (2), $IC_{50}$, nM |
| --- | --- | --- |
| 6 | 0.45 | 0.81 |
| 13 | 0.055 | 0.45 |
| 15 | 0.063 | 0.85 |
| 26 | 0.079 | 0.54 |
| 27 | 0.21 | 0.67 |
| 28 | 0.074 | 0.98 |
| 29 | 0.11 | 0.61 |
| 31 | 0.13 | 0.28 |
| 39 | 0.22 | 0.57 |
| 42 | 0.42 | 0.93 |
| 74 | 0.54 | 0.24 |
| 79 | 0.89 | 4.2 |
| 106 | 1.2 | 0.92 |
| 107 | 0.67 | 3.7 |
| 111 | 0.38 | 0.26 |

TABLE 2

| | Test (3) Inhibition ratio (%) | Test (4) Inhibition ratio (%) |
| --- | --- | --- |
| Comparative compound | 27 (DMSO), 21 (MC) | 35 (DMSO) |
| Example 31 | 72 (DMSO) | 40 (DMSO) |

Comparative compound: 4-[3-(4-chlorophenylsulfonyl)propyl]-2-[3-(2-quinolylmethoxy)benzoylamino]phenoxyacetic acid (compound of Example 2 in an unexamined published Japanese patent application (Kokai) No. 4-154766)
DMSO: administered as a dimethyl sulfoxide solution
MC: administered as a methyl cellulose suspension The pharmaceutical composition which contains one or two or more of compounds represented by the general formula (I) and pharmaceutically acceptable salts thereof as the active ingredient is orally or parenterally administered, by making it into the dosage forms such as tablets, powders, fine granules, granules, capsules, pills, solutions, injections, suppositories, ointments, adhesive preparations and the like using carriers, excipients and other additives commonly used for the production of pharmaceutical preparations.

Clinical dose of the compound of the present invention in human is optionally decided taking into consideration symptoms, body weight, age, sex and the like of each patient to be treated, but is generally from 0.1 to 500 mg for oral administration, and from 0.01 to 100 mg for parenteral administration, per day per adult, and the daily dose is administered once a day or by dividing it into several doses per day. Since the dose varies depending on various conditions, sufficient effects may be obtained by a smaller dose than the above range in some cases.

Tablets, powders, granules and the like are used as the solid composition of the present invention for oral administration. In such solid composition, one or more of the active substances are mixed with at least one inert diluting agent such as lactose, mannitol, glucose, hydroxypropylcellulose, microcrystalline cellulose, starch, polyvinyl pyrrolidone, metasilicic acid, magnesium aluminate or the like. In the usual way, the composition may contain additive agents in addition to the inert diluting agent, such as lubricating agents (e.g., magnesium stearate or the like), disintegrating agents (e.g., calcium cellulose glycolate or the like), stabilizing agents (e.g., lactose or the like) and solubilizing or solubilization-assisting agent (e.g., glutamic acid, aspartic acid or the like). As occasion demands, tablets or pills may be coated with films of gastric or enteric substances such as sucrose, gelatin, hydroxypropylcellulose, hydroxypropylmethylcellulose phthalate and the like.

The liquid composition for use in oral administration includes pharmaceutically acceptable emulsions, solutions, suspensions, syrups, elixirs and the like, which contain a generally used inert diluting agent such as purified water or ethyl alcohol. In addition to the inert diluting agent, this composition may also contain assisting agents such as a solubilizing or solubilization-assisting agent, a moistening agent, a suspending agent and the like, a sweetener, a flavoring agent, an aromatic agent and an antiseptic agent.

The injections for parenteral administration include aseptic aqueous or non-aqueous solutions, suspensions and emulsions. Examples of the diluting agent of aqueous solutions and suspensions include distilled water for injection use and physiological saline. Examples of the diluting agent of non-aqueous solutions and suspensions include propylene glycol, polyethylene glycol, plant oils such as olive oil, alcohols such as ethyl alcohol and polysorbate 80 (trade name). Such compositions may further contain additive agents such as a tonicity agent, an antiseptic agent, a moistening agent, an emulsifying agent, a dispersing agent, a stabilizing agent (e.g., lactose), and a solubilizing or solubilization-assisting agent. These compositions are sterilized by filtration through a bacteria-retaining filter, blending of a germicide, or irradiation. They may be made into aseptic solid compositions in advance and then dissolved in sterile water or an aseptic solvent for injection use prior to their use.

When the compound of the present invention has low solubility, a solubilization treatment may be employed. The solubilization treatment may be effected by known methods which can be applied to pharmaceutical preparations, such as a method in which surface active agents (e.g., polyoxyethylene hydrogenated castor oils, polyoxyethylene sorbitan higher fatty acid esters, polyoxyethylene polyoxypropylene glycols, sucrose fatty acid esters and the like) are added and a method in which the agent is made into a solid dispersion with a solubilizing agent such as a polymer (for example, water soluble polymers such as hydroxypropylmethylcellulose (HPMC), polyvinyl pyrrolidone (PVP), polyethylene glycol (PEG) or the like or enteric polymers such as carboxymethylethylcellulose (CMEC), hydroxypropylmethylcellulose phthalate (HPMCP), methyl methacrylate-methacrylic acid copolymer (Eudragit L, S, trade name; manufactured by Rohm & Haas Co,) or the like). A method in which the agent is made into a soluble salt and a method in which an inclusion compound is formed using cyclodextrin or the like may also be employed, as the occasion demands. The solubilization means can optionally be changed depending on the agent of interest ("*Saikin no seizaigijyutu to sonooyo I*", I. Utsumi et al., *Iyaku Journal*, 157–159 (1983) and "*Iyaku Monograph* No. 1, *Seibutugakuteki riyono*", K. Nagai et al., Soft Science, 78–82 (1988)].

The method in which solubility of the agent is improved by forming a solid dispersion with a solubilizing agent (an unexamined published Japanese patent application (Kokai) No. 56-49314, FR 2460667) is preferably employed.

BEST MODE OF CARRYING OUT THE INVENTION

Next, compounds of interest of the present invention and their production methods are described further in detail with reference to the following examples, but the present invention should not be restricted thereby.

REFERENCE EXAMPLE 1

(1) The phenolic hydroxyl group of 3-(4-hydroxy-3-nitrophenyl)propionic acid (*J. Heterocycl. Chem.,* 9 (3), 681, (1972)) was protected with a methoxymethyl group and the carboxylic acid moiety was esterified with an appropriate alcohol. The resulting ester was reduced to an alcohol and then the hydroxyl group was subjected to methanesulfonylation, thereby synthesizing 3-(4-methoxymethoxy-3-nitrophenyl)propyl=methylsulfonate.

(2) 60% Sodium hydride (4.47 g, 0.11 mol) was suspended in tetrahydrofuran (100 ml), and 4-chlorothiophenol (15.85 g, 0.11 mol) was added dropwise with stirring under ice-cooling.

After additional 30 minutes of stirring of the reaction mixture under ice-cooling, 3-(4-methoxymethoxy-3-nitrophenyl)propyl=methylsulfonate (35.00 g, 0.11 mol) which had been dissolved in tetrahydrofuran (100 ml) was added dropwise spending 1 hour. Thereafter, the reaction solution was stirred under ice-cooling for 1 hour and at room temperature for 1 hour and then concentrated under reduced pressure. Water was added to the resulting residue and the product formed was extracted twice with chloroform. The organic layer was washed with 5% potassium carbonate aqueous solution and brine in that order, dried over anhydrous magnesium sulfate, and then concentrated under reduced pressure. The resulting residue was purified by silica gel column chromatography (eluent, chloroform:hexane=1:4–7:3) to give 4-chlorophenyl=3-(4-methoxymethoxy-3-nitrophenyl)propyl=sulfide (40.30 g, 100%) as an oily material.

Mass spectrometry data (m/z): 367 ($M^+$)

Nuclear magnetic resonance spectrum ($CDCl_3$, TMS internal standard)

δ: 1.95–2.01 (2H, m), 2.79 (2H, br-t, J=7.9 Hz), 2.94 (2H, br-t, J=7.3 Hz), 3.52 (3H, s), 5.26 (2H, s), 7.26–7.44 (6H, m), 7.68 (1H, br-d, J=2.4 Hz)

(3) 4-Chlorophenyl=3-(4-methoxymethoxy-3-nitrophenyl)propyl=sulfide (40.00 g, 108.87 mmol) was dissolved in dichloromethane (800 ml). To the resulting solution kept at 0° C. or below was added 80% 3-chloroperbenzoic acid (49.32 g, 228.63 mmol) in small portions. After stirring the reaction solution at the same temperature for 1 hour and then at room temperature for 1 hour, ice and 5% potassium carbonate aqueous solution were added. The organic layer was separated, washed with 5% potassium carbonate aqueous solution and brine in that order, dried over anhydrous magnesium sulfate, and then concentrated under reduced pressure. The resulting residue was crystallized from chloroform-hexane to give 4-chlorophenyl=3-(4-methoxymethoxy-3-nitrophenyl) propyl=sulfone (42.60 g, 98%).

Mass spectrometry data (m/z): 399 (M$^-$)

Nuclear magnetic resonance spectrum (CDCl$_3$, TMS internal standard)

δ: 2.02–2.08 (2H, m), 2.74 (2H, t, J=7.3 Hz), 3.08 (2H, br-t, J=7.3 Hz), 3.52 (3H, s), 5.26 (2H, s), 7.24 (1H, br-d, J=8.5 Hz), 7.29 (1H, dd, J=8.5, 1.8 Hz), 7.55 (2H, d, J=7.8 Hz), 7.56 (1H, br-s), 7.55 (2H, d, J=7.8 Hz)

(4) 4-Chlorophenyl=3-(4-methoxymethoxy-3-nitrophenyl)propyl=sulfone (42.50 g, 106.29 mmol) was suspended in tetrahydrofuran (200 ml), 6 N hydrochloric acid aqueous solution (200 ml) was added, and the mixture was stirred at room temperature for 2 hours. The reaction solution was concentrated under reduced pressure and the product formed was extracted twice with chloroform. The resulting organic layer was washed with brine, dried over anhydrous magnesium sulfate, and then concentrated under reduced pressure. The resulting residue was crystallized from chloroform-ether to give 4-[3-(4-chlorophenylsulfonyl)propyl]-2-nitrophenol (35.90 g, 95%).

Mass spectrometry data (m/z): 356 (M+1)$^+$

Nuclear magnetic resonance spectrum (CDCl$_3$, TMS internal standard)

δ: 2.02–2.09 (2H, m), 2.74 (2H, br-t, J=7.3 Hz), 3.09 (2H, br-t, J=7.3 Hz), 7.09 (1H, d, J=8.5 Hz), 7.38 (1H, dd, J=8.5, 2.4 Hz), 7.55 (2H, d, J=8.5 Hz), 7.82–7.86 (3H, m), 10.44 (1H, s)

(5) 4-[3-(4-Chlorophenylsulfonyl)propyl]-2-nitrophenol (10.00 g, 28.11 mmol) was dissolved in 1,4-dioxane (100 ml), 4 N hydrochloric acid solution in 1,4-dioxane (8.43 ml, 33.73 mmol) and 10% palladium-carbon (1.0 g) were added, and the mixture was stirred for 4 hours in an atmosphere of hydrogen gas under 1 atmospheric pressure. The crystals precipitated in the reaction solution were dissolved by adding methanol, the reaction mixture was filtered, and then the resulting filtrate was concentrated under reduced pressure. By crystallizing the resulting residue from acetonitrile-ether, 2-amino-4-[3-(4-chlorophenylsulfonyl)propyl]phenol hydrochloride (9.71 g, 95%) was obtained.

Mass spectrometry data (m/z): 326 (M-HCl+1)$^+$

Nuclear magnetic resonance spectrum (DMSO-d$_6$, TMS internal standard)

δ: 1.74–1.80 (2H, m), 2.57 (2H, br-t, J=7.3 Hz), 3.33 (2H, br-t, J=7.3 Hz), 6.99 (2H, s), 7.17 (1H, br-s), 7.75 (2H, d, J=8.5 Hz), 7.75 (2H, d, J=8.5 Hz), 9.33 (2H, br), 10.60 (1H, br-s)

REFERENCE EXAMPLE 2

Thionyl chloride (2 ml) was added to 3-[2-(4-phenyl-2-thiazolyl)vinyl]benzoic acid (0.45 g, 1.46 mmol), the mixture was stirred with heating under reflux for 30 minutes, and then the reaction solution was concentrated under reduced pressure. Toluene was added to the resulting residue, the mixture was concentrated under reduced pressure and, after repeating this step again, dried in vacuo. The resulting residue was added to a mixture of 2-amino-4-[3-(4-chlorophenylsulfonyl)propyl]phenol hydrochloride (0.50 g, 1.38 mmol), pyridine (3 ml) and dichloromethane (2 ml) with stirred under ice-cooling, followed by 12 hours of reaction at room temperature. The reaction solution was poured into ice and 1 N hydrochloric acid and the solid precipitated was collected by filtration. By washing the collected solid with ethanol, 5'-[3-(4-chlorophenylsulfonyl) propyl]-2'-hydroxy-3-[2-(4-phenyl-2-thiazolyl)vinyl] benzanilide (0.79 g, 1.28 mmol, 93%) was obtained as a solid.

Compounds of Reference Examples 3 to 17 were synthesized in the same manner as described in Reference Example 2. Names and physical property values of these compounds are shown in the following Tables 3 to 6.

TABLE 3

| Ref. No. | Compound name | Physicochemical property |
|---|---|---|
| 2 | 5'-[3-(4-chlorophenylsulfonyl)-propyl]-2'-hydroxy-3-[2-(4-phenyl-2-thiazolyl)vinyl]benzanilide | MS :m/Z 615 (M$^+$)<br>NMR δ=(DMSO-d$_6$), 1.78–1.86 (2H, m),<br>2.59 (2H, br-t, J=7.3Hz),<br>3.35 (2H, br-t, J=7.8Hz), 6.86 (2H, s),<br>7.38 (1H, t, J=7.3Hz), 7.46–7.52 (3H, m),<br>7.59 (1H, t, J=7.8Hz), 7.65–7.70 (4H, m),<br>7.91–7.96 (4H, m), 8.05 (2H, d, J=7.3Hz),<br>8.13 (1H, s), 8.41 (1H, br-s), 9.56 (H, br-s),<br>9.67 (1H, br-s) |
| 3 | 5'-[3-(4-chlorophenylsulfonyl)-propyl]-2'-hydroxy-3-[2-[4-(4-methylphenyl)-2-thiazolyl]vinyl]-benzanilide | MS:m/Z 629 (M$^+$)<br>NMR δ=(DMSO-d$_6$), 1.80–1.86 (2H, m), 2.35 (3H, s),<br>2.60 (2H, br-t, J=7.6Hz), 3.33–3.37 (2H, m),<br>6.86 (2H, s), 7.28 (2H, d, J=8.6Hz),<br>7.47 (1H, br-s), 7.54–7.75 (6H, m),<br>7.90-8.04 (6H, m), 8.40 (1H, s), 9.57 (1H, br-s),<br>9.67 (1H, br-s) |
| 4 | 5'-[3-(4-chlorophenylsulfonyl)-propyl]-2'-hydroxy-3-[2-(4-isopropyl-2-thiazolyl)vinyl]-benzanilide | MS:m/Z 581 (M$^+$)<br>NMR δ=(DMSO-d$_6$), 1.28 (6H, d, J=6.8Hz),<br>1.78–1.84 (2H, m), 2.56–2.60 (2H, m),<br>3.06 (1H, sep, J=6.8Hz), 3.32–3.36 (2H, m),<br>6.85 (2H, br-s), 7.27 (1H, br-s), 7.43 (1H, br-s),<br>7.52 (1H, d, J=16.1Hz), 7.54–7.58 (1H, m),<br>7.65 (1H, d, J=16.1Hz), 7.74 (2H, d, J=8.8Hz),<br>7.90–7.92 (4H, m), 8.35 (1H, br-s), 9.64 (1H, br-s) |
| 5 | 5'-[3-(4-chlorophenylsulfonyl)-propyl]-2'-hydroxy-3-[2-(4-tert- | MS:m/Z 595 (M$^+$)<br>NMR δ=(DMSO-d$_6$), 1.39 (9H, s), 1.94–2.02 (2H, m), |

TABLE 3-continued

| Ref. No. | Compound name | Physicochemical property |
|---|---|---|
|  | butyl-2-thiazolyl)vinyl]benzanilide | 2.60 (2H, br-t, J=7.3Hz), 3.00–3.05 (2H, m), 6.84 (1H, dd, J=8.3, 2.0Hz), 6.88 (1H, s), 6.95 (1H, d, J=7.8Hz), 7.19 (1H, d, J=2.0Hz), 7.34 (2H, s), 7.47–7.51 (3H, m), 7.69 (1H, br-d, J=7.8Hz), 7.78 (2H, dd, J=6.3, 2.0Hz), 7.84 (1H, br-d, J=8.3Hz), 8.00 (1H, br-s), 8.49 (1H, br-s), 8.72 (1H, br-s) |
| 6 | 5'-[3-(4-chlorophenylsulfonyl)-propyl]-2'-hydroxy-3-(4-phenyl-2 thiazolylmethoxy)benzanilide | MS:m/Z 619 (M$^+$) NMR δ=(DMSO-d$_6$), 1.76–1.83 (2H, m), 2.56 (2H, br-t, J=7.3Hz), 3.28–3.34 (2H, m), 5.61 (2H, s), 6.83 (2H, s), 7.32–7.37 (2H, m), 7.44–7.51 (4H, m), 7.60 (1H, br-d, J=7.9Hz), 7.72–7.74 (3H, m), 7.90 (2H, dd, J=6.7, 1.8Hz), 7.96 (2H, d, J=7.3Hz), 8.17 (1H, s), 9.53 (1H, br-s), 9.55 (1H, br-s) |

TABLE 4

| Ref. No. | Compound name | Physicochemical property |
|---|---|---|
| 7 | 3-(4-tert-butyl-2-thiazolylmethoxy)-5'-[3-(4-chlorophenylsulfonyl)-propyl]-2'-hydroxybenzanilide | MS:m/Z 599 (M$^+$) NMR δ=(DMSO-d$_6$), 1.31 (9H, s), 1.79–1.85 (2H, m), 2.58 (2H, br-t, J=7.3Hz), 3.33–3.36 (2H, m), 5.51 (2H, s), 6.84 (2H, br-s), 7.29–7.32 (2H, m), 7.46 (1H, br-s), 7.48 (1H, br-t, J=7.8Hz), 7.60 (1H, br-d, J=7.8Hz), 7.72 (1H, br-s), 7.73(2H, d, J=6.8Hz), 7.91 (2H, dd, J=6.8, 2.0Hz), 9.54 (2H, br-s) |
| 8 | 5'-[3-(4-chlorophenylsulfonyl)-propyl]-2'-hydroxy-3-[2-(4-cyclo-propyl-2-thiazolyl)vinyl]benzanilide | MS:m/Z 579 (M$^+$) NMR δ=(DMSO-d$_6$), 0.85–0.95 (4H, m), 1.78–1.85 (2H, m), 2.08–2.13 (1H, m), 2.25 (2H, br-t, J=7.3Hz), 3.36 (2H, br-t, J=7.9Hz), 6.95 (2H, s), 7.27 (1H, s), 7.43 (1H, br-s), 7.49 (1H, d, J=16.2Hz), 7.55 (1H, t, J=7.9Hz), 7.59 (1H, d, J=16.2Hz), 7.74 (2H, dd, J=6.7, 1.8Hz), 7.87–7.92 (4H, m), 8.34 (1H, br-s), 9.53 (1H, br-s), 9.64 (1H, br-s) |
| 9 | 5'-[3-(4-chlorophenylsulfonyl)-propyl]-3-[(4-cyclopropyl-2-thiazolyl)methoxy]-2'-hydroxybenzanilide | MS:m/Z 583 (M$^+$) NMR δ=(DMSO-d$_6$), 0.82–0.93 (4H, m), 1.47–1.84 (2H, m), 2.07–2.12 (1H, m), 2.57 (2H, br-t, J=7.3Hz), 3.33 (2H, br-t, J=7.9Hz), 5.45 (2H, s), 6.83 (2H, s), 7.27 (1H, dd, J=7.9, 2.4Hz), 7.31 (1H, s), 7.44 (1H, br-s), 7.47 (1H, br-t, J=7.9Hz), 7.59 (1H, br-d, J=7.9Hz), 7.65 (1H, br-s), 7.73 (2H, dd, J=8.9, 2.1Hz), 7.90 (2H, dd, J=8.9, 2.1Hz), 9.52 (1H, s), 9.53 (1H, s) |
| 10 | 3-[(4-tert-butyl-2-thiazolyl)methyl-thio]-5'-(3-(4-chlorophenylsulfonyl)-propyl]-2'-hydroxybenzanilide | MS:m/Z 615 (M$^+$) NMR δ=(DMSO-d$_6$), 1.22 (9H, s), 1.77–1.81 (2H, m), 2.56 (br-t, J=7.3Hz), 3.33 (2H, br-t, J=7.6Hz), 4.67 (2H, s), 6.82 (2H, s), 7.13 (1H, s), 7.40 (1H, s), 7.45 (1H, br-t, J=7.8Hz), 7.60 (1H, br-s), 7.73 (2H, dd, J=6.4, 2.0Hz), 7.76 (1H, br-d, (1H, J=9.3Hz), 7.90 (2H, dd, J=6.4, 2.0Hz), 7.98 (1H, br-s), 9.51 (1H, br-s), 9.54 (1H, br-s) |
| 11 | 3-[2-(4-tert-butyl-2-thiazolyl)ethyl]-5'-[3-(4-chlorophenylsulfonyl)-propyl]-2'-hydroxybenzanilide | MS :m/Z 597 (M$^+$) NMR δ=(DMSO-d$_6$), 1.26 (9H, s), 1.76–1.83 (2H, m), 2.57 (2H, br-t, J=7.3Hz), 2.96–3.35 (4H, m), 3,12 (2H, br-t, J=7.3Hz), 6.82 (2H, s), 7.05 (1H, s), 7.40–7.49 (3H, m), 7.73 (2H, br-d, J=8.8Hz), 7.77 (1H, br-d, J=8.8Hz), 7.88–7.91 (3H, m), 9.48 (1H, br-s), 9.55 (1H, br-s) |

TABLE 5

| Ref. No. | Compound name | Physicochemical property |
|---|---|---|
| 12 | 5'-[3-(4-chlorophenylsulfonyl)-propyl]-3-[(4-cyclohexyl-2-thiazolyl)methoxy]-2'-hydroxy-benzanilide | MS:m/Z 625 (M$^+$)<br>NMR δ=(DMSO-d$_6$), 1.17–1.25 (2H, m), 1.31–1.46 (4H, m), 1.66–1.69 (1H, m), 1.74–1.83 (4H, m), 1.87–1.99 (2H, m), 2.67 (2H, br-t, J=7.3Hz), 2.68–2.73 (1H, m), 3.30–3.35 (2H, m), 5.48 (2H, s), 6.82 (2H, s), 7.28–7.30 (1H, m), 7.45–7.49 (2H, m), 7.59 (1H, br-d, J=7.3Hz), 7.66 (1H, br-s), 7.73 (2H, dd, J=8.6, 2.4Hz), 7.90 (2H, dd, J=8.6, 2.4Hz), 9.51 (1H, br-s), 9.54 (1H, s) |
| 13 | 5'-[3-(4-chlorophenylsulfonyl)-propyl]-3-[(4-cyclopentyl-2-thiazolyl)methoxy]-2'-hydroxy-benzanilide | MS:m/Z 611 (M$^+$)<br>NMR δ=(DMSO-d$_6$), 1.60–1.74 (6H, m), 1.76–1.83 (2H, m), 1.96–2.05 (2H, m), 2.57 (2H, br-t, J=7.3Hz), 3.15–3.21 (1H, m), 3.31–3.35 (2H, m), 5.48 (2H, s), 6.83 (2H, s), 7.29 (1H, dd, J=7.9, 2.4Hz), 7.32 (1H, s), 7.44 (1H, br-s), 7.47 (1H, t, J=7.9Hz), 7.59 (1H, br-d, J=7.9Hz), 7.66 (1H, br-s), 7.73 (2H, dd, J=9.2, 2.4Hz), 7.90 (2H, dd, J=9.2, 2.4Hz), 9.51 (1H, s), 9.53 (1H, s) |
| 14 | 5'-[3-(4-chlorophenylsulfonyl)-propyl]-3-[(4-cyclobutyl-2-thiazolyl)methoxy]-2' hydroxybenzanilide | MS:m/Z 597 (M$^+$)<br>NMR δ=(DMSO-d$_6$), 1.75–1.89 (3H, m), 1.92–2.02 (1H, m), 2.18–2.30 (4H, m), 2.56 (2H, t, J=7.3Hz), 3.28–3.34 (2H, m), 3.60–3.67 (1H, m), 5.50 (2H, s), 6.82 (2H, s), 7.29 (1H, dd, J=8.5, 2.4Hz), 7.35 (1H, s), 7.44 (1H, br-d, J=9.2Hz), 7.47 (1H, t, J=7.9Hz), 7.58 (1H, br-d, J=7.9Hz), 7.66 (1H, br-s), 7.73 (2H, d, J=8.6Hz), 7.90 (2H, d, J=8.6Hz), 9.51 (1H, br-s), 9.53 (1H, br-s) |
| 15 | 3-[1-(4-tert-butyl-2-thiazolyl)-ethoxy]-5'-[3-(4-chlorophenyl-sulfonyl)propyl]-2'-hydroxybenz-anilide | MS:m/Z 613 (M$^+$)<br>NMR δ=(CDCl$_3$), 1.33 (9H, s), 1.80 (3H, d, J=6.4Hz), 1.96–2.04 (2H, m), 2.62 (2H, t, J=7.4Hz), 3.01–3.04 (2H, m), 5.78 (1H, q, J=6.4Hz), 6.85–7.01 (3H, m), 7.18–7.22 (1H, m), 7.38 (1H, t, J=8.0Hz), 7.49–7.56 (4H, m), 7.79 (2H, d, J=8.8Hz), 8.33 (1H, br-s) |

TABLE 6

| Ref. No. | Compound name | Physicochemical property |
|---|---|---|
| 16 | 3-[(4-tert-butyl-2-thiazolyl)-methoxy]-5'-[3-(4-chlorophenyl-sulfonyl)propyl]-2'-hydroxy-5-(4-nitrobenzyloxycarbonylamino)benzanilide | MS :m/Z 793 (M$^+$)<br>NMR δ=(DMSO-d$_6$), 1.35 (9H, s), 2.00–2.06 (2H, m), 2.65 (2H, t, J=7.3Hz) 3.02–3.06 (2H, m), 5.3 1 (2H, s), 5.39 (2H, s), 6.88 (1H, dd, J=8.3, 2.4Hz), 6.95 (1H, s), 6.95 (1H, br-d, J=8.3Hz), 7.00 (1H, br-s), 7.05 (1H, br-s), 7.39 (1H, br-s), 7.41 (1H, br-s), 7.52–7.58 (4H, m), 7.81 (2H, dd, J=6.8, 1.9Hz), 8.24 (2H, d, J=8.8Hz), 8.36 (1H, br-s), 8.38 (1H, br-s) |
| 17 | 5'-[3-(4-chlorophenylsulfonyl)-propyl]-3-[2-(4-cyclobutyl-2-thiazolyl)ethyl]-2'-hydroxybenz-anilide | MS:m/Z 595 (M$^+$)<br>NMR δ=(CDCl$_3$), 1.88–1.92 (1H, m), 1.99–2.04 (3H, m), 2.18–2.25 (2H, m), 2.32–2.37 (2H, m), 2.63 (2H, br-t, J=7.3Hz), 3.04 (2H, br-t, J=7.9Hz), 3.17 (2H, br-t, J=7.3Hz), 3.33 (2H, br-t, J=7.3Hz), 3.62–3.66 (1H, m), 6.77 (1H, s), 6.86 (1H, br-d, J=8.6Hz), 6.94 (1H, br-d, J=7.9Hz), 7.13 (1H, s), 7.42 (1H, br-d, J=7.3Hz), 7.52 (2H, br-d, J=8.6Hz), 7.73 (1H, s), 7.74 (1H, br-d, J=7.3Hz), 7.80 (2H, br-d, J=7.9Hz), 8.36 (1H, s), 8.78 (1H, s) |

REFERENCE EXAMPLE 18

3-[2-(4-tert-Butyl-2-thiazolyl)ethyl]-5'-[3-(4-chlorophenylsulfonyl)propyl]-2'-hydroxybenzanilide (0.60 g, 1.0 mmol) was dissolved in DMF (6.0 ml), potassium Compounds of Reference Examples 19 to 21 were synthesized in the same manner as described in Reference Example 18. Names and physical property values of these compounds are shown in the following Tables 7 and 8.

TABLE 7

| Ref. No. | Compound name | Physicochemical property |
|---|---|---|
| 18 | 3-[2-(4-tert-butyl-2-thiazolyl)ethyl]-5'-[3-(4-chlorophenylsulfonyl)propyl]-2'-cyanomethoxybenzanilide | MS:m/Z 636 (M$^+$)<br>NMR δ=(CDCl$_3$), 1.33 (9H, s), 2.01–2.09 (2H, m), 2.72 (2H, t, J=7.3Hz), 3.07–3.1 1 (2H, m), 3.20 (2H, br-t, J=6.8Hz), 3.34 (2H, dd, J=8.8, 6.8Hz), 4.88 (2H, s), 6.72 (1H, s), 6.89 (1H, dd, J=8.8, 1.9Hz), 6.93 (1H, d, J=8.3Hz), 7.41 (2H, d, J=4AHz), 7.53 (2H, d, J=8.3Hz), 7.68 (1H, m), 7.75 (1H, br-s), 7.82 (2H, dd, J=6.8, 1.9Hz), 8.27 (1H, br-s), 8.33 (1H, br-s) |
| 19 | 3-[(4-tert-butyl-2-thiazolyl)methoxy]-5'-[3-(4-chlorophenylsulfonyl)propyl]-2'-cyanomethoxybenzanilide | MS:m/Z 638 (M$^+$)<br>NMR δ=(CDCl$_3$), 1.36 (9H, s), 2.02–2.08 (2H, m), 2.72 (2H, br-t, J=7.3Hz), 3.07–3.11 (2H, m), 4.87 (2H, s), 5.41 (2H, s), 6.88–6.94 (2H, m), 7.22 (1H, dt, J=6.8, 2.4Hz) 7.43–7.45 (2H, m), 7.53 (2H, dd, J=8.8, 1.9Hz), 7.55 (1H, br-s), 7.83 (2H, dd, J=8.8, 1.9Hz), 8.28 (1H, br-s), 8.31 (1H, br-s) |
| 20 | 3-[(4-tert-butyl-2-thiazolyl)methylthiol-5'-[3-(4-chlorophenylsulfonyl)propyl]-2'-cyanomethoxybenzanilide | MS:m/Z 654 (M$^+$)<br>NMR δ=(CDCl$_3$), 1.29 (9H, br-s), 2.01–2.09 (2H, m), 2.72 (1H, t, J=7.3Hz), 3.09 (2H, t, 7.8Hz), 4.48 (2H, s), 4.87 (2H, s), 6.80 (1H, s), 6.91–6.95 (2H, m), 7.40 (1H, t, J=7.8Hz), 7.53–7.57 (3H, m), 7.66 (1H, d, J=7.8Hz), 7.83 (2H, d, J=8.8Hz), 7.89 (1H, s), 8.24 (1H, s), 8.30 (1H, s) |

TABLE 8

| Ref. No. | Compound name | Physicochemical property |
|---|---|---|
| 21 | 3-[2-(4-cyclobutyl-2-thiazolyl)-ethyl]-5'-[3-(4-chlorophenylsulfonyl)propyl]-2'-cyanomethoxybenzanilide | MS:m/Z 634 (M$^+$)<br>NMR δ=(CDCl$_3$), 1.89–1.93 (1H, m), 1.99–2.90 (3H, m), 2.19–2.27 (2H, m), 2.33–2.38 (2H, m), 2.72 (2H, t, J=7.3Hz), 3.09 (2H, br-t, J=7.3Hz), 3.20 (2H, br-t, J=7.9Hz), 3.34 (2H, br-t, J=7.9Hz), 3.63–3.66 (1H, m), 6.76 (1H, s), 6.89–6.94 (3H, m), 7.42–7.45 (2H, m), 7.54 (2H, d, J=8.0Hz), 7.68–7.69 (1H, m), 7.75 (1H, s), 7.83 (2H, d, 3=8.6Hz), 8.27 (1H, s), 8.33 (1H, s) | carbonate (0.21 g, 1.5 mmol), a catalytically effective amount of tetrabutylammonium bromide and bromoacetonitrile (0.080 ml, 1.2 mmol) were added to the solution in that order under ice-cooling, followed by 12 hours of stirring at room temperature. Ice-water was added to the reaction solution and the product formed was extracted with a benzene-ethyl acetate (1:1) mixed solution. The resulting organic layer was washed with 5% potassium carbonate aqueous solution and brine in that order, dried over anhydrous magnesium sulfate, and then concentrated under reduced pressure. The resulting residue was purified by silica gel column chromatography (eluent=chloroform) and crystallized from acetonitrile, thereby obtaining 3-[2-(4-tert-butyl-2-thiazolyl)ethyl]-5'-[3-(4-chlorophenylsulfonyl) propyl]-2'-cyanomethoxybenzanilide (0.60 g, 0.94 mmol, 94%) as colorless crystals.

REFERENCE EXAMPLE 22

N-(2-Hydroxyethyl)phthalimide (970 mg, 5.1 mmol) and triphenylphosphine (1.3 g, 5.1 mmol) were added in that order to a solution of 4-[3-(4-chlorophenylsulfonyl)propyl]-2-nitrophenol (1.5 g, 4.2 mmol) in anhydrous tetrahydrofuran (30 ml) under ice-cooling, and diethyl azodicarboxylate (800 μl, 5.1 mmol) was added dropwise to the mixture. The reaction solution was stirred overnight under ice-cooling and then concentrated. The resulting residue was purified by silica gel column chromatography (eluent=chloroform:ethyl acetate=20:1) and crystallized using chloroform-ether, thereby obtaining N-[2-[4-[3-(4-chlorophenylsulfonyl) propyl]- 2-nitrophenoxy]ethyl]phthalimide (2.1 g, 4.1 mmol, 96%) as white crystals.

Mass spectrometry data (m/z): 529 (M$^+$)

Nuclear magnetic resonance spectrum (CDCl$_3$, TMS internal standard)

δ: 1.99–2.06 (2H, m), 2.71 (2H, br-t, J=7.6 Hz), 3.04 (2H, br-t, J=7.6 Hz), 4.15 (2H, t, J=6.1 Hz), 4.37 (2H, t, J=6.1 Hz), 7.02 (1H, d, J=8.5 Hz), 7.29 (1H, d, J=8.6 Hz), 7.54 (1H, s), 7.54 (2H, d, J=8.5 Hz), 7.72–7.75 (2H, m), 7.81 (2H, d, J=8.5 Hz), 7.86–7.90 (2H, m)

REFERENCE EXAMPLE 23

4 N Hydrochloric acid/dioxane (1.2 ml) and 10% Pd—C were added in that order to a mixture of 2-[4-[3-(4-chlorophenylsulfonyl)propyl]-2-nitrophenoxy]ethylphthalimide (2.1 g, 3.9 mmol), ethanol (20 ml) and dioxane (20 ml), and the resulting mixture was stirred at room temperature in an atmosphere of hydrogen. After 4 hours of the stirring, the reaction solution was filtered through celite, the resulting filtrate was concentrated, and then the resulting residue was crystallized from chloroform-ethanol to give N-[2-[2-amino-4-[3-(4-chlorophenylsulfonyl)propyl]phenoxy]ethyl]phthalimide hydrochloride (1.4 g, 2.6 mmol, 66%) as white crystals.

Mass spectrometry data (m/z): 499 (M$^+$)

Nuclear magnetic resonance spectrum (CDCl$_3$, TMS internal standard)

δ: 1.98–2.05 (2H, m), 2.61–2.73 (2H, m), 3.03 (2H, t, J=7.8 Hz), 4.15–4.17 (2H, m), 4.23–4.24 (2H, m), 6.74–6.82 (2H, m), 7.50 (1H, d, J=8.3 Hz), 7.53–7.55 (1H, m), 7.71–7.75 (2H, m), 7.82 (2H, d, J=8.3 Hz), 7.84–7.89 (2H, m)

The following compound was synthesized in the same manner as described in Reference Example 2.

REFERENCE EXAMPLE 24

N-[2-[2-[3-[(4-tert-butyl-2-thiazolyl)methoxy]benzoylamino]-4-[3-(4-chlorophenylsulfonyl)propyl]phenoxy]ethyl]phthalimide Mass spectrometry data (m/z): 772 (M$^+$)

Nuclear magnetic resonance spectrum (CDCl$_3$, TMS internal standard)

δ: 1.35 (9H, s), 1.98–2.03 (2H, m), 2.65 (2H, t, J=7.3 Hz), 3.03–3.07 (2H, m), 4.19–4.24 (4H, m), 5.50 (2H, s), 6.73–6.79 (2H, m), 6.93 (1H, s), 7.49–7.54 (3H, m), 7.63–7.71 (7H, m), 7.80 (2H, d, J=8.8 Hz), 8.27 (1H, s), 8.58 (1H, s)

REFERENCE EXAMPLE 25

(1) With cooling at –30° C. or below, thionyl chloride (75 ml) was added dropwise to methanol (150 ml). At –30° C., 3-(4-hydroxy-3-nitrophenyl)propionic acid (26.20 g, 0.12 mol) was added to this solution. The reaction solution was stirred at room temperature for 1 hour and then at 40 to 50° C. for 3 hours. The reaction solution was concentrated under reduced pressure. Then, a procedure of adding toluene (100 ml) to the residue and concentrating the mixture under reduced pressure was repeated twice. Thereafter, the resulting residue was crystallized from ether-hexane to give methyl 3-(4-hydroxy-3-nitrophenyl)propionate (26.20 g, 94%).

(2) Methyl 3-(4-hydroxy-3-nitrophenyl)propionate (26.10 g, 0.12 mol) was dissolved in dichloromethane (260 ml), and diisopropylethylamine (24.23 ml, 0.14 mol) was added under ice-cooling. Then, chloromethyl methyl ether (9.68 ml, 0.13 mol) was added dropwise to the reaction solution at the same temperature. The reaction solution was subjected to 4 hours of reaction at room temperature. Then, water (200 ml) was added and the mixture was stirred vigorously. The organic layer was separated, washed with 5% potassium carbonate aqueous solution and brine in that order, dried over anhydrous magnesium sulfate, and then concentrated under reduced pressure, thereby obtaining an oily material (31.20 g). This compound was used in the following reaction without purification.

Spending 1 hour, methanol (89.14 ml) was added dropwise to a mixed solution of the just obtained oily material (30.00 g, 0.11 mol), sodium borohydride (8.43 g, 0.22 mol) and tetrahydrofuran (446 ml) with keeping the temperature at 50 to 60° C. The reaction solution was stirred at the same temperature for 30 minutes and then concentrated under reduced pressure. Ice-water was added to the resulting residue and the product formed was extracted three times with chloroform. The organic layer was washed with 5% potassium carbonate aqueous solution and brine in that order, dried over anhydrous magnesium sulfate, and then concentrated under reduced pressure, thereby obtaining 3-(4-methoxymethoxy-3-nitrophenyl)propanol (26.00 g, 97%) as an oily material.

(3) 3-(4-Methoxymethoxy-3-nitrophenyl)propanol (26.8 g, 0.11 mol) was dissolved in dichloromethane (270 ml), and triethylamine (18.58 ml, 0.13 mol) was added to the solution with stirred under ice-cooling. Under ice-cooling and spending 2 hours, methanesulfonyl chloride (9.03 ml, 0.12 mol) which had been dissolved in dichloromethane (27 ml) was added dropwise to this solution. The reaction solution was stirred at room temperature for 30 minutes and ice and 10% citric acid aqueous solution were added. Thereafter, the organic layer was separated, washed with saturated sodium bicarbonate aqueous solution and brine in that order, dried over anhydrous magnesium sulfate, and then concentrated under reduced pressure to give 3-(4-methoxymethoxy-3-nitrophenyl)propyl=methylsulfonate (35.10 g, 99%).

REFERENCE EXAMPLE 26

At –78° C., oxalyl chloride (135 mg, 1.06 mmol) was added to a mixture of 4-[2-(2-benzothiazolyl)vinyl]benzoic acid (247 mg, 0.88 mmol), dimethylformamide (one drop) and dichloromethane (10 ml), and the resulting mixture was stirred at room temperature for 2 hours and then concentrated under reduced pressure. Under ice-cooling, the resulting compound was gradually added to a mixture of 2-amino-4-[3-(4-chlorophenylsulfonyl)propyl]phenol hydrochloride (320 mg, 0.88 mmol), pyridine (3 ml) and dichloromethane (10 ml), and the resulting mixture was stirred at room temperature for 12 hours. The reaction solution was concentrated under reduced pressure, water was added to the resulting residue, and the mixture was heated until reflux and then cooled. Then, the solid material formed was collected by filtration and dried under reduced pressure. Ethanol (10 ml) was added to the resulting solid material, and the mixture was heated until reflux and then cooled. The crystals formed were collected by filtration and dried under reduced pressure to give 4-[2-(2-benzothiazolyl)vinyl]-5'-[3-(4-chlorophenylsulfonyl)propyl]-2'-hydroxybenzanilide (335 mg, 0.57 mmol, 65%) as colorless crystals.

The following compounds of Reference Examples 27 to 36 were synthesized in the same manner as described in Reference Example 26. Names and physical property values of these compounds are shown in the following Tables 9 to 11.

TABLE 9

| Ref. No. | Compound name | Physicochemical property |
| --- | --- | --- |
| 26 | 4-[2-(2-benzothiazolyl)vinyl]-5'-[3-(4-chlorophenylsulfonyl)propyl]-2'-hydroxybenzanilide | MS: (m/z) 589 (M$^+$)<br>NMR (DMSO-d$_6$)<br>δ: 1.77–1.83 (2H, m), 2.57 (2H, t, J=7.5Hz), 3.29–3.35 (2H, m), 6.83 (2H, br), 7.72–7.78 (4H, m), 7.88–8.10 (8H, m), 8.13 (1H, d, J=8.0Hz), 9.57 (1H, br) |
| 27 | 3-(2-benzothiazolylmethoxy)-5'-[3-(4-chlorophenylsulfonyl)propyl]-2'-hydroxybenzanilide | MS: (m/z) 593 (M$^+$)<br>NMR (DMSO-d$_6$)<br>δ: 1.75–1.82 (2H, m), 2.56 (2H, t, J=7.4Hz), 3.31–3.35 (2H, m), 5.71 (2H, s), 6.82 (2H, br), 7.32–7.35 (1H, m), 7.43–7.62 (5H, m), 7.69–7.74 (3H, m), 7.89 (2H, d, J=8.4Hz), 8.03 (1H, d, J=8.0Hz), 8.13 (1H, d, J=7.6Hz), 9.52–9.54 (2H, m) |
| 28 | 3-[2-(2-benzothiazolyl)vinyl]-5'-[3-(4-chlorophenylsulfonyl)propyl]-2'-hydroxybenzanilide | MS: (m/z) 589 (M$^+$)<br>NMR (DMSO-d$_6$)<br>δ: 1.69–1.75 (2H, m), 2.58 (2H, t, J=7.7Hz), 3.32–3.36 (2H, m), 6.85 (2H, br), 7.43–8.40 (15H, m), 9.55–9.56 (2H, m) |
| 29 | 3-[(2-benzothiazolyl)thiomethyl]-5'-[3-(4-chlorophenylsulfonyl)propyl]-2'-hydroxybenzanilide | MS: (m/z) 609 (M$^+$)<br>NMR (DMSO-d$_6$)<br>δ: 1.74–1.83 (2H, m), 2.56 (2H, t, J=7.4Hz), 3.32–3.35 (2H, m) 4.75 (2H, s), 6.82 (2H, br), 7.35–7.39 (1H, m), 7.46–7.54 (3H, m), 7.71–7.76 (3H, m), 7.86–7.93 (4H, m), 8.01 (1H, d, J=8.0Hz), 8.12 (1H, br), 9.49 (1H, br), 9.57–9.59 (1H, m) |

TABLE 10

| Ref. No. | Compound name | Physicochemical property |
| --- | --- | --- |
| 30 | 3-[2-(5-chloro-2-(2-benzothiazolyl)vinyl]-5'-[3-(4-chlorophenylsulfonyl)propyl]-2'-hydroxybenzanilide | MS: (m/z) 623 (M$^+$)<br>NMR (DMSO-d$_6$)<br>δ: 1.78–1.84 (2H, m), 2.58 (2H, t, J=7.5Hz), 3.33–3.36 (2H, m), 6.82 (2H, br), 7.43–8.41 (14H, m), 9.55–9.57 (1H, m), 9.64 (1H, br) |
| 31 | 3-(2-benzoxazolylmethoxy)-5'-[3-(4 chlorophenylsulfonyl)propyl]-2' hydroxybenzanilide | MS: (m/z) 577 (M$^+$)<br>NMR (DMSO-d$_6$)<br>δ: 1.73–1.82 (2H, m), 2.57 (2H, t, J=7.6Hz), 3.31–3.35 (2H, m), 5.58 (2H, s), 6.83 (2H, br), 7.23–7.90 (13H, m), 9.50 (1H, br), 9.55–9.57 (1H, m) |
| 32 | 3-(5-chloro-2-benzothiazolylmethoxy)-5'-[3-(4-chlorophenylsulfonyl)propyl]-2'-hydroxybenzanilide | MS: (m/z) 627 (M$^+$)<br>NMR (DMSO-d$_6$)<br>δ: 1.76–1.83 (2H, m), 2.57 (214, t, J=7.5Hz), 3.30–3.34 (2H, m), 5.72 (2H, s), 6.83 (2H, br), 7.32–7.36 (1H, m), 7.42–7.55 (2H, m), 7.58–7.62 (1H, m), 7.69 (1H, br), 7.73 (2H, d, J=8.5Hz), 7.90 (2H, d, J=8.5Hz), 8.13 (1H, br), 8.16–8.19 (1H, m), 9.52–9.55 (2H, m) |
| 33 | 5'-[3-(4-chlorophenylsulfonyl)propyl]-3-(5-trifluoromethyl-2-benzothiazolylmethoxy)-2'-hydroxybenzanilide | MS: (m/z) 661 (M$^+$)<br>NMR (DMSO-d$_6$)<br>δ: 1.77–1.83 (2H, m), 2.57 (2H, t, J=7.8Hz), 3.31–3.34 (2H, m), 5.77 (2H, s), 6.83 (2H, br), 7.35 (1H, dd, J=8.8, 2.3Hz), 7.44–7.46 (1H, m), 7.50 (1H, t, J=8.0Hz), 7.62 (1H, d, J=8.0Hz), 7.66–7.74 (3H, m), 7.80–7.82 (1H, m), 7.90 (2H, d, J=8.5Hz), 8.40–8.42 (2H, m), 9.52–9.56 (2H, m) |

TABLE 11

| Ref. No. | Compound name | Physicochemical property |
| --- | --- | --- |
| 34 | 3-(6-chloro-2-benzothiazolylmethoxy)-5'-[3-(4-chlorophenylsulfonyl)propyl]-2'-hydroxybenzanilide | MS: (m/z) 627 (M$^+$)<br>NMR (DMSO-d$_6$)<br>δ: 1.77–1.83 (2H, m), 2.56 (2H, t, J=7.5Hz), 3.31–3.42 (2H, m), 5.71 (2H, s), 6.30 (2H, br), 7.34 (1H, dd, J=8.0, 2.0Hz), 7.44 (1H, br), 7.50 (1H, t, J=8.0Hz), 7.57–7.62 (2H, m), 7.69–7.74 (3H, m), 7.90 (2H, d, J=8.5Hz), 8.03 (1H, d, J=9.0Hz), 8.30 (1H, d, J=2.0Hz), 9.52 (1H, br), 9.54 (1H, br) |
| 35 | 3-[2-(2-benzothiazolyl)ethyl]-5'-[3-(4-chlorophenylsulfonyl)propyl]-2'-hydroxy-benzanilide | MS: (m/z) 59 1 (M$^+$)<br>NMR (DMSO-d$_6$)<br>δ: 1.76–1.82 (2H, m), 2.56 (2H, t, J=8.3Hz), 3.24–3.43 (4H, m), 3.51 (2H, t, J=7.8Hz), 6.82 (2H, br), 7.38–7.54 (4H, m), 7.73 (2H, d, J=8.0Hz), 7.79 (1H, d, J=8.0Hz), 7.87–7.90 (3H, m), 7.94–7.95 (2H, m), 8.04 (1H, d, J=8.0Hz), 9.48 (1H, br), 9.55 (1H, br) |
| 36 | 3-[(2-benzothiazolyl)methylthio]-5'-[3-(4-chlorophenylsulfonyl)propyl]-2'-hydroxy-benzanilide | MS: (m/z) 609 (M$^+$)<br>NMR (DMSO-d$_6$)<br>δ: 1.70–1.85 (2H, m), 2.50–2.63 (2H, m), 3.30–3.40 (2H, m), 4.87 (2H, s), 6.82 (2H, s), 7.35–8.20 (9H, m), |

| Ref. No. | Compound name | Physicochemical property |
|---|---|---|
| | | 7.72 (2H, d, J=8.5Hz), 7.90 (2H, d, J=8.6Hz), 9.51 (1H, br-s), 9.55 (1H, br-s) |

REFERENCE EXAMPLE 37

A mixture of 4-tert-butyl-2-(hydroxymethyl)thiazole (441 mg, 2.57 mmol), potassium-tert-butoxide (580 mg, 5.17 mmol), tricaprylmethylamminium chloride (100 mg) and methyl 6-chloropyridine-2-carboxylate (660 mg, 3.85 mmol) was stirred at 120° C. for 2 hours. Water was added to the reaction solution and the product formed was extracted with ethyl acetate. The extract was washed with water and brine in that order, dried over anhydrous sodium sulfate, and then concentrated under reduced pressure. The resulting residue was purified by silica gel column chromatography (eluent =hexane:ethyl acetate=20:1 to 10:1) to give methyl 6-(4-tert-butyl-2-thiazolylmethoxy)pyridine-2-carboxylate (198 mg, 0.65 mmol, 25%).

Nuclear magnetic resonance spectrum (CDCl$_3$, TMS internal standard)

δ: 1.36 (9H, s), 3.96 (3H, s), 5.75 (2H, s), 6.89 (1H, s), 6.98–7.09 (1H, m), 7.71–7.78 (2H, m)

REFERENCE EXAMPLE 38

4-[3-(4-Chlorobenzenesulfonyl)propyl]-2-aminophenol hydrochloride (2.0 g, 5.52 mmol) was suspended in dichloromethane (20 ml), and pyridine (1.79 ml, 22.08 mmol) and acetic anhydride (1.00 ml, 13.80 mmol) were added in that order with stirring under ice-cooling. The reaction solution was stirred at room temperature for 12 hours, and then ice and 5% sodium hydrogensulfate aqueous solution were added. The organic layer was separated and the water layer was further extracted with dichloromethane. The organic layers were combined, washed with 5% sodium hydrogensulfate aqueous solution, 5% potassium carbonate aqueous solution and brine in that order, dried over anhydrous magnesium sulfate, and then concentrated under reduced pressure. The resulting residue was dissolved in tetrahydrofuran (20 ml) and methanol (20 ml), 1 N sodium hydroxide aqueous solution (6.62 ml) was added to the solution, and the mixture was subjected to 2 hours of reaction at room temperature. The reaction solution was acidified by adding ice and 5% sodium hydrogensulfate, and then the mixture was extracted with chloroform. The resulting organic layer was washed with brine, dried over anhydrous magnesium sulfate, and then concentrated under reduced pressure. By crystallizing the resulting residue from chloroform-diethyl ether, 5-[3-(4-chlorobenzenesulfonyl)propyl]-2-hydroxyacetanilide (1.69 g, 83%) was obtained as colorless crystals.

Nuclear magnetic resonance spectrum (CDCl$_3$, TMS internal standard)

δ: 1.67–2.14 (2H, m), 2.14 (3H, s), 2.48–2.64 (2H, m), 3.07–3.30 (2H, m), 6.60–6.90 (2H, m), 7.40 (1H, br-s), 7.61 (2H, br-d, J=8.5 Hz), 7.86 (2H, br-d, J=8.5 Hz), 9.20–9.40 (1H, br), 9.30–9.60 (1H, br)

REFERENCE EXAMPLE 39

Dimethylformamide (10 ml) was added to a mixture of 5-[3-(4-chlorobenzenesulfonyl)propyl]-2-hydroxyacetanilide (1.00 g, 2.72 mmol) and N-chlorosuccinimide (0.44 g, 3.26 mmol), and the solution was subjected to the reaction at 50° C. for 1 hour and then at 80° C. for 2 hours. Ice and water were added to the reaction solution and the mixture was extracted with ethyl acetate. The resulting organic layer was washed with water and brine in that order, dried over anhydrous magnesium sulfate, and then concentrated under reduced pressure. 2-Propanol (10 ml) and 3 N hydrochloric acid (10 ml) were added to the resulting residue, and the solution was heated under reflux for 6 hours. The reaction solution was cooled and then concentrated under reduced pressure. By crystallizing the resulting residue from acetonitrile, 6-chloro-4-[3-(4-chlorobenzenesulfonyl)propyl]-2-aminophenol hydrochloride (0.47 g, 44%) was obtained as a white solid.

Nuclear magnetic resonance spectrum (DMSO-d$_6$, TMS internal standard)

δ: 1.60–1.90 (2H, m), 2.40–2.80 (2H, m), 3.15–3.50 (2H, m), 6.90–7.30 (2H, m), 7.72 (2H, br-d, J=8.8 Hz), 7.91 (2H, br-d, J=8.8 Hz)

REFERENCE EXAMPLE 40

Dimethylformamide (25 ml) was added to a mixture of 5-[3-(4-chlorobenzenesulfonyl)propyl]-2-hydroxyacetanilide (1.65 g, 4.49 mmol) and N-chlorosuccinimide (1.32 g, 9.88 mmol), and the solution was subjected to the reaction at 50° C. for 1 hour and then at 80° C. for 1 hour. Ice and water were added to the reaction solution and the mixture was extracted with ethyl acetate. The resulting organic layer was washed with water and brine in that order, dried over anhydrous magnesium sulfate, and then concentrated under reduced pressure. The resulting residue was crystallized from chloroform to give a white solid (0.95 g). Then, 2-propanol (30 ml) and 3 N hydrochloric acid (30 ml) were added to the white solid (0.90 g), and the mixture prepared was heated under reflux for 3 hours. The reaction solution was cooled and then concentrated under reduced pressure. By crystallizing the resulting residue from acetonitrile, 4-[3-(4-chlorobenzenesulfonyl)propyl]-5,6-dichloro-2-aminophenol hydrochloride (0.75 g, 38%) was obtained as a white solid.

Nuclear magnetic resonance spectrum (DMSO-d$_6$, TMS internal standard)

δ: 1.60–1.90 (2H, m), 2.40–2.80 (2H, m), 3.15–3.50 (2H, m), 6.90–7.30 (2H, m), 7.72 (2H, br-d, J=8.8 Hz), 7.91 (2H, br-d, J=8.8 Hz)

REFERENCE EXAMPLE 41

After a mixture of 2-bromocyclohexanone (865 mg, 4.9 mmol), methyl 3-(thiocarbamoylmethoxy)benzoate (1.00 g, 4.4 mmol) and 1,4-dioxane (10 ml) was stirred at room temperature for 5 hours and then at 80° C. for 12 hours, it was cooled and concentrated under reduced pressure. Saturated sodium bicarbonate aqueous solution was added to the resulting residue and the product formed was extracted with ethyl acetate. The extract was washed with water and brine in that order, dried over anhydrous sodium sulfate, and then concentrated under reduced pressure. Thereafter, the resulting residue was purified by silica gel column chromatography (eluent=hexane:ethyl acetate=4:1) to give methyl 3-(4,5,6,7-tetrahydrobenzothiazol-2-ylmethoxy)benzoate (369 mg, 1.2 mmol, 27%).

Nuclear magnetic resonance spectrum (CDCl$_3$, TMS internal standard)

δ: 1.84–1.89 (4H, m), 2.73–2.80 (4H, m), 3.91 (3H, s), 5.76 (2H, s), 7.18–7.20 (1H, m), 7.36 (1H, t, J=8.0 Hz), 7.66–7.68 (2H, m)

REFERENCE EXAMPLE 42

A mixture of methyl 3-(4,5,6,7-tetrahydrobenzothiazol-2-ylmethoxy)benzoate (361 mg, 1.2 mmol), tetrahydrofuran (2 ml), methanol (2 ml) and 1 N sodium hydroxide (2 ml) was stirred at room temperature for 12 hours and then concentrated under reduced pressure. The resulting residue was dissolved in water and the solution was adjusted to pH 3 by adding 10% citric acid aqueous solution. Thereafter, the solid substance formed was collected by filtration, washed with water, and then dried under reduced pressure to give 3-(4,5,6,7-tetrahydrobenzothiazol-2-ylmethoxy)benzoic acid (257 mg, 0.89 mmol, 75%).

Nuclear magnetic resonance spectrum (DMSO-d$_6$, TMS internal standard)

δ: 1.74–1.82 (4H, m), 2.67–2.78 (4H, m), 5.39 (2H, s), 7.29 (1H, d, J=8.0 Hz), 7.44 (1H, t, J=8.0 Hz), 7.53–7.58 (2H, m), 13.0 (1H, s)

The following compounds of Reference Examples 43 to 50 were obtained in the same manner as described in Reference Example 42.

REFERENCE EXAMPLE 43

6-(4-tert-Butyl-2-thiazolylmethoxy)pyridine-2-carboxylic acid

Nuclear magnetic resonance spectrum (CDCl$_3$, TMS internal standard)

δ: 1.35 (9H, s), 5.68 (2H, s), 6.93 (1H, s), 7.08–7.18 (1H, m), 7.82–7.88 (2H, m)

REFERENCE EXAMPLE 44

3-[(4-tert-Butyl-2-thiazolyl)methoxy]-5-chlorobenzoic acid

Nuclear magnetic resonance spectrum (DMSO-d$_6$, TMS internal standard)

δ: 1.37 (9H, s), 5.42 (2H, s), 6.95 (1H, s), 7.29 (1H, br-t, J=2.0 Hz), 7.64–7.74 (2H, m), 9.10–9.60 (1H, br)

REFERENCE EXAMPLE 45

5-[(4-tert-Butyl-2-thiazolyl)methoxy]-2-chlorobenzoic acid

Mass spectrometry data (m/z): 326 [(M+H)$^+$]

Nuclear magnetic resonance spectrum (DMSO-d$_6$, TMS internal standard)

δ: 1.30 (9H, s), 5.45 (2H, s), 7.23 (1H, dd, J=8.8, 3.4 Hz), 7.31 (1H, s), 7.45–7.48 (2H, m), 13.43 (1H, s)

REFERENCE EXAMPLE 46

3-[(4-tert-Butyl-2-thiazolyl)methoxy]-4-methoxybenzoic acid

Mass spectrometry data (m/z): 322 (M$^+$)

Nuclear magnetic resonance spectrum (DMSO-d$_6$, TMS internal standard)

δ: 1.30 (9H, s), 3.86 (3H, s), 5.41 (2H, s), 7.09 (1H, d, J=8.3 Hz), 7.29 (1H, s), 7.61 (1H, d, J=8.3 Hz), 7.62 (1H, s), 12.64 (1H, s)

REFERENCE EXAMPLE 47

3-[(4-tert-Butyl-2-thiazolyl)methoxy]-4-chlorobenzoic acid

Mass spectrometry data (m/z): 326 [(M+H)$^+$]

Nuclear magnetic resonance spectrum (DMSO-d$_6$, TMS internal standard)

δ: 1.30 (9H, s), 5.59 (2H, s), 7.32 (1H, s), 7.55–7.61 (2H, m), 7.81 (1H, d, J=1.5 Hz), 13.18 (1H, s)

REFERENCE EXAMPLE 48

3-[(4-tert-Butyl-2-thiazolyl)methoxy]-4-methylbenzoic acid

Mass spectrometry data (m/z): 306 (M$^+$)

Nuclear magnetic resonance spectrum (DMSO-d$_6$, TMS internal standard)

δ: 1.30 (9H, s), 2.28 (3H, s), 5.48 (2H, s), 7.29 (1H, s), 7.30 (1H, d, J=8.3 Hz), 7.50 (1H, d, J=8.3 Hz), 7.60 (1H, s), 12.80 (1H, s)

REFERENCE EXAMPLE 49

3-[(4-tert-Butyl-2-thiazolyl)methoxy]-4-nitrobenzoic acid

Mass spectrometry data (m/z): 337 (M$^+$)

Nuclear magnetic resonance spectrum (DMSO-d$_6$, TMS internal standard)

δ: 1.29 (9H, s), 5.69 (2H, s), 7.33 (1H, s), 7.68 (1H, dd, J=8.3, 1.5 Hz), 7.99 (1H, br-d, J=8.3 Hz), 8.00 (1H, s), 13.62 (1H, s)

REFERENCE EXAMPLE 50

3-[(4-tert-Butyl-5-methyl-2-thiazolyl)methoxy]benzoic acid

Mass spectrometry data (m/z): 306 [(M+H)$^+$]

Nuclear magnetic resonance spectrum (DMSO-d$_6$, TMS internal standard)

δ: 1.35 (9H, s), 2.47 (3H, s), 5.34 (2H, s), 7.28 (1H, br-d, J=8.3 Hz), 7.43 (1H, t, J=8.3 Hz), 7.56 (1H, br-d, J=8.3 Hz), 7.57 (1H, br-s), 13.0 (1H, s)

The following compounds of Reference Examples 51 to 58 were obtained in the same manner as described in Reference Example 41

REFERENCE EXAMPLE 51

Methyl 3-[(4-tert-butyl-2-thiazolyl)methoxy]-5-chlorobenzoate

Nuclear magnetic resonance spectrum (CDCl$_3$, TMS internal standard)

δ: 1.36 (9H, s), 3.91 (3H, s), 5.37 (2H, s), 6.93 (1H, s), 7.23 (1H, br-t, J=2.0 Hz), 7.56–7.67 (2H, m)

REFERENCE EXAMPLE 52

Methyl 5-[(4-tert-butyl-2-thiazolyl)methoxy]-2-chlorobenzoate

Nuclear magnetic resonance spectrum (CDCl$_3$, TMS internal standard)

δ: 1.35 (9H, s), 3.92 (3H, s), 5.35 (2H, s), 6.93 (1H, s), 7.08 (1H, dd, J=8.8, 2.9 Hz), 7.35 (1H, d, J=8.8 Hz), 7.51 (1H, d, J=2.9 Hz)

REFERENCE EXAMPLE 53

Methyl 3-[(4-tert-butyl-2-thiazolyl)methoxy]-4-methoxybenzoate

Nuclear magnetic resonance spectrum (CDCl₃, TMS internal standard)

δ: 1.35 (9H, s), 3.86 (3H, s), 3.93 (3H, s), 5.44 (2H, s), 6.91 (1H, d, J=8.3 Hz), 7.71 (1H, d, J=2.0 Hz), 7.72 (2H, br-d, J=8.3 Hz)

REFERENCE EXAMPLE 54

Methyl 3-[(4-tert-butyl-2-thiazolyl)methoxy]-4-chlorobenzoate

Nuclear magnetic resonance spectrum (CDCl₃, TMS internal standard)

δ: 1.36 (9H, s), 3.90 (3H, s), 5.47 (2H, s), 6.94 (1H, s), 7.45 (1H, d, J=8.3 Hz), 7.63 (1H, dd, J=8.3, 2.0 Hz), 7.77 (1H, d, J=2.0 Hz)

REFERENCE EXAMPLE 55

Methyl 3-[(4-tert-butyl-2-thiazolyl)methoxy]-4-methylbenzoate

Nuclear magnetic resonance spectrum (CDCl₃, TMS internal standard)

δ: 1.36 (9H, s), 2.35 (3H, s), 3.89 (3H, s), 5.40 (2H, s), 6.91 (1H, s), 7.22 (1H, d, J=7.3 Hz), 7.60–7.62 (2H, m)

REFERENCE EXAMPLE 56

Methyl 3-[(4-tert-butyl-2-thiazolyl)methoxy]-4-nitrobenzoate

Nuclear magnetic resonance spectrum (CDCl₃, TMS internal standard)

δ: 1.35 (9H, s), 3.95 (3H, s), 5.54 (2H, s), 6.96 (1H, s), 7.74 (1H, dd, J=8.3, 1.5 Hz), 7.86 (1H, d, J=8.3 Hz), 7.99 (1H, d, J=1.5 Hz)

REFERENCE EXAMPLE 57

Methyl 3-[(4-tert-butyl-5-methyl-2-thiazolyl)methoxy]benzoate

Nuclear magnetic resonance spectrum (CDCl₃, TMS internal standard)

δ: 1.38 (9H, s), 2.50 (3H, s), 3.91 (3H, s), 5.27 (2H, s), 7.23–7.45 (2H, m), 7.63–7.72 (2H, m)

REFERENCE EXAMPLE 58

Methyl 3-[2-(4-tert-butyl-2-thiazolyl)ethoxy]benzoate hydrobromide

Nuclear magnetic resonance spectrum (DMSO-d₆, TMS internal standard)

δ: 1.28 (9H, s), 3.39–3.57 (2H, m), 4.40 (2H, t, J=6.3 Hz), 7.18 (1H, s), 7.23–7.62 (4H, m)

REFERENCE EXAMPLE 59

A mixture of methyl 3-[2-(4-tert-butyl-2-thiazolyl) ethoxy]benzoate hydrobromide (102 mg, 0.25 mmol), methanol (1 ml) and 6 N hydrochloric acid (0.5 ml) was stirred at 60° C. for 2 hours, 6 N hydrochloric acid (1 ml) was added, and the mixture was and stirred at 110° C. for 2 hours. The reaction solution was cooled and concentrated under reduced pressure. The resulting solid material was collected by filtration and washed with acetonitrile and diethyl ether in that order to give 3-[2-(4-tert-butyl-2-thiazolyl)ethoxy]benzoic acid hydrochloride (69 mg, 0.20 mmol, 80%).

Nuclear magnetic resonance spectrum (DMSO-d₆, TMS internal standard)

δ: 1.30 (9H, s), 3.53 (2H, t, J=5.8 Hz), 4.40 (2H, t, J=5.8 Hz), 7.21–7.25 (2H, m), 7.40–7.46 (2H, m), 7.55 (1H, d, J=8.0 Hz)

The following compounds of Reference Examples 60 to 73 were obtained in the same manner as described in Reference Example 2.

REFERENCE EXAMPLE 60

5'-[3-(4-Chlorophenylsulfonyl)propyl]-2'-hydroxy-3-(6-methoxy-2-benzothiazolylmethoxy)benzanilide Nuclear magnetic resonance spectrum (DMSO-d₆, TMS internal standard)

δ: 1.76–1.82 (2H, m), 2.56 (2H, t, J=7.3 Hz), 3.31–3.34 (2H, m), 3.83 (3H, s), 5.64 (2H, s), 6.82 (2H, s), 7.13 (1H, d, J=8.5 Hz), 7.32 (1H, d, J=8.0 Hz), 7.43 (1H, s), 7.48 (1H, t, J=8.0 Hz), 7.60 (1H, d, J=7.5 Hz), 7.68–7.74 (4H, m), 7.88–7.92 (3H, m), 9.51 (1H, s), 9.53 (1H, s)

REFERENCE EXAMPLE 61

5'-[3-(4-Chlorophenylsulfonyl)propyl]-2'-hydroxy-3-(4,5,6,7-tetrahydro-2-benzothiazolylmethoxy)benzanilide Nuclear magnetic resonance spectrum (DMSO-d₆, TMS internal standard)

δ: 1.73–1.83 (6H, m), 2.56 (2H, t, J=7.5 Hz), 2.63–2.78 (4H, m), 3.31–3.42 (2H, m), 5.42 (2H, s), 6.82 (2H, s), 7.23–7.32 (1H, m), 7.42–7.50 (2H, m), 7.54–7.63 (2H, m), 7.73 (2H, d, J=8.0 Hz), 7.89 (2H, d, J=8.0 Hz), 9.49 (1H, s), 9.54 (1H, s)

REFERENCE EXAMPLE 62

3-[(4-tert-Butyl-2-thiazolyl)methoxy]-5-chloro-5'-[3-(4-chlorophenylsulfonyl)propyl]-2'-hydroxybenzanilide Nuclear magnetic resonance spectrum (DMSO-d₆, TMS internal standard)

δ: 1.30 (9H, s), 1.73–1.85 (2H, m), 2.56 (2H, br-t, J=7.6 Hz), 3.30–3.36 (2H, m), 5.53 (2H, s), 6.83 (2H, s), 7.32 (1H, br-s), 7.33 (1H, s), 7.44 (1H, br-s), 7.62 (2H, br-s), 7.73 (2H, br-d, J=8.8 Hz), 7.89 (2H, br-d, J=8.8 Hz), 9.46 (1H, br-s), 9.65 (1H, br-s)

REFERENCE EXAMPLE 63

5-[(4-tert-Butyl-2-thiazolyl)methoxy]-2-chloro-5'-[3-(4-chlorophenylsulfonyl)propyl]-2'-hydroxybenzanilide Mass spectrometry data (m/z): 633 [(M+H)⁺]

Nuclear magnetic resonance spectrum (CDCl₃, TMS internal standard)

δ: 1.35 (9H, s), 1.99–2.04 (2H, m), 2.64 (2H, br-t, J=7.3 Hz), 3.03–3.07 (2H, m), 5.35 (2H, s), 6.88 (1H, br-d, J=8.3 Hz), 6.94 (1H, br-s), 6.95 (1H, br-d, J=8.3 Hz), 7.09 (1H, br-d, J=8.8 Hz), 7.10 (1H, s), 7.37 (1H, d, J=8.8 Hz), 7.50 (1H, br-s), 7.52 (1H, br-d, J=8.8 Hz), 7.80 (2H, br-d, J=8.8 Hz), 8.32 (1H, br-s), 8.49 (1H, s)

REFERENCE EXAMPLE 64

3-[(4-tert-Butyl-2-thiazolyl)methoxy]-5'-[3-(4-chlorophenylsulfonyl)propyl]-2'-hydroxy-4-methoxybenzanilide Mass spectrometry data (m/z): 629 (M⁺)

Nuclear magnetic resonance spectrum (CDCl₃, TMS internal standard)

δ: 1.33 (9H, s), 1.95–2.04 (2H, m), 2.62 (2H, br-t, J=7.3 Hz), 3.01–3.09 (2H, m), 3.96 (3H, s), 5.46 (2H, s), 6.85 (1H, dd, J=8.3, 2.0 Hz), 6.88–6.98 (3H, m), 7.00 (1H, d, J=2.0 Hz), 7.52 (2H, br-d, J=8.8 Hz), 7.59 (1H, dd, J=8.3, 2.0 Hz), 7.65 (1H, d, J=2.0 Hz), 7.79 (2H, br-d, J=8.3 Hz), 8.26 (1H, s), 8.75 (1H, br-s)

REFERENCE EXAMPLE 65

3-[(4-tert-Butyl-2-thiazolyl)methoxy]-4-chloro-5'-[3-(4-chlorophenylsulfonyl)propyl]-2'-hydroxybenzanilide Mass spectrometry data (m/z): 633 [(M+H)$^+$]

Nuclear magnetic resonance spectrum (CDCl$_3$, TMS internal standard)

δ: 1.35 (9H, s), 1.98–2.01 (2H, m), 2.63 (2H, br-t, J=7.3 Hz), 3.01–3.05 (2H, m), 5.47 (2H, s), 6.87 (1H, br-d, J=8.3 Hz), 6.95 (1H d, J=8.3 Hz), 6.96 (1H, s), 7.10 (1H, d, J=2.0 Hz), 7.47 (1H, br-d, J=8.3 Hz), 7.51 (1H, d, J=8.3 Hz), 7.52 (2H, br-d, J=8.8 Hz), 7.68 (1H, d, J=2.0 Hz), 7.79 (2H, br-d, J=8.8 Hz), 8.34 (1H, s), 8.35 (1H, s)

REFERENCE EXAMPLE 66

3-[(4-tert-Butyl-2-thiazolyl)methoxy]-5'-[3-(4-chlorophenylsulfonyl)propyl]-2'-hydroxy-4-methylbenzanilide Mass spectrometry data (m/z): 613 (M$^+$)

Nuclear magnetic resonance spectrum (CDCl$_3$, TMS internal standard)

δ: 1.36 (9H, s), 1.91–1.99 (2H, m), 2.35 (3H, s), 2.57 (2H, br-t, J=7.3 Hz), 2.99–3.03 (2H, m), 5.35 (2H, s), 6.82 (1H, dd, J=8.3, 2.0 Hz), 6.91–6.94 (2H, m), 7.13 (1H, br-s), 7.25 (1H, br-d, J=8.3 Hz), 7.44 (1H, br-d, J=8.3 Hz), 7.47 (1H, s), 7.49 (2H, br-d, J=8.3 Hz), 7.76 (2H, br-d, J=8.3 Hz), 8.49 (1H, s), 8.87 (1H, s)

REFERENCE EXAMPLE 67

3-[(4-tert-Butyl-2-thiazolyl)methoxy]-5'-[3-(4-chlorophenylsulfonyl)propyl]-2'-hydroxy-4-nitrobenzanilide Mass spectrometry data (m/z): 644 (M$^+$)

Nuclear magnetic resonance spectrum (CDCl$_3$, TMS internal standard)

δ: 1.32 (9H, s), 1.95–1.99 (2H, m), 2.60 (2H, br-t, J=7.6 Hz), 3.03 (2H, m), 5.51 (2H, s), 6.85 (1H, dd, J=8.3, 2.0 Hz), 6.91 (1H, d, J=8.3 Hz), 6.99 (1H, s), 7.29 (1H, d, J=2.0 Hz), 7.52 (2H, br-d, J=8.3 Hz), 7.58 (1H, dd, J=8.3, 1.5 Hz), 7.78 (2H, br-d, J=8.3 Hz), 7.84 (1H, s), 7.89 (1H, d, J=8.3 Hz), 8.30 (1H, br-s), 8.67 (1H, s)

REFERENCE EXAMPLE 68

3-[(4-tert-Butyl-5-methyl-2-thiazolyl)methoxy]-5'-[3-(4-chlorophenylsulfonyl)propyl]-2'-hydroxybenzanilide Mass spectrometry data (m/z): 613 [(M+H)$^+$]

Nuclear magnetic resonance spectrum (DMSO-d$_6$, TMS internal standard)

δ: 1.36 (9H, s), 1.77–1.81 (2H, m), 2.49 (3H, s), 2.56 (2H, br-t, J=7.3 Hz), 3.32–3.35 (2H, m), 5.37 (2H, s), 6.82 (2H, br-s), 7.27 (1H, dd, J=7.8, 2.0 Hz), 7.42 (1H, br-s), 7.46 (1H, t, J=7.8 Hz), 7.57 (1H, d, J=7.8 Hz), 7.64 (1H, br-s), 7.74 (2H, br-d, J=8.8 Hz), 7.89 (2H, br-d, J=8.8 Hz), 9.51 (1H, s), 9.53 (1H, s)

REFERENCE EXAMPLE 69

6-(4-tert-Butyl-2-thiazolylmethoxy)-N-[5-[3-(4-chlorophenylsulfonyl)propyl]-2-hydroxyphenyl]pyridine-2-carboxyamide Nuclear magnetic resonance spectrum (DMSO-d$_6$, TMS internal standard)

δ: 1.30 (9H, s), 2.01–2.08 (2H, m), 2.67 (2H, t, J=7.2 Hz), 3.04–3.09 (2H, m), 5.76 (2H, s), 6.88–6.98 (3H, m), 7.04 (1H, s), 7.12 (1H, d, J=8.0 Hz), 7.52 (2H, d, J=8.4 Hz), 7.80–7.88 (3H, m), 7.94 (1H, d, J=7.2 Hz), 9.06 (1H, br), 9.91 (1H, s)

REFERENCE EXAMPLE 70

3-[2-(4-tert-Butyl-2-thiazolyl)ethoxy]-5'-[3-(4-chlorophenylsulfonyl)propyl]-2'-hydroxybenzanilide Nuclear magnetic resonance spectrum (DMSO-d$_6$, TMS internal standard)

δ: 1.28 (9H, s), 1.70–1.83 (2H, m), 2.56 (2H, t, J=7.3 Hz), 3.31–3.35 (2H, m), 3.44 (2H, t, J=5.9 Hz), 4.41 (2H, t, J=5.9 Hz), 6.82 (2H, s), 7.12 (1H, s), 7.18 (1H, d, J=8.0 Hz), 7.42–7.46 (2H, m), 7.53–7.55 (2H, m), 7.73 (2H, d, J=8.8 Hz), 7.90 (2H, d, J=8.8 Hz), 9.51 (1H, s), 9.52 (1H, s)

REFERENCE EXAMPLE 71

3-(4-tert-Butyl-2-thiazolylmethoxy)-2'-hydroxy-5'-(3-phenylsulfonylpropyl)benzanilide Nuclear magnetic resonance spectrum (DMSO-d$_6$, TMS internal standard)

δ: 1.31 (9H, s), 1.75–1.83 (2H, m), 2.56 (2H, t, J=7.2 Hz), 3.27–3.32 (2H, m), 5.50 (2H, s), 6.82 (2H, s), 7.28–7.32 (2H, m), 7.42 (1H, s), 7.47 (1H, t, J=8.4 Hz), 7.59 (1H, d, J=7.6 Hz), 7.64–7.67 (3H, m), 7.45 (1H, t, J=6.8 Hz), 7.89 (2H, d, J=8.0 Hz), 9.52 (2H, br)

REFERENCE EXAMPLE 72

3-[(4-tert-Butyl-2-thiazolyl)methoxy]-5'-[3-(4-chlorophenylsulfonyl)propyl]-3',4'-dichloro-2'-hydroxybenzanilide Nuclear magnetic resonance spectrum (DMSO-d$_6$, TMS internal standard)

δ: 1.31 (9H, s), 1.76–1.86 (2H, m), 2.72–2.77 (2H, m), 3.39–3.44 (2H, m), 5.50 (2H, s), 7.32–7.33 (2H, m), 7.38 (1H, s), 7.49 (1H, br-t, J=7.8 Hz), 7.63 (1H, br-d, J=7.8 Hz), 7.71–7.74 (3H, m), 7.91 (2H, d, J=8.8 Hz), 9.97 (1H, br-s), 10.08 (1H, br-s)

REFERENCE EXAMPLE 73

3-[(4-tert-Butyl-2-thiazolyl)methoxy]-3'-chloro-5'-[3-(4-chlorophenylsulfonyl)propyl]-2'-hydroxybenzanilide Nuclear magnetic resonance spectrum (DMSO-d$_6$, TMS internal standard)

δ: 1.31 (9H, s), 1.76–1.85 (2H, m), 2.55–2.60 (2H, m), 3.31–3.35 (2H, m), 5.50 (2H, s), 7.70 (1H, br-s), 7.24 (1H, br-s), 7.32–7.34 (2H, m), 7.49 (1H, br-t, J=7.8 Hz), 7.62 (1H, br-d, J=7.8 Hz), 7.70–7.74 (1H, m), 7.73 (2H, d, J=8.8 Hz), 7.90 (2H, d, J=8.8 Hz), 9.58 (1H, br-s), 9.96 (1H, br-s)

REFERENCE EXAMPLE 74

5'-[3-(4-Chlorobenzenesulfonyl)propyl]-2'-hydroxy-3-[(4-tert-butyl-2-thiazolyl)methoxy]benzanilide (1.60 g, 2.67 mmol) was dissolved in dimethylformamide (16 ml), potassium carbonate (0.55 g, 4.00 mmol), a catalytically effective amount of tetrabutylammonium bromide and bromoacetonitrile (0.22 ml, 3.20 mmol) were added in that order under ice-cooling, followed by overnight stirring at room temperature. Ice-water was added to the reaction solution and the mixture was extracted twice with benzene-ethyl acetate (1:1). The resulting organic layer was washed with 5% potassium carbonate aqueous solution and brine in that order, dried over anhydrous magnesium sulfate, and then concentrated under reduced pressure. By crystallizing the resulting residue from acetonitrile, 3-[(4-tert-butyl-2-thiazolyl)methoxy]-5'-[3-(4-chlorophenylsulfonyl)propyl]-2'-cyanomethoxybenzanilide was obtained as colorless crystals (1.34 g, 79%).

Nuclear magnetic resonance spectrum (CDCl$_3$, TMS internal standard)

δ: 1.36 (9H, s), 2.02–2.08 (2H, m), 2.72 (2H, br-t, J=7.3 Hz), 3.07–3.11 (2H, m), 4.87 (2H, s), 5.41 (2H, s), 6.88–6.94 (3H, m), 7.22 (2H, dt, J=6.8, 2.4 Hz), 7.43–7.45 (2H, m), 7.53 (2H, dd, J=8.8, 1.9 Hz), 7.55 (1H, br-s), 7.83 (2H, dd, J=8.8, 1.9 Hz), 8.28 (1H, br-s), 8.31 (1H, br-s)

The following compounds of Reference Examples 75 and 76 were obtained in the same manner as described in Reference Example 74.

REFERENCE EXAMPLE 75

3-[(4-tert-Butyl-2-thiazolyl)methoxy]-2'-(cyanomethoxy)-5'-[3-(4-phenylsulfonyl)propyl]benzanilide Mass spectrometry data (m/z): 604 [(M+H)$^+$]

Nuclear magnetic resonance spectrum (CDCl$_3$, TMS internal standard)

δ: 1.36 (9H, s), 2.02–2.10 (2H, m), 2.71 (2H, t, J=7.3 Hz), 3.07–0.12 (2H, m), 4.67 (2H, s), 5.41 (2H, s), 6.88–6.94 (3H, m), 7.20–7.23 (1H, m), 7.41–7.45 (2H, m), 7.54–7.59 (3H, m), 7.62–7.67 (1H, m), 7.90 (2H, d, J=8.0 Hz), 8.27 (1H, s), 8.32 (1H, s)

REFERENCE EXAMPLE 76

5'-[3-(4-Chlorophenylsulfonyl)propyl]-2'-(cyanomethoxy)-3-[(4-cyclobutyl-2-thiazolyl)methoxy]benzanilide Mass spectrometry data (m/z): 636 [(M+H)$^+$]

Nuclear magnetic resonance spectrum (CDCl$_3$, TMS internal standard)

δ: 1.89–1.95 (1H, m), 2.00–2.09 (3H, m), 2.23–2.31 (2H, m), 2.34–2.41 (2H, m), 2.70–2.73 (2H, m), 2.88–3.10 (2H, m), 3.65–3.72 (1H, m), 4.87 (2H, s), 5.41 (2H, s), 6.89 (1H, dd, J=8.6, 1.8 Hz), 6.93 (1H, d, J=8.6 Hz), 6.95 (1H, s), 7.21 (1H, dd, J=7.3 Hz, 1.8 Hz), 7.43 (1H, t, J=7.3 Hz), 7.46 (1H, br-d, J=7.3 Hz), 7.53 (2H, d, J=8.3 Hz), 7.54 (1H, s), 7.83 (2H, d, J=8.3 Hz), 8.28 (1H, s), 8.32 (1H, d, J=1.8 Hz)

REFERENCE EXAMPLE 77

Methyl 3-hydroxybenzoate (10.00 g, 65.72 mmol) was dissolved in dimethylformamide (100 ml). With stirring the solution under ice-cooling, potassium carbonate (13.63 g, 98.58 mmol) and chloroacetonitrile (4.99 ml, 78.86 mmol) were added in that order, and the mixture was stirred at room temperature for 12 hours. The reaction solution was poured into ice-water and the crystals precipitated were collected by filtration. The resulting crystals were dissolved in chloroform, and the solution was washed with 5% potassium carbonate aqueous solution, 10% citric acid aqueous solution and brine in that order, dried over anhydrous magnesium sulfate, and then concentrated under reduced pressure. By crystallizing the resulting residue from diethyl etherhexane, methyl 3-cyanomethoxybenzoate (811.80 g, 94%) was obtained.

Nuclear magnetic resonance spectrum (CDCl$_3$, TMS internal standard)

δ: 3.93 (3H, s), 4.82 (2H, s), 7.11–7.25 (1H, m), 7.43 (1H, br-t, J=7.5 Hz), 7.61–7.66 (1H, m), 7.79 (1H, dt, J=7.5, 1.3 Hz)

REFERENCE EXAMPLE 78

4 N Hydrogen chloride-ethyl acetate solution (50 ml) and dithiophosphate=O,O-diethyl (4.47 ml, 26.67 mmol) were added in that order to methyl 3-cyanomethoxybenzoate (5.00 g, 26.15 mmol), and the resulting solution was stirred at room temperature for 12 hours. Crystals precipitated in the reaction solution were collected by filtration and washed with diethyl ether to give methyl 3-thiocarbamoylmethoxybenzoate (4.60 g, 78%).

Nuclear magnetic resonance spectrum (CDCl$_3$, TMS internal standard)

δ: 3.86 (3H, s), 4.83 (2H, s), 7.27 (1H, dd, J=7.9, 2.4 Hz), 7.46 (1H, br-t, J=7.9 Hz), 7.54 (1H, br-s), 7.59 (1H, br-d, J=7.9 Hz), 9.43 (1H, br-s), 10.01 (1H, br-s)

The following compound of Reference Example 79 was obtained in the same manner as described in Reference Example 78.

REFERENCE EXAMPLE 79

Methyl 3-(2-thiocarbamoylethoxy)benzoate

Nuclear magnetic resonance spectrum (DMSO-d$_6$, TMS internal standard)

δ: 2.92 (2H, t, J=6.2 Hz), 3.85 (3H, s), 4.39 (2H, t, J=6.2 Hz), 7.14–7.60 (4H, m), 9.20–9.70 (2H, br)

REFERENCE EXAMPLE 80

Cyclopentyl=methyl ketone (0.20 g, 1.78 mmol) was dissolved in methanol (5 ml). With stirring the solution under ice-cooling, a catalytically effective amount of 33% hydrogen bromide-acetic acid was added and then bromine (0.34 g, 2.14 mmol) was added dropwise. Potassium carbonate (0.15 g, 1.07 mmol) was added to the reaction solution, and the mixture was stirred at room temperature for 10 minutes. Then, methyl 3-thiocarbamoylmethoxybenzoate (0.40 g, 1.78 mmol) was added to the reaction solution and the mixture was heated under reflux for 1 hour. After cooling, the reaction solution was concentrated under reduced pressure, ice-water and 5% potassium carbonate aqueous solution were added to the resulting residue, and then the product formed was extracted with chloroform. The organic layer was washed with 5% potassium carbonate aqueous solution, 10% citric acid aqueous solution and brine in that order, dried over anhydrous magnesium sulfate, and then concentrated under reduced pressure. Tetrahydrofuran (5 ml), methanol (5 ml) and 1 N sodium hydroxide aqueous solution (2 ml) were added to the resulting residue, and the mixture was stirred at room temperature for 12 hours. The reaction solution was concentrated under reduced pressure, 10% citric acid aqueous solution was added to the resulting residue, and then the product formed was extracted with chloroform. The organic layer was washed with brine, dried over anhydrous magnesium sulfate, and then concentrated under reduced pressure. By crystallizing the resulting residue from diethyl etherhexane, 3-(4-cyclopentyl-2-thiazolyl)methoxybenzoic acid (0.15 g, 28%) was obtained.

Nuclear magnetic resonance spectrum (CDCl$_3$, TMS internal standard)

δ: 1.66–1.81 (6H, m), 2.06–2.16 (2H, m), 3.22–3.31 (1H, m), 5.43 (2H, s), 6.93 (1H, s), 7.23–7.26 (1H, m), 7.40 (1H, br-t, J=8.3 Hz), 7.75–7.78 (2H, m), 8.5–9.5 (1H, br)

The following compounds of Reference Examples 81 to 85 were obtained in the same manner as described in Reference Example 80.

REFERENCE EXAMPLE 81

3-(4-Cyclohexyl-2-thiazolyl)methoxybenzoic acid

Nuclear magnetic resonance spectrum (CDCl$_3$, TMS internal standard)

δ: 1.20–1.31 (1H, m), 1.37–1.49 (4H, m), 1.72–1.76 (1H, m), 1.81–1.87 (2H, m), 2.05–2.12 (2H, m), 2.78–2.84 (1H, m), 5.43 (2H, s), 6.90 (1H, s), 7.23–7.26 (1H, m), 7.38–7.41 (1H, m), 7.75–7.80 (2H, m), 10.6–11.2 (1H, br)

REFERENCE EXAMPLE 82

3-(4-Cyclobutyl-2-thiazolyl)methoxybenzoic acid

Nuclear magnetic resonance spectrum (CDCl$_3$, TMS internal standard)

δ: 1.8–2.2 (6H, m), 3.54–3.91 (1H, m), 5.43 (2H, s), 6.94 (1H, d, J=0.8 Hz), 7.16–7.42 (2H, m), 7.70–7.84 (2H, m)

REFERENCE EXAMPLE 83

3-(4-Phenyl-2-thiazolyl)methoxybenzoic acid

Nuclear magnetic resonance spectrum (CDCl$_3$, TMS internal standard)

δ: 5.49 (2H, s), 7.20–7.57 (6H, m), 7.72–7.97 (4H, m)

REFERENCE EXAMPLE 84

3-(4-Cyclopropyl-2-thiazolyl)methoxybenzoic acid

Nuclear magnetic resonance spectrum (CDCl$_3$, TMS internal standard)

δ: 0.87–1.02 (4H, m), 1.95–2.26 (1H, m), 5.38 (2H, s), 6.86 (1H, s), 7.16–7.49 (2H, m), 7.72–7.81 (2H, m), 8.8–9.3 (1H, br)

REFERENCE EXAMPLE 85

3-(4-tert-Butyl-2-thiazolyl)methoxybenzoic acid

Nuclear magnetic resonance spectrum (CDCl$_3$, TMS internal standard)

δ: 1.03 (9H, s), 5.46 (2H, s), 7.30 (1H, s), 7.31–7.34 (1H, m), 7.44 (1H, br-t, J=8.3 Hz), 7.57–7.59 (2H, m), 13.01 (1H, br-s)

REFERENCE EXAMPLE 86

3-[2-(4-tert-Butyl-2-thiazolyl)vinyl]benzoic acid (1.20 g, 4.18 mmol) was dissolved in tetrahydrofuran (24 ml), 10% palladium-carbon powder (0.2 g) was added to the solution, and the mixture was stirred at room temperature for 3 hours in an atmosphere of hydrogen. The reaction solution was filtered and the resulting filtrate was concentrated under reduced pressure. By crystallizing the resulting residue from diethyl ether-hexane, 3-[2-(4-tert-butyl-thiazolyl)ethyl]benzoic acid (1.12 g, 93%) was obtained.

Nuclear magnetic resonance spectrum (CDCl$_3$, TMS internal standard)

δ: 1.34 (9H, s), 3.05–3.48 (4H, m), 6.74 (1H, s), 7.32–7.40 (2H, m), 7.85–8.01 (2H, m)

The following compound of Reference Example 87 was obtained in the same manner as described in Reference Example 86.

REFERENCE EXAMPLE 87

3-[2-(4-Cyclobutyl-2-thiazolyl)ethyl]benzoic acid

Nuclear magnetic resonance spectrum (CDCl$_3$, TMS internal standard)

δ: 1.85–1.94 (1H, m), 1.98–2.08 (1H, m), 2.18–2.27 (2H, m), 2.33–2.41 (2H, m), 3.16 (2H, t, J=8.5 Hz), 3.36 (2H, t, J=8.5 Hz), 3.67–3.75 (1H, m), 6.78 (1H, s), 7.34–7.39 (2H, m), 7.95–7.97 (1H, m), 8.03 (1H, br-s)

REFERENCE EXAMPLE 88

Methyl 3-mercaptobenzoate (0.50 g, 2.97 mmol) and 2-bromomethyl-4-tert-butylthiazole (0.50 g, 3.27 mmol) were dissolved in 2-butanone (10 ml). Potassium carbonate (0.41 g, 4.46 mmol) was added to the solution with stirring under ice-cooling, and the mixture was then stirred at room temperature for 12 hours. Ice and 5% potassium carbonate aqueous solution were added and the product formed was extracted with chloroform. The organic layer was washed with 5% potassium carbonate aqueous solution, 10% citric acid aqueous solution and brine in that order, dried over anhydrous magnesium sulfate, and then concentrated under reduced pressure. Tetrahydrofuran (10 ml), methanol (5 ml) and 1 N sodium hydroxide aqueous solution (4.46 ml) were added to the resulting residue and the mixture was stirred at room temperature for 7 hours. The reaction solution was concentrated under reduced pressure, 10% citric acid aqueous solution was added to the resulting residue, and then the product formed was extracted with chloroform. The organic layer was washed with brine, dried over anhydrous magnesium sulfate, and then concentrated under reduced pressure. By crystallizing the resulting residue from chloroform-diethyl ether, 3-(4-tert-butyl-2-thiazolyl)methylthiobenzoic acid (0.81 g, 83%) was obtained.

Nuclear magnetic resonance spectrum (CDCl$_3$, TMS internal standard)

δ: 1.29 (9H, s), 5.41 (2H, s), 6.80 (1H, s), 7.33 (1H, br-t, J=7.8 Hz), 7.56 (1H, dt, J=7.8, 1.6 Hz), 7.93 (1H, dt, J=7.8, 1.6 Hz), 8.14 (1H, br-t, J=1.6 Hz)

EXAMPLE 1

5'-[3-(4-Chlorophenylsulfonyl)propyl]-2'-hydroxy-3-[2-(4-phenyl-2-thiazolyl)vinyl]benzanilide (0.60 g, 0.98 mmol) was dissolved in dimethylformamide (6 ml), potassium carbonate (0.20 g, 1.45 mmol), a catalytically effective amount of tetrabutylammonium bromide and ethyl bromoacetate (0.13 ml, 1.17 mmol) were added in that order under ice-cooling, followed by 12 hours of stirring at room temperature. Ice-water was added to the reaction solution and the product formed was extracted twice with benzene-ethyl acetate mixed solution (1:1). The resulting organic layer was washed with 5% potassium carbonate aqueous solution and brine in that order, dried over anhydrous magnesium sulfate, and then concentrated under reduced pressure. The resulting residue was purified by silica gel column chromatography (eluent=acetone:chloroform=1:100) and crystallized from acetonitrile to give ethyl 4-[3-(4-chlorophenylsulfonyl)propyl]-2-[3-[2-(4-phenyl-2-thiazolyl)vinyl]benzoylamino]phenoxyacetate (0.36 g, 0.51 mmol, 53%) as colorless crystals.

The following compounds of Examples 2 to 7 were synthesized in the same manner as described in Example 1 above. Structures and physicochemical properties of these compounds are shown in Tables 12 and 13.

In this connection, the term "binding position" shown in the tables means a binding position to

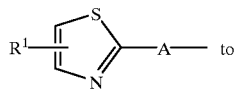

-continued

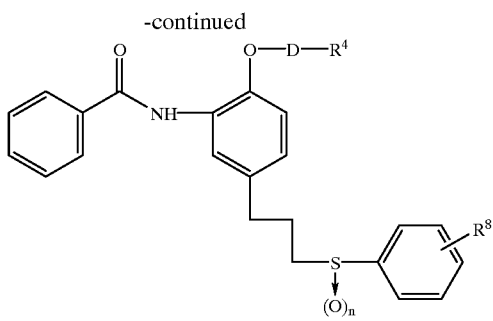

of the general formula (I), and the term "binding position to thiazole ring" means a position where $R^1$ binds to the thiazole ring. The same shall apply hereinafter.

EXAMPLE 2

Ethyl 4-[3-(4-chlorophenylsulfonyl)propyl]-2-[3-[2-[4-(4-methylphenyl)-2-thiazolyl]vinyl]benzoylamino]phenoxyacetate

EXAMPLE 3

Ethyl 4-[3-(4-chlorophenylsulfonyl)propyl]-2-[3-[2-[(4-isopropyl-2-thiazolyl)vinyl]benzoylamino]phenoxyacetate

EXAMPLE 4

Ethyl 2-[3-[2-(4-tert-butyl-2-thiazolyl)vinyl]benzoylamino-4-[3-(4-chlorophenylsulfonyl)propyl]phenoxyacetate

EXAMPLE 5

Ethyl 4-[3-(4-chlorophenylsulfonyl)propyl]-2-[3-[(4-phenyl-2-thiazolyl)methoxy]benzoylamino]phenoxyacetate

EXAMPLE 6

Ethyl 2-[3-[(4-tert-butyl-2-thiazolyl)methoxy]benzoylamino]-4-[3-(4-chlorophenylsulfonyl)propyl]phenoxyacetate

EXAMPLE 7

Ethyl 4-[3-(4-chlorophenylsulfonyl)propyl]-2-[3-[2-(4-cyclopropyl-2-thiazolyl)vinyl]benzoylamino]phenoxyacetate

EXAMPLE 8

Ethyl 4-[3-(4-chlorophenylsulfonyl)propyl]-2-[3-[2-(4-phenyl-2-thiazolyl)vinyl]benzoylamino]phenoxyacetate (0.30 g, 0.43 mmol) was dissolved in a mixed solution of tetrahydrofuran (10 ml) and methanol (5 ml), 1 N sodium hydroxide aqueous solution (1.0 ml) was added to the solution, and the mixture was subjected to 12 hours of reaction. The reaction solution was acidified by adding ice and 10% citric acid aqueous solution, and the product formed was extracted three times with chloroform. The resulting organic layer was washed with brine, dried over anhydrous magnesium sulfate, and then concentrated under reduced pressure. By crystallizing the resulting residue from chloroform-acetonitrile, 4-[3-(4-chlorophenylsulfonyl)propyl]-2-[3-[2-(4-phenyl-2-thiazolyl)vinyl]benzoylamino]phenoxyacetic acid (0.24 g, 0.36 mmol, 83%) was obtained as colorless crystals.

The following compounds of Examples 9 to 14 were synthesized in the same manner as described in Example 8. Structures and physicochemical properties of these compounds are shown in Table 14.

EXAMPLE 9

4-[3-(4-Chlorophenylsulfonyl)propyl]-2-[3-[2-[4-(4-methylphenyl)-2-thiazolyl]vinyl]benzoylamino]phenoxyacetic acid

EXAMPLE 10

4-[3-(4-Chlorophenylsulfonyl)propyl]-2-[3-[2-(4-isopropyl-2-thiazolyl)vinyl]benzoylamino]phenoxyacetic acid

EXAMPLE 11

2-[3-[2-(4-tert-Butyl-2-thiazolyl)vinyl]benzoylamino]-4-[3-(4-chlorophenylsulfonyl)propyl]phenoxyacetic acid

EXAMPLE 12

4-[3-(4-Chlorophenylsulfonyl)propyl]-2-[3-[(4-phenyl-2-thiazolyl)methoxy]benzoylamino]phenoxyacetic acid

EXAMPLE 13

2-[3-[(4-tert-Butyl-2-thiazolyl)methoxy]benzoylamino]-4-[3-(4-chlorophenylsulfonyl)propyl]phenoxyacetic acid

EXAMPLE 14

4-[3-(4-Chlorophenylsulfonyl)propyl]-2-[3-[2-(4-cyclopropyl-2-thiazolyl)vinyl]benzoylamino)phenoxyacetic acid The following compounds of Examples 15 to 21 were synthesized in the same manner as described in Example 1. Structures and physicochemical properties of these compounds are shown in Tables 15 and 16.

EXAMPLE 15

Ethyl 4-[3-(4-chlorophenylsulfonyl)propyl]-2-[3-[(4-cyclopropyl-2-thiazolyl]methoxy]benzoylamino]phenoxyacetate

EXAMPLE 16

Ethyl 2-[3-[(4-tert-butyl-2-thiazolyl)methylthio]benzoylamino]-4-[3-(4-chlorophenylsulfonyl)propyl]phenoxyacetate

EXAMPLE 17

Ethyl 2-[3-[2-(4-tert-butyl-2-thiazolyl)ethyl]benzoylamino]-4-[3-(4-chlorophenylsulfonyl)propyl]phenoxyacetate

EXAMPLE 18

Ethyl 4-[3-(4-Chlorophenylsulfonyl)propyl]-2-[3-[(4-cyclohexyl-2-thiazolyl)methoxy]benzoylamino]phenoxyacetate

EXAMPLE 19

Ethyl 4-[3-(4-Chlorophenylsulfonyl)propyl]-2-[3-[(4-cyclopentyl-2-thiazolyl)methoxy]benzoylamino]phenoxyacetate

EXAMPLE 20

Ethyl 4-[3-(4-Chlorophenylsulfonyl)propyl]-2-[3-[(4-cyclobutyl-2-thiazolyl)methoxy]benzoylamino]phenoxyacetate

EXAMPLE 21

Ethyl 2-[3-[1-(4-tert-butyl-2-thiazolyl)ethoxy]benzoylamino]-4-[3-(4-chlorophenylsulfonyl)propyl]phenoxyacetate

EXAMPLE 22

1) The following compound was synthesized in accordance with the method of Example 1.

Ethyl 2-[3-[(4-tert-butyl-2-thiazolyl)methoxy]-5-(4-nitrobenzyloxycarbonylamino)benzoylamino]-4-[3-(4-chlorophenylsulfonyl)propyl]phenoxyacetate Mass spectrometry data (m/z): 879 (M$^+$)

Nuclear magnetic resonance spectrum (CDCl$_3$, TMS internal standard)

δ: 1.27 (3H, t, J=7.3 Hz), 1.34 (9H, s), 1.98–2.06 (2H, m), 2.67 (2H, br-t, J=7.3 Hz), 3.06–3.10 (2H, m), 4.29 (2H, q, J=7.3 Hz), 4.70 (2H, s), 5.28 (2H, s), 5.43 (2H, s), 6.82 (2H, s), 6.92 (1H, s), 7.23 (1H, br-s), 7.42 (1H, br-s), 7.50–7.55 (4H, m), 7.67 (1H, br-s), 7.82 (2H, d, J=8.8 Hz), 8.20 (2H, d, J=8.8 Hz), 8.24 (1H, br-s), 9.30 (1H, br-s)

2) Ethyl 2-[3-[(4-tert-butyl-2-thiazolyl)methoxy]-5-(4-nitrobenzyloxycarbonylamino)benzoylamino]-4-[3-(4-chlorophenylsulfonyl)propyl]phenoxyacetate (0.50 g, 0.57 mmol) was dissolved in a mixed solution of ethanol (10 ml) and tetrahydrofuran (10 ml), 10% palladium-carbon (0.10 g) was added to the solution, and the mixture was stirred at room temperature for 3 hours in an atmosphere of hydrogen. The reaction solution was filtered and the resulting filtrate was concentrated under reduced pressure. The resulting residue was purified by silica gel column chromatography (eluent=acetone:chloroform=3:100) and crystallized from acetonitrile to give ethyl 2-[3-amino-5-[(4-tert-butyl-2-thiazolyl)methoxy]benzoylamino]-4-[3-(4-chlorophenylsulfonyl)propyl]phenoxyacetate (0.17 g, 0.24 mmol, 43%) as light yellow crystals. Its structure is shown in Table 30.

Mass spectrometry data (m/z): 700 (M$^+$)

Nuclear magnetic resonance spectrum (CDCl$_3$, TMS internal standard)

δ: 1.28 (3H, t, J=7.3 Hz), 1.34 (9H, s), 1.99–2.07 (2H, m), 2.68 (2H, br-t, J=7.3 Hz), 3.89 (2H, br-s), 4.29 (2H, q, J=7.3 Hz), 4.70 (2H, s), 5.39 (2H, s), 6.52 (1H, br-t, J=1.9 Hz), 6.81 (2H, s), 6.91 (1H, s), 6.99 (1H, br-s), 7.07 (1H, br-s), 7.53 (2H, d, J=8.8 Hz), 7.82 (2H, d, J=8.3 Hz), 8.27 (1H, br-s), 9.18 (i1H, br-s)

The following compounds of Examples 23 to 25 were synthesized in accordance with the method of Example 1. Structures and physicochemical properties of these compounds are shown in Table 17.

EXAMPLE 23

Ethyl 4-[2-[3-[(4-tert-butyl-2-thiazolyl)methoxy]benzoylamino]-4-[3-(4-chlorophenylsulfonyl)propyl]phenoxy]butyrate

EXAMPLE 24

Ethyl 2-[2-[3-[(4-tert-butyl-2-thiazolyl)methoxy]benzoylamino]-4-[3-(4-chlorophenylsulfonyl)propyl]phenoxy]-2-methylpropionate

EXAMPLE 25

Ethyl 2-[2-[3-[(4-tert-butyl-2-thiazolyl)methoxy]benzoylamino]-4-[3-(4-chlorophenylsulfonyl)propyl]phenoxy]propionate The following compounds of Examples 26 to 32 were synthesized in accordance with the method of Example 8. Structures and physicochemical properties of these compounds are shown in Table 18.

EXAMPLE 26

4-[3-(4-Chlorophenylsulfonyl)propyl]-2-[3-[(4-cyclopropyl-2-thiazolyl)methoxy]benzoylamino]phenoxyacetic acid

EXAMPLE 27

2-[3-[(4-tert-Butyl-2-thiazolyl)methylthio]benzoylamino]-4-[3-(4-chlorophenylsulfonyl)propyl]phenoxyacetic acid

EXAMPLE 28

2-[3-[2-(4-tert-Butyl-2-thiazolyl)ethyl]benzoylamino]-4-[3-(4-chlorophenylsulfonyl)propyl]phenoxyacetic acid

EXAMPLE 29

4-[3-(4-Chlorophenylsulfonyl)propyl]-2-[3-[(4-cyclohexyl-2-thiazolyl)methoxy]benzoylamino]phenoxyacetic acid

EXAMPLE 30

4-[3-(4-Chlorophenylsulfonyl)propyl]-2-[3-[(4-cyclopentyl-2-thiazolyl)methoxy]benzoylamino]phenoxyacetic acid

EXAMPLE 31

4-[3-(4-Chlorophenylsulfonyl)propyl]-2-[3-[(4-cyclobutyl-2-thiazolyl)methoxy]benzoylamino]phenoxyacetic acid

EXAMPLE 32

2-[3-[1-(4-tert-Butyl-2-thiazolyl)ethoxy]benzoylamino]-4-[3-(4-chlorophenylsulfonyl)propyl]phenoxyacetic acid

EXAMPLE 33

The following compound was synthesized in accordance with the method of Example 8. Its structure is shown in Table 30.

2-[3-Amino-5-[(4-tert-butyl-2-thiazolyl)methoxy]benzoylamino]-4-[3-(4-chlorophenylsulfonyl)propyl]phenoxyacetic acid Melting point: 133–135° C.

Mass spectrometry data (m/z): 672 (M$^+$)

Elemental analysis data (for $C_{32}H_{34}N_3O_7S_2Cl$)

|  | C (%) | H (%) | N (%) | S (%) | Cl (%) |
| --- | --- | --- | --- | --- | --- |
| calcd. | 55.68 | 5.26 | 6.09 | 9.29 | 5.14 |
| found | 55.47 | 5.02 | 6.06 | 9.10 | 4.92 |

The following compounds of Examples 34 to 36 were synthesized in accordance with the method of Example 8. Structures and physicochemical properties of these compounds are shown in Table 19.

EXAMPLE 34

4-[2-[3-[(4-tert-Butyl-2-thiazolyl)methoxy]benzoylamino]-4-[3-(4-chlorophenylsulfonyl)propyl]phenoxy]butyric acid

EXAMPLE 35

2-[2-[3-[(4-tert-Butyl-2-thiazolyl)methoxy]benzoylamino]-4-[3-(4-chlorophenylsulfonyl)propyl]phenoxy]-2-methylpropionic acid hemihydrate

EXAMPLE 36

2-[2-[3-[(4-tert-Butyl-2-thiazolyl)methoxy] benzoylamino]-4-[3-(4-chlorophenylsulfonyl)propyl] phenoxy]propionic acid hemihydrate

EXAMPLE 37

Ethyl 2-[3-[(4-tert-butyl-2-thiazolyl)methoxy] benzoylamino]-4-[3-(4-chlorophenylsulfonyl)propyl] phenoxyacetic acid (0.30 g, 0.44 mmol) was dissolved in ammonia-saturated methanol (10 ml) and the solution was subjected to 12 hours of reaction at room temperature. The reaction solution was concentrated under reduced pressure, and the resulting residue was crystallized from acetonitrile to give 2-[3-[(4-tert-butyl-2-thiazolyl)methoxy] benzoylamino]-4-[3-(4-chlorophenylsulfonyl)propyl] phenoxyacetamide (0.22 g, 0.34 mmol, 77%) as colorless crystals. Its structure is shown in Table 30.

Melting point: 147–148° C.

Mass spectrometry data (m/z): 656 (M$^+$)

Elemental analysis data (for $C_{32}H_{34}N_3O_6S_2Cl$)

|  | C (%) | H (%) | N (%) | S (%) | Cl (%) |
| --- | --- | --- | --- | --- | --- |
| calcd. | 58.57 | 5.22 | 6.40 | 9.77 | 5.40 |
| found | 58.39 | 5.13 | 6.38 | 9.65 | 5.30 |

EXAMPLE 38

Dimethylformamide (5.0 ml) was added to a mixture of 3-[2-(4-tert-butyl-2-thiazolyl)ethyl]-5'-[3-(4-chlorophenylsulfonyl)propyl]-2'-cyanomethoxybenzanilide (0.57 g, 0.90 mmol), ammonium chloride (96 mg, 1.8 mmol) and sodium azide (0.12 g, 1.9 mmol), and the resulting mixture was stirred at 70° C. for 12 hours. Ice and 10% citric acid aqueous solution were added to the reaction solution, and the product formed was extracted with ethyl acetate. The resulting organic layer was washed with water and brine in that order, dried over anhydrous magnesium sulfate, and then concentrated under reduced pressure. The resulting residue was purified by silica gel column chromatography (eluent=methanol:chloroform=3:100) and then crystallized from acetonitrile to give 3-[2-(4-tert-butyl-2-thiazolyl) ethyl]-5'-[3-(4-chlorophenylsulfonyl)propyl]-2'-(1H-tetrazol-5-ylmethoxy)benzanilide (0.34 g, 0.50 mmol, 56%) as colorless crystals. Its structure is shown in Table 30.

Melting point: 152–153° C.

Mass spectrometry data (m/z): 679 (M$^+$)

The following compounds of Examples 39 to 41 were synthesized in accordance with the method of Example 38. Structures and physicochemical properties of these compounds are shown in Table 20.

EXAMPLE 39

3-[(4-tert-Butyl-2-thiazolyl)methoxy]-5'-[3-(4-chlorophenylsulfonyl)propyl]-2'-(1H-tetrazol-5-ylmethoxy) benzanilide

EXAMPLE 40

3-[(4-tert-Butyl-2-thiazolyl)methylthio]-5'-[3-(4-chlorophenylsulfonyl)propyl]-2'-(1H-tetrazol-5-ylmethoxy) benzanilide 0.7 hydrate

EXAMPLE 41

5'-[3-(4-Chlorophenylsulfonyl)propyl]-3-[2-(4-cyclobutyl-2-thiazolyl)ethyl]-2'-(1H-tetrazol-5-ylmethoxy) benzanilide

EXAMPLE 42

Ethanol (5.0 ml) was added to 2-[3-[(4-tert-Butyl-2-thiazolyl)methoxy]benzoylamino]-4-[3-(4-chlorophenylsulfonyl)propyl]phenoxyacetic acid (0.30 g, 0.46 mmol), and the mixture was stirred at room temperature. This suspension was made into a uniform solution by adding 0.1 N potassium hydroxide-ethanol solution (4.6 ml) and then concentrated under reduced pressure. The resulting residue was dried in vacuo and then dissolved in acetone (10 ml). The resulting solution was cooled with ice, 4-chloromethyl-5-methyl-1,3-dioxol-2-one (0.10 g, 0.67 mmol) and sodium iodide (0.21 g, 1.4 mmol) were added, and the mixture was stirred at room temperature for 12 hours. Ice and saturated sodium bicarbonate aqueous solution were added to the reaction solution and the product formed was extracted with ethyl acetate. The resulting organic layer was washed with saturated sodium bicarbonate aqueous solution, 10% citric acid aqueous solution and brine in that order, dried over anhydrous magnesium sulfate, and then concentrated under reduced pressure. The resulting residue was purified by silica gel column chromatography (eluent=acetone:chloroform=3:100) and crystallized from chloroform-diethyl ether to give (5-methyl-2-oxo-1,3-dioxol-4-yl)methyl=2-[3-[(4-tert-butyl-2-thiazolyl) methoxy]benzoylamino]-4-[3-(4-chlorophenylsulfonyl) propyl]phenoxyacetic acid (0.15 g, 0.19 mmol, 43%) as colorless crystals. Its structure is shown in Table 30.

Melting point: 114–116° C.

Mass spectrometry data (m/z): 769 (M$^+$)

Elemental analysis data (for $C_{37}H_{37}N_2O_{10}S_2Cl$)

|  | C (%) | H (%) | N (%) | S (%) | Cl (%) |
| --- | --- | --- | --- | --- | --- |
| calcd. | 57.77 | 4.85 | 3.64 | 8.34 | 4.61 |
| found | 57.74 | 4.78 | 3.67 | 8.41 | 4.67 |

The following compound was synthesized in accordance with the method of Example 42.

EXAMPLE 43

Pivaloyloxymethyl=2-[3-[(4-tert-butyl-2-thiazolyl) methoxy]benzoylamino]-4-[3-(4-chlorophenylsulfonyl) propyl]phenoxyacetic acid Melting point: 98–100° C.

Mass spectrometry data (m/z): 771 (M$^+$)

Elemental analysis data (for $C_{38}H_{43}N_2O_9S_2Cl$)

|  | C (%) | H (%) | N (%) | S (%) | Cl (%) |
| --- | --- | --- | --- | --- | --- |
| calcd. | 59.17 | 5.62 | 3.63 | 8.34 | 4.60 |
| found | 59.42 | 5.62 | 3.56 | 8.41 | 4.64 |

EXAMPLE 44

Under ice-cooling, hydrazine monohydrate (190 µl, 3.8 mmol) was added to a mixture of N-[2-[2-[3-[(4-tert-butyl-2-thiazolyl)methoxy]benzoylamino]-4-[3-(4-chlorophenylsulfonyl)propyl]phenoxy]ethyl]phthalimide (1.5 g, 1.9 mmol), ethanol (5 ml) and tetrahydrofuran (20 ml), and the resulting mixture was stirred overnight at room temperature and then heated under reflux for 3 hours. Ice-water was added to the reaction solution, and then the product formed was extracted with chloroform. The resulting organic layer was washed with saturated sodium bicarbonate aqueous solution and distilled water in that order, dried over anhydrous magnesium sulfate, and then concentrated. The resulting residue was purified by silica gel column chromatography (eluent=chloroform:acetone=2:1), made into hydrochloride by adding 4 N hydrochloric acid/ethyl acetate, and then crystallized from diethyl ether to give 3-[(4-tert-butyl-2-thiazolyl)methoxy]-5'-[3-(4-chlorophenylsulfonyl)-propyl]-2'-(2-aminoethoxy) benzanilide 1.4 hydrochloride.0.7 hydrate (160 mg, 0.23 mmol, 12%) as white crystals.

Melting point: 93–96° C.

Mass spectrometry data (m/z): 642 (M$^+$)

Elemental analysis data (for $C_{32}H_{36}N_3O_5S_2Cl.1.4HCl.0.7H_2O$)

|  | C (%) | H (%) | N (%) | S (%) | Cl (%) |
| --- | --- | --- | --- | --- | --- |
| calcd. | 54.45 | 5.54 | 5.95 | 9.09 | 12.05 |
| found | 54.23 | 5.42 | 5.87 | 8.95 | 11.90 |

EXAMPLE 45

Under ice-cooling, acetic anhydride (30 μl, 0.3 mmol) was added to a mixture of 3-[(4-tert-butyl-2-thiazolyl)methoxy]-5'-[3-(4-chlorophenylsulfonyl)propyl]-2'-(2-aminoethoxy)benzanilide 1.4 hydrochloride.0.7 hydrate (170 mg, 0.24 mmol), dichloromethane (2 ml) and pyridine (32 μl, 0.4 mmol), and the resulting mixture was stirred at room temperature for 3 hours. Ice-water was added to the reaction solution and the mixture was stirred for 1 hour. The product formed was extracted with chloroform and the resulting organic layer was washed with 20% potassium hydrogensulfate aqueous solution, saturated sodium bicarbonate aqueous solution and distilled water in that order, dried over anhydrous magnesium sulfate, and then concentrated. The resulting residue was crystallized from chloroform-ether to give 3-[(4-tert-butyl-2-thiazolyl)methoxy]-5'-[3-(4-chlorophenylsulfonyl)propyl]-2'-(2-acetylaminoethoxy)benzanilide hemihydrate (97 mg, 0.14 mmol, 58%) as white crystals.

Melting point: 110.5–111.5° C.

Mass spectrometry data (m/z): 684 (M$^+$)

Elemental analysis data (for $C_{34}H_{38}N_3O_6S_2Cl.0.5H_2O$)

|  | C (%) | H (%) | N (%) | S (%) | Cl (%) |
| --- | --- | --- | --- | --- | --- |
| calcd. | 58.90 | 5.67 | 6.06 | 9.25 | 5.11 |
| found | 58.94 | 5.45 | 6.02 | 9.31 | 5.12 |

The following compound was synthesized in accordance with the method of Example 45

EXAMPLE 46

3-[(4-tert-Butyl-2-thiazolyl)methoxy]-5'-[3-(4-chlorophenylsulfonyl)propyl]-2'-(2-methylsulfonylaminoethoxy) benzanilide Melting point: 125.5–126° C.

Mass spectrometry data (m/z): 720 (M$^+$)

Elemental analysis data (for $C_{33}H_{38}N_3O_7S_3Cl$)

|  | C (%) | H (%) | N (%) | S (%) | Cl (%) |
| --- | --- | --- | --- | --- | --- |
| calcd. | 55.03 | 5.32 | 5.83 | 13.35 | 4.92 |
| found | 54.97 | 5.32 | 5.77 | 13.54 | 4.84 |

The following compounds of Examples 47 to 59 were obtained in the same manner as described in Example 1.

EXAMPLE 47

Ethyl 2-[3-[(4-tert-butyl-2-thiazolyl)methoxy]-5-chlorobenzoylamino]-4-[3-(4-chlorophenylsulfonyl)propyl]phenoxyacetate Mass spectrometry data (m/z): 718 (M$^+$)

Nuclear magnetic resonance spectrum (CDCl$_3$, TMS internal standard)

δ: 1.29 (3H, t, J=7.3 Hz), 1.35 (9H, s), 2.00–2.07 (2H, m), 2.69 (2H, br-t, J=7.3 Hz), 3.06–3.10 (2H, m), 4.31 (2H, q, J=7.3 Hz), 4.71 (2H, s), 5.43 (2H, s), 6.84 (2H, br-s), 6.94 (1H, s), 7.24 (1H, br-s), 7.53 (2H, br-d, J=8.3 Hz), 7.61–7.65 (2H, m), 7.82 (2H, br-d, J=8.3 Hz), 8.25 (1H, br-s), 9.35 (1H, br-s)

EXAMPLE 48

Ethyl 2-[5-[(4-tert-butyl-2-thiazolyl)methoxy]-2-chlorobenzoylamino]-4-[3-(4-chlorophenylsulfonyl)propyl]phenoxyacetate Mass spectrometry data (m/z): 719 [(M+H)$^+$]

Nuclear magnetic resonance spectrum (CDCl$_3$, TMS internal standard)

δ: 1.25 (3H, t, J=6.8 Hz), 1.35 (9H, s), 2.02–2.08 (2H, m), 2.70 (2H, br-t, J=7.3 Hz), 3.08–3.12 (2H, m), 4.25 (2H, q, J=6.8 Hz), 4.66 (2H, s), 5.38 (2H, s), 6.78 (1H, br-d, J=8.3 Hz), 6.84 (1H, br-d, J=8.3 Hz), 6.93 (1H, s), 7.07 (1H, dd, J=8.8, 2.0 Hz), 7.37 (1H, br-d, J=8.8 Hz), 7.49 (1H, d, J=2.0 Hz), 7.54 (2H, br-d, J=8.8 Hz), 7.83 (2H, br-d, J=8.8 Hz), 8.33 (1H, d, J=2.0 Hz), 9.01 (1H, s)

EXAMPLE 49

Ethyl 2-[3-[(4-tert-butyl-2-thiazolyl)methoxy]-4-methoxybenzoylamino]-4-[3-(4-chlorophenylsulfonyl)propyl]phenoxyacetate Mass spectrometry data (m/z): 715 (M$^+$)

Nuclear magnetic resonance spectrum (CDCl$_3$, TMS internal standard)

δ: 1.29 (3H, t, J=6.8 Hz), 1.33 (9H, s), 1.99–2.07 (2H, m), 2.69 (2H, br-t, J=7.3 Hz), 3.06–3.10 (2H, m), 3.96 (3H, s), 4.29 (2H, q, J=6.8 Hz), 4.70 (2H, s), 5.50 (2H, s), 6.80 (1H, br-d, J=8.3 Hz), 6.82 (1H, br-s), 6.91 (1H, s), 7.01 (1H, br-d, J=8.3 Hz), 7.52 (2H, br-d, J=8.3 Hz), 7.71 (1H, dd, J=8.3, 2.0 Hz), 7.80 (1H, dd, J=8.3, 2.0 Hz), 7.82 (2H, br-d, J=8.3 Hz), 8.28 (1H, s), 9.27 (1H, s)

EXAMPLE 50

Ethyl 2-[3-[(4-tert-butyl-2-thiazolyl)methoxy]-4-chlorobenzoylamino]-4-[3-(4-chlorophenylsulfonyl)propyl]phenoxyacetate Mass spectrometry data (m/z): 719 [(M+H)$^+$]

Nuclear magnetic resonance spectrum (CDCl$_3$, TMS internal standard)

δ: 1.30 (3H, t, J=6.8 Hz), 1.34 (9H, s), 2.02–2.06 (2H, m), 2.70 (2H, br-t, J=7.3 Hz), 3.06–3.11 (2H, m), 4.32 (2H, q, J=6.8 Hz), 4.71 (2H, s), 5.55 (2H, s), 6.86 (2H, br-d, J=8.3 Hz), 6.94 (1H, s), 7.53 (2H, br-d, J=8.8 Hz), 7.54 (1H, s), 7.82 (2H, br-d, J=8.8 Hz), 7.85 (1H, d, J=2.0 Hz), 8.26 (1H, s), 9.47 (1H, s)

EXAMPLE 51

Ethyl 2-[3-[(4-tert-butyl-2-thiazolyl)methoxy]-4-methylbenzoylamino]-4-[3-(4-chlorophenylsulfonyl)propyl]phenoxyacetate Mass spectrometry data (m/z): 699 (M$^+$)

Nuclear magnetic resonance spectrum (CDCl$_3$, TMS internal standard)

δ: 1.30 (3H, t, J=7.3 Hz), 1.35 (9H, s), 2.00–2.08 (2H, m), 2.38 (3H, s), 2.69 (2H, br-t, J=7.3 Hz), 3.07–3.11 (2H, m), 4.32 (2H, q, J=7.3 Hz), 4.71 (2H, s), 5.48 (2H, br-s), 6.85 (2H, br-s), 6.92 (1H, br-s), 7.30 (1H, d, J=7.8 Hz), 7.53 (2H, dd, J=8.3, 2.0 Hz), 7.58 (1H, d, J=7.8 Hz), 7.69 (1H, br-s), 7.82 (2H, br-d, J=8.3 Hz), 8.30 (1H, s), 9.35 (1H, s)

EXAMPLE 52

Ethyl-2-[3-[(4-tert-butyl-2-thiazolyl)methoxy]-4-nitrobenzoylamino]-4-[3-(4-chlorophenylsulfonyl)propyl]phenoxyacetate Mass spectrometry data (m/z): 730 (M$^+$)

Nuclear magnetic resonance spectrum (CDCl$_3$, TMS internal standard)

δ: 1.31 (3H, t, J=7.3 Hz), 1.33 (9H, s), 2.01–2.08 (2H, m), 2.71 (2H, br-t, J=7.3 Hz), 3.07–3.11 (2H, m), 4.33 (2H, q, J=7.3 Hz), 4.73 (2H, s), 5.63 (2H, s), 6.89 (2H, s), 6.95 (1H, s), 7.54 (2H, br-d, J=8.8 Hz), 7.78 (1H, dd, J=8.3, 1.5 Hz), 7.83 (2H, br-d, J=8.8 Hz), 7.99 (1H, d, J=8.3 Hz), 8.05 (1H, d, J=1.5 Hz), 8.25 (1H, s), 9.67 (1H, s)

EXAMPLE 53

Ethyl 2-[3-[(4-tert-butyl-5-methyl-2-thiazolyl)methoxy]benzoylamino]-4-[3-(4-chlorophenylsulfonyl)propyl]phenoxyacetate Mass spectrometry data (m/z): 699 [(M+H)$^+$]

Nuclear magnetic resonance spectrum (CDCl$_3$, TMS internal standard)

δ: 1.29 (3H, t, J=7.3 Hz), 1.40 (9H, s), 2.04–2.06 (2H, m), 2.51 (3H, s), 2.69 (2H, br-t, J=7.3 Hz), 3.07–3.11 (2H, m), 4.29 (2H, q, J=7.3 Hz), 4.71 (2H, s), 5.33 (2H, s), 6.82 (2H, br-s), 7.24 (1H, d, J=7.8 Hz), 7.42 (1H, t, J=7.8 Hz), 7.53 (2H, br-d, J=8.3 Hz), 7.62 (1H, d, J=7.8 Hz), 7.69 (1H, br-s), 7.82 (2H, br-d, J=8.3 Hz), 8.30 (1H, s), 9.25 (1H, s)

EXAMPLE 54

Ethyl 2-[6-[(4-tert-butyl-2-thiazolyl)methoxyl]-2-pyridylcarbonylamino]-4-[3-(4-chlorophenylsulfonyl)propyl]phenoxyacetate Mass spectrometry data (m/z): 686 (M$^+$)

Nuclear magnetic resonance spectrum (CDCl$_3$, TMS internal standard)

δ: 1.21 (3H, t, J=7.2 Hz), 1.34 (9H, s), 2.01–2.08 (2H, m), 2.19 (2H, t, J=7.3 Hz), 3.06–3.10 (2H, m), 4.18 (2H, q, J=7.2 Hz), 4.65 (2H, s), 5.83 (2H, s), 7.76 (1H, d, J=8.4 Hz), 6.81 (1H, d, J=8.4 Hz), 6.90 (1H, s), 7.05 (1H, d, J=8.4 Hz), 7.52 (2H, d, J=8.4 Hz), 7.80–7.85 (3H, in), 7.92 (1H, d, J=7.2 Hz), 8.38 (1H, s), 10.6 (1H, s)

EXAMPLE 55

Ethyl 6-[3-[(4-tert-butyl-2-thiazolyl)methoxy]benzoylamino)-4-[3-(4-chlorophenylsulfonyl)propyl]-2,3-dichlorophenoxyacetate Mass spectrometry data (m/z): 755 [(M+H)$^+$]

Nuclear magnetic resonance spectrum (CDCl$_3$, TMS internal standard)

δ: 1.28 (3H, t, J=7.3 Hz), 1.35 (9H, s), 2.03–2.12 (2H, m), 2.90 (2H, br-d, J=7.3 Hz), 3.12–3.17 (2H, m), 4.31 (2H, q, J=7.3 Hz), 4.78 (2H, s), 5.47 (2H, s), 6.93 (1H, s), 7.24 (1H, br-d, J=8.3 Hz), 7.45 (1H, br-t, J=8.3 Hz), 7.54 (2H, d, J=8.8 Hz), 7.85 (1H, br-s), 7.86 (2H, d, J=8.8 Hz), 8.31 (1H, s) 10.14 (1H, br-s)

EXAMPLE 56

Ethyl 2-[3-[(4-tert-butyl-2-thiazolyl)methoxy]benzoylamino]-6-chloro-4-[3-(4-chlorophenylsulfonyl)propyl]phenoxyacetate Mass spectrometry data (m/z): 719 [(M+H)$^+$]

Nuclear magnetic resonance spectrum (CDCl$_3$, TMS internal standard)

δ: 1.16 (3H, t, J=7.3 Hz), 1.30 (9H, s), 1.78–1.87 (2H, m), 2.26–2.36 (2H, m), 3.33–3.38 (2H, m), 4.18 (2H, q, J=7.3 Hz), 4.82 (2H, s), 5.52 (2H, s), 7.10 (1H, br-s), 7.32–7.34 (2H, m), 7.51 (1H, br-t, J=7.8 Hz), 7.64 (1H, br-d, J=7.8 Hz), 7.72–7.75 (3H, m), 7.91 (2H, dd, J=8.8, 2.0 Hz), 10.14 (1H, br-s)

EXAMPLE 57

Ethyl 2-[2-[3-[(4-tert-butyl-2-thiazolyl)methoxy]benzoylamino]-4-[3-(4-chlorophenylsulfonyl)propyl]phenoxy]-2-fluoroacetate Mass spectrometry data (m/z): 703 [(M+H)$^+$]

Nuclear magnetic resonance spectrum (CDCl$_3$, TMS internal standard)

δ: 1.31 (3H, t, J=7.3 Hz), 1.36 (9H, s), 2.02–2.10 (2H, m), 2.71–2.75 (2H, br-t, J=7.3 Hz), 3.07–3.11 (2H, m), 4.36–4.43 (2H, m), 5.44 (2H, s), 5.83 (1H, d, J=58 Hz), 6.88 (1H, dd, J=8.3, 2.0 Hz), 6.93 (1H, s), 7.15 (1H, br-d, J=8.3 Hz), 7.22 (1H, dd, J=8.3, 2.0 Hz), 7.44 (1H, t, J=8.3 Hz), 7.52–7.59 (3H, m), 7.63 (1H, t, J=2.0 Hz), 7.82–7.89 (2H, m), 8.39 (1H, d, J=2.0 Hz), 8.75 (1H, s)

EXAMPLE 58

Ethyl 4-[3-(4-chlorophenylsulfonyl)propyl]-2-[3-[(4,5,6,7-tetrahydro-2-benzothiazolylmethoxy)benzoylamino]phenoxyacetate Mass spectrometry data (m/z): 683 (M$^+$)

Nuclear magnetic resonance spectrum (CDCl$_3$, TMS internal standard)

δ: 1.28 (3H, t, J=6.0 Hz), 1.83–1.90 (4H, m), 2.01–2.07 (2H, m), 2.69 (2H, t, J=6.0 Hz), 2.78–2.81 (4H, m), 3.07–3.10 (2H, m), 4.28 (2H, q, J=7.0 Hz), 4.70 (2H, s), 5.37 (2H, s), 6.82 (2H, s), 7.19 (1H, d, J=6.4 Hz), 7.42 (1H, t, J=6.4 Hz), 7.53 (2H, d, J=6.8 Hz), 7.62 (1H, d, J=6.4 Hz), 7.68 (1H, s), 7.82 (2H, d, J=6.8 Hz), 8.30 (1H, s), 9.22 (1H, s)

EXAMPLE 59 tert-Butyl 2-[3-[2-(4-tert-butyl-2-thiazolyl)ethoxy]benzoylamino]-4-[3-(4-chlorophenylsulfonyl)propyl]phenoxyacetate Nuclear magnetic resonance spectrum (CDCl$_3$, TMS internal standard)

δ: 1.34 (9H, s), 1.48 (9H, s), 1.98–2.07 (2H, m), 2.69 (2H, t, J=7.3 Hz), 3.06–3.10 (2H, m), 3.49 (2H, t, J=6.4 Hz), 4.32 (2H, t, J=6.4 Hz), 4.58 (2H, s), 6.77–6.83 (3H, m), 7.11 (1H, d, J=8.6 Hz), 7.40 (1H, t, J=8.0 Hz), 7.53 (2H, d, J=8.4 Hz), 7.58–7.60 (2H, m), 7.82 (2H, d, J=8.4 Hz), 8.29 (1H, s), 9.23 (1H, s)

The following compounds of Examples 60 to 72 were obtained in the same manner as described in Example 8.

EXAMPLE 60

4-[3-4-Chlorophenylsulfonyl)propyl]-2-[3-(4,5,6,7-tetrahydro-2-benzothiazolylmethoxy)benzoylamino]phenoxyacetic acid Melting point: 213° C.

Elemental analysis data (for $C_{32}H_{31}N_2S_2O_7Cl$)

|        | C (%) | H (%) | N (%) | S (%) | Cl (%) |
|--------|-------|-------|-------|-------|--------|
| calcd. | 58.66 | 4.77  | 4.28  | 9.79  | 5.41   |
| found  | 58.50 | 4.75  | 4.19  | 9.80  | 5.22   |

EXAMPLE 61

2-[3-[(4-tert-Butyl-2-thiazolyl)methoxy]-5-chlorobenzoylamino]-4-[3-(4-chlorophenylsulfonyl)propyl]phenoxyacetic acid Melting point: 143–145° C.

Elemental analysis data (for $C_{32}H_{32}N_2O_7S_2Cl_2$)

|        | C (%) | H (%) | N (%) | S (%) | Cl (%) |
|--------|-------|-------|-------|-------|--------|
| calcd. | 55.57 | 4.66  | 4.05  | 9.27  | 10.25  |
| found  | 55.59 | 4.59  | 4.14  | 9.33  | 10.17  |

EXAMPLE 62

2-[5-[(4-tert-Butyl-2-thiazolyl)methoxy]-2-chlorobenzoylamino]-4-[3-(4-chlorophenylsulfonyl)propyl]phenoxyacetic acid 0.85 hydrate Elemental analysis data (for $C_{32}H_{32}N_2S_2O_7Cl_2 \cdot 0.85H_2O$)

|        | C (%) | H (%) | N (%) | S (%) | Cl (%) |
|--------|-------|-------|-------|-------|--------|
| calcd. | 54.37 | 4.80  | 3.96  | 9.07  | 10.03  |
| found  | 53.97 | 4.40  | 3.91  | 9.03  | 10.00  |

Nuclear magnetic resonance spectrum (DMSO-$d_6$, TMS internal standard)

δ: 1.30 (9H, s), 1.75–1.85 (2H, m), 2.58–2.63 (2H, m), 3.34–3.38 (2H, m), 4.21 (2H, s), 5.46 (2H, s), 6.85 (1H, br-d, J=8.3 Hz), 6.96 (1H, br-d, J=8.3 Hz), 7.18 (1H, dd, J=8.8, 2.0 Hz), 7.33 (1H, s), 7.38 (1H, d, J=2.0 Hz), 7.45 (1H, br-d, J=8.8 Hz), 7.67 (1H, br-s), 7.73 (2H, br-d, J=8.3 Hz), 7.90 (1H, br-s), 7.91 (2H, br-d, J=8.3 Hz), 11.95 (1H, br-s)

EXAMPLE 63

2-[3-[(4-tert-Butyl-2-thiazolyl)methoxy]-4-methoxybenzoylamino]-4-[3-(4-chlorophenylsulfonyl)propyl]phenoxyacetic acid 0.5 hydrate Elemental analysis data (for $C_{33}H_{35}N_2S_2O_8Cl \cdot 0.5H_2O$)

|        | C (%) | H (%) | N (%) | S (%) | Cl (%) |
|--------|-------|-------|-------|-------|--------|
| calcd. | 56.93 | 5.21  | 4.02  | 9.21  | 5.09   |
| found  | 56.80 | 5.11  | 4.08  | 9.32  | 5.09   |

Nuclear magnetic resonance spectrum (DMSO-$d_6$, TMS internal standard)

δ: 1.30 (9H, s), 1.81–1.83 (2H, m), 2.61 (2H, br-t, J=7.8 Hz), 3.32–3.37 (2H, m), 3.88 (3H, s), 4.74 (2H, s), 5.45 (2H, s), 6.89 (1H, d, J=8.3 Hz), 6.99 (1H, d, J=8.3 Hz), 7.15 (1H, d, J=8.3 Hz), 7.31 (1H, s), 7.66 (1H, d, J=8.3 Hz), 7.73 (2H, br-d, J=8.3 Hz), 7.74 (1H, br-s), 7.78 (1H, d, J=1.5 Hz), 7.90 (2H, br-d, J=8.3 Hz), 9.50 (1H, s), 13.19 (1H, s)

EXAMPLE 64

2-[3-[(4-tert-Butyl-2-thiazolyl)methoxy]-4-chlorobenzoylamino]-4-[3-(4-chlorophenylsulfonyl)propyl]phenoxyacetic acid Melting point: 179.5–181.5° C.

Elemental analysis data (for $C_{32}H_{32}N_2S_2O_7Cl_2$)

|        | C (%) | H (%) | N (%) | S (%) | Cl (%) |
|--------|-------|-------|-------|-------|--------|
| calcd. | 55.47 | 4.66  | 4.05  | 9.27  | 10.25  |
| found  | 55.75 | 4.64  | 4.16  | 9.34  | 10.09  |

EXAMPLE 65

2-[3-[(4-tert-Butyl-2-thiazolyl)methoxy]-4-methylbenzoylamino]-4-[3-(4-chlorophenylsulfonyl)propyl]phenoxyacetic acid hydrate Elemental analysis data (for $C_{33}H_{35}N_2S_2O_7Cl \cdot H_2O$)

|        | C (%) | H (%) | N (%) | S (%) | Cl (%) |
|--------|-------|-------|-------|-------|--------|
| calcd. | 57.51 | 5.41  | 4.06  | 9.30  | 5.14   |
| found  | 57.79 | 5.33  | 4.05  | 9.34  | 4.99   |

Nuclear magnetic resonance spectrum (DMSO-$d_6$, TMS internal standard)

δ: 1.30 (9H, s), 1.75–1.87 (2H, m), 2.30 (3H, s), 2.61 (2H, br-t, J=7.8 Hz), 3.32–3.37 (2H, m), 4.74 (2H, s), 5.51 (2H, s), 6.91 (1H, d, J=8.3 Hz), 6.99 (1H, d, J=8.3 Hz), 7.31 (1H, s), 7.35 (1H, d, J=7.8 Hz), 7.53 (1H, d, J=7.8 Hz), 7.68 (1H, s), 7.73 (2H, br-d, J=8.3 Hz), 7.78 (1H, s), 7.90 (2H, br-d, J=8.3 Hz), 9.56 (1H, s), 13.20 (1H, s)

EXAMPLE 66

2-[3-[(4-tert-Butyl-2-thiazolyl)methoxy]-4-nitrobenzoylamino]-4-[3-(4-chlorophenylsulfonyl)propyl]phenoxyacetic acid 0.5 hydrate Melting point: 85.5–87.5° C.

Elemental analysis data (for $C_{32}H_{32}N_3S_2O_9Cl \cdot 0.5H_2O$)

|        | C (%) | H (%) | N (%) | S (%) | Cl (%) |
|--------|-------|-------|-------|-------|--------|
| calcd. | 54.04 | 4.68  | 5.91  | 9.02  | 4.98   |
| found  | 53.99 | 4.82  | 5.87  | 8.87  | 4.65   |

EXAMPLE 67

2-[6-(4-tert-Butyl-2-thiazolylmethoxy)-2-pyridylcarbonylamino]-4-[3-(4-chlorophenylsulfonyl)propyl]phenoxyacetic acid 0.5 hydrate Melting point: 169–171° C.

Elemental analysis data (for $C_{31}H_{32}N_3S_2O_7Cl \cdot 0.5H_2O$)

|        | C (%) | H (%) | N (%) | S (%) | Cl (%) |
|--------|-------|-------|-------|-------|--------|
| calcd. | 55.81 | 4.99  | 6.30  | 9.61  | 5.31   |
| found  | 55.99 | 4.85  | 6.19  | 9.58  | 5.39   |

EXAMPLE 68

6-[3-[(4-tert-Butyl-2-thiazolyl)methoxy]benzoylamino]-4-[3-(4-chlorophenylsulfonyl)propyl]-2,3-dichlorophenoxyacetic acid Melting point: 191–193° C.

Elemental analysis data (for $C_{32}H_{31}N_2O_7S_2Cl_3$)

|  | C (%) | H (%) | N (%) | S (%) | Cl (%) |
|---|---|---|---|---|---|
| calcd. | 52.93 | 4.30 | 3.86 | 8.83 | 14.65 |
| found | 52.80 | 4.40 | 3.83 | 8.84 | 14.53 |

EXAMPLE 69

2-[3-[(4-tert-Butyl-2-thiazolyl)methoxy]benzoylamino]-6-chloro-4-[3-(4-chlorophenylsulfonyl)propyl]phenoxyacetic acid Melting point: 201–203° C.

Elemental analysis data (for $C_{32}H_{32}N_2O_7S_2Cl_2$)

|  | C (%) | H (%) | N (%) | S (%) | Cl (%) |
|---|---|---|---|---|---|
| calcd. | 55.57 | 4.66 | 4.05 | 9.27 | 10.25 |
| found | 55.32 | 4.65 | 4.27 | 9.19 | 10.43 |

EXAMPLE 70

2-[3-[(4-tert-Butyl-2-thiazolyl)methoxy]thiobenzoylamino]-4-[3-(4-chlorophenylsulfonyl)propyl]phenoxyacetic acid 0.5 hydrate Elemental analysis data (for $C_{32}H_{33}N_2S_3O_6Cl_2.0.5H_2O$)

|  | C (%) | H (%) | N (%) | S (%) | Cl (%) |
|---|---|---|---|---|---|
| calcd. | 56.33 | 5.02 | 4.11 | 14.10 | 5.20 |
| found | 56.41 | 4.84 | 4.01 | 13.86 | 4.99 |

Nuclear magnetic resonance spectrum (DMSO-$d_6$, TMS internal standard)

δ: 1.30 (9H, s), 1.79–1.83 (2H, m), 2.63 (2H, t, J=7.3 Hz), 3.33–3.36 (2H, m), 4.68 (2H, s), 5.48 (2H, s), 7.00 (1H, d, J=8.4 Hz), 7.07 (1H, d, J=8.4 Hz), 7.24 (1H, d, J=8.4 Hz), 7.32 (1H, s), 7.40 (1H, t, J=8.0 Hz), 7.52–7.59 (3H, m), 7.73 (2H, d, J=8.3 Hz), 7.89 (2H, d, J=8.3 Hz), 11.2 (1H, s), 13.1 (1H, s)

EXAMPLE 71

2-[N-[3-[(4-tert-Butyl-2-thiazolyl)methoxy]benzoyl]-N-methylamino]-4-[3-(4-chlorophenylsulfonyl)propyl]phenoxyacetic acid Elemental analysis data (for $C_{33}H_{35}N_2S_2O_7Cl.H_2O$)

|  | C (%) | H (%) | N (%) | S (%) | Cl (%) |
|---|---|---|---|---|---|
| calcd. | 59.05 | 5.26 | 4.17 | 9.55 | 5.28 |
| found | 58.67 | 5.19 | 4.13 | 9.45 | 5.12 |

Nuclear magnetic resonance spectrum (DMSO-$d_6$, TMS internal standard)

δ: 1.29 (9H, s), 1.56–1.68 (2H, m), 2.35–2.60 (2H, m), 2.94–3.15 (2H, m), 3.23 (3H, s), 4.67 (2H, s), 5.23 (2H, m), 6.74–7.07 (7H, m), 7.28 (1H, m), 7.73 (2H, d, J=8.3 Hz), 7.84 (2H, d, J=8.3 Hz), 13.1 (1H, s)

EXAMPLE 72

2-[3-[(4-tert-Butyl-5-methyl-2-thiazolyl)methoxy]benzoylamino]-4-[3-(4-chlorophenylsulfonyl)propyl]phenoxyacetic acid 0.5 hydrate Elemental analysis data (for $C_{33}H_{35}N_2S_2O_7Cl.0.5H_2O$)

|  | C (%) | H (%) | N (%) | S (%) | Cl (%) |
|---|---|---|---|---|---|
| calcd. | 58.27 | 5.33 | 4.12 | 9.43 | 5.21 |
| found | 58.66 | 5.34 | 4.07 | 9.09 | 5.00 |

Nuclear magnetic resonance spectrum (DMSO-$d_6$, TMS internal standard)

δ: 1.36 (9H, s), 1.79–1.85 (2H, m), 2.51 (3H, s), 2.61 (2H, br-t, J=7.3 Hz), 3.32–3.37 (2H, m), 4.74 (2H, s), 5.37 (2H, s), 6.91 (1H, br-d, J=7.3 Hz), 7.00 (1H, d, J=7.3 Hz), 7.28 (1H, dd, J=8.3, 2.0 Hz), 7.47 (1H, t, J=8.3 Hz), 7.59 (1H, br-d, J=8.3 Hz), 7.63 (1H, br-s), 7.73 (2H, d, J=8.3 Hz), 7.79 (1H, br-s), 7.90 (2H, d, J=8.3 Hz), 9.65 (1H, s), 13.20 (1H, br-s)

The following compounds of Examples 73 and 74 were obtained in the same manner as described in Example 38.

EXAMPLE 73

3-(4-tert-Butyl-2-thiazolylmethoxy)-5'-[3-(phenylsulfonyl)propyl]-2'-(1H-tetrazol-5-ylmethoxy)benzanilide Elemental analysis data (for $C_{32}H_{34}N_6S_2O_5$)

|  | C (%) | H (%) | N (%) | S (%) |
|---|---|---|---|---|
| calcd. | 59.42 | 5.30 | 12.99 | 9.92 |
| found | 59.02 | 5.28 | 12.85 | 10.01 |

Nuclear magnetic resonance spectrum (DMSO-$d_6$, TMS internal standard)

δ: 1.30 (9H, s), 1.76–1.84 (2H, m), 2.61 (2H, t, J=7.3 Hz), 3.28–3.31 (2H, m), 5.47 (2H, s), 5.55 (2H, s), 6.95 (1H, d, J=8.0 Hz), 7.15 (1H, d, J=8.8 Hz), 7.28–7.33 (2H, m), 7.47 (1H, t, J=8.0 Hz), 7.55 (1H, d, J=7.6 Hz), 7.61 (1H, s), 7.64–7.69 (3H, m), 7.70–7.77 (1H, m), 7.89 (2H, d, J=7.2 Hz), 9.48 (1H, s)

EXAMPLE 74

5'-[3-(4-Chlorophenylsulfonyl)propyl]-3-[(4-cyclobutyl-2-thiazolyl)methoxy]-2'-(1H-tetrazol-5-ylmethoxy)benzanilide Melting point: 178.5–180.0° C.

Elemental analysis data (for $C_{32}H_{31}N_6S_2O_5Cl$)

|  | C (%) | H (%) | N (%) | S (%) | Cl (%) |
|---|---|---|---|---|---|
| calcd. | 56.59 | 4.60 | 12.37 | 9.44 | 5.22 |
| found | 56.62 | 4.60 | 12.39 | 9.54 | 5.14 |

EXAMPLE 75

A mixture of ethyl 2-[3-[(4-tert-butyl-2-thiazolyl)methoxy]benzoylamino]-4-[3-(4-chlorophenylsulfonyl)propyl]phenoxyacetate (176 mg, 0.26 mmol), diphosphorus pentasulfide (69 mg, 0.31 mmol), sodium bicarbonate (28 mg, 0.33 mmol) and 1,2-dimethoxyethane (5 ml) was stirred for 5 hours with heating under reflux, and insoluble matter was removed by filtration. The resulting filtrate was diluted with ethyl acetate, washed with water and brine in that order, dried over anhydrous sodium sulfate, and then concentrated under reduced pressure. Thereafter, the resulting residue was purified by silica gel column chromatography (eluent= hexane:ethyl acetate=3:1–2:1) to give ethyl 2-[3-[(4-tert-butyl-2-thiazolyl)methoxy]thiobenzoylamino]-4-[3-(4-chlorophenylsulfonyl)propyl]phenoxyacetate (143 mg, 0.20 mmol, 78%).

Mass spectrometry data (m/z): 701 (M⁺)

Nuclear magnetic resonance spectrum (CDCl$_3$, TMS internal standard)

δ: 1.25 (3H, s), 1.35 (9H, s), 2.02–2.12 (2H, m), 2.73 (2H, t, J=7.2 Hz), 3.11–3.15 (2H, m), 4.25 (2H, q, J=7.2 Hz), 4.71 (2H, s), 5.43 (2H, s), 6.88–6.98 (3H, m), 7.15 (1H, d, J=8.4 Hz), 7.37 (1H, t, J=8.0 Hz), 7.54 (2H, d, J=8.8 Hz), 7.61 (1H, d, J=7.2 Hz), 7.68 (1H, s), 7.84 (2H, d, J=8.8 Hz), 8.79 (1H, s), 10.4 (1H, s)

EXAMPLE 76

Under ice-cooling, trifluoroacetic acid (1.2 ml) was added to a mixture of tert-butyl 2-[3-[2-(4-tert-butyl-2-thiazolyl)ethoxy]benzoylamino]-4-[3-(4-chlorophenylsulfonyl)propyl]phenoxyacetate (185 mg, 0.25 mmol) and dichloromethane (2 ml), and the resulting reaction solution was stirred at room temperature for 3 hours and then concentrated under reduced pressure. Saturated sodium bicarbonate aqueous solution was added to the resulting residue and the product formed was extracted with ethyl acetate. The extract was washed with brine, dried over anhydrous sodium sulfate, and then concentrated under reduced pressure. The resulting residue was dissolved in water, and the solution obtained was adjusted to pH 2 by adding 10% citric acid aqueous solution. Thereafter, the solid material formed was collected by filtration and purified by silica gel column chromatography (eluent=chloroform:methanol=50:1) to give 2-[3-[2-(4-tert-butyl-2-thiazolyl)ethoxy]benzoylamino]-4-[3-(4-chlorophenylsulfonyl)propyl]phenoxyacetic acid 0.5 hydrate (58 mg, 0.086 mmol, 34%).

Elemental analysis data (for C$_{33}$H$_{35}$N$_2$S$_2$O$_7$Cl.0.5H$_2$O)

|  | C (%) | H (%) | N (%) | S (%) | Cl (%) |
|---|---|---|---|---|---|
| calcd. | 58.27 | 5.33 | 4.12 | 9.43 | 5.21 |
| found | 58.56 | 5.30 | 4.12 | 9.53 | 4.90 |

Nuclear magnetic resonance spectrum (DMSO-d$_6$, TMS internal standard)

δ: 1.28 (9H, s), 1.78–1.87 (2H, m), 2.61 (2H, t, J=7.2 Hz), 3.30–3.35 (2H, m), 3.44 (2H, t, J=5.8 Hz), 4.41 (2H, t, J=5.8 Hz), 4.74 (2H, s), 6.91 (1H, d, J=7.6 Hz), 7.00 (1H, d, J=8.4 Hz), 7.12 (1H, s), 7.19 (1H, d, J=8.0 Hz), 7.45 (1H, t, J=7.8 Hz), 7.52–7.57 (2H, m), 7.73 (2H, d, J=8.3 Hz), 7.79–7.80 (1H, m), 7.89 (2H, d, J=8.3 Hz), 9.62 (1H, s), 13.2 (1H, s)

EXAMPLE 77

Under ice-cooling, ethyl 2-[3-[(4-tert-butyl-2-thiazolyl)methoxy]benzoylamino]-4-[3-(4-chlorophenylsulfonyl)propyl]phenoxyacetate (266 mg, 0.39 mmol) was added to a mixture of 60% sodium hydride (19 mg, 0.48 mmol) and dimethylformamide (2 ml), and the reaction solution was stirred at room temperature for 1 hour. The reaction solution was again cooled with ice, methyl iodide (29 μl, 0.47 mmol) was added, and the mixture was stirred at room temperature for 2 hours. Water was added to the reaction solution and the product formed was extracted with toluene. The extract was washed with water and brine in that order, dried over anhydrous sodium sulfate, and then concentrated under reduced pressure. Thereafter, the resulting residue was purified by silica gel column chromatography (eluent=chloroform:methanol=50:1) to give ethyl 2-[N-[3-[(4-tert-butyl-2-thiazolyl)methoxy]benzoyl]-N-methylamino]-4-[3-(4-chlorophenylsulfonyl)propyl]phenoxyacetate (213 mg, 0.31 mmol, 78%).

Mass spectrometry data (m/z): 699 [(M+H)⁺]

Nuclear magnetic resonance spectrum (CDCl$_3$, TMS internal standard)

δ: 1.29 (2H, t, J=6.8 Hz), 1.35 (9H, s), 1.75–1.85 (2H, m), 2.41–2.58 (2H, m), 2.69–2.86 (2H, m), 3.38 (3H, s), 4.26 (2H, q, J=8.8 Hz), 4.62 (2H, s), 5.18 (2H, br), 6.56–6.74 (2H, m), 6.80–7.10 (6H, m), 7.52 (2H, d, J=8.3 Hz), 7.57 (2H, d, J=8.3 Hz)

EXAMPLE 78

Dimethylformamide (13 ml) was added to a mixture of 3-[(4-tert-butyl-2-thiazolyl)methoxy]-5'-[3-(4-chlorophenylsulfonyl)propyl]-2'-cyanomethoxybenzanilide (1.30 g, 2.04 mmol), ammonium chloride (0.20 g, 4.08 mmol) and sodium azide (0.25 g, 4.08 mmol), and the resulting mixture was stirred at 70° C. for 12 hours. Ice and 5% sodium hydrogensulfate aqueous solution were added to the reaction solution and the product formed was extracted with ethyl acetate. The resulting organic layer was washed with water and brine in that order, dried over anhydrous magnesium sulfate, and then concentrated under reduced pressure. Thereafter, the resulting residue was purified by silica gel column chromatography (eluent=methanol:chloroform=5:100) and then crystallized from acetonitrile to give 3-[(4-tert-butyl-2-thiazolyl)methoxy]-5'-[3-(4-chlorophenylsulfonyl)propyl]-2'-(1H-tetrazol-5-ylmethoxy)benzanilide (1.02 g, 74%) as colorless crystals.

Melting point: 161–163° C.

Elemental analysis data (for C$_{32}$H$_{33}$N$_6$O$_5$S$_2$Cl)

|  | C (%) | H (%) | N (%) | S (%) | Cl (%) |
|---|---|---|---|---|---|
| calcd. | 56.42 | 4.88 | 12.34 | 9.41 | 5.20 |
| found | 56.27 | 4.90 | 12.38 | 9.43 | 5.18 |

The following compound of Example 79 was obtained in the same manner as described in Example 8.

EXAMPLE 79

2-[2-[3-[(4-tert-butyl-2-thiazolyl)methoxy]benzoylamino]-4-[3-(4-chlorophenylsulfonyl)propyl]phenoxy]-2-fluoroacetic acid hydrate Melting point: 88–90° C.

Elemental analysis data (for C$_{32}$H$_{32}$N$_2$FS$_2$O$_7$Cl.H$_2$O)

|  | C (%) | H (%) | N (%) | F (%) | S (%) |
|---|---|---|---|---|---|
| calcd. | 55.44 | 4.94 | 4.04 | 2.74 | 9.25 |
| found | 55.55 | 5.00 | 4.02 | 2.54 | 9.28 |

EXAMPLE 80

A mixture of 5'-[3-(4-chlorophenylsulfonyl)propyl]-2'-hydroxy-3-(6-methoxy-2-benzothiazolylmethoxy)benzanilide (301 mg, 0.48 mmol), potassium carbonate (135 mg, 0.98 mmol), ethyl bromoacetate (81 mg, 0.49 mmol) and dimethylformamide (5 ml) was stirred at room temperature for 12 hours. Water was added to the reaction solution and the product formed was extracted with ethyl acetate. The extract was washed with water and brine in that order, dried over anhydrous sodium sulfate, and then concentrated under reduced pressure. Tetrahydrofuran (2 ml), methanol (1 ml) and 1 N sodium hydroxide were added to the resulting residue and the mixture was stirred at room temperature for 12 hours. The reaction solution was concentrated, and water was added to the resulting residue, and the mixture was adjusted to pH 3 with 10% citric acid aqueous solution.

Thereafter, the solid material formed was collected by filtration and washed with acetonitrile to give 4-[3-(4-chlorophenylsulfonyl)propyl]-2-[3-[(6-methoxy-2-benzothiazolyl)methoxy]benzoylamino]phenoxyacetic acid (145 mg, 0.21 mmol, 44%).

Melting point: 187–189° C.

Elemental analysis data (for $C_{33}H_{29}N_2S_2O_8Cl$)

|       | C (%) | H (%) | N (%) | S (%) | Cl (%) |
|-------|-------|-------|-------|-------|--------|
| calcd.| 58.19 | 4.29  | 4.11  | 9.41  | 5.20   |
| found | 58.09 | 4.48  | 4.12  | 9.46  | 5.00   |

Structures of the compounds of Examples 43 to 80 are shown in Tables 31 to 38.

EXAMPLE 81

Under ice-cooling, ethyl bromoacetate (87 mg, 0.52 mmol) was added dropwise to a mixture of 4-[2-(2-benzothiazolyl)vinyl]-5'-[3-(4-chlorophenylsulfonyl)propyl]-2'-hydroxybenzanilide (307 mg, 0.52 mmol), potassium carbonate (145 mg, 1.05 mmol) and dimethylformamide (10 ml), and the resulting reaction solution was stirred at room temperature for 12 hours. Water was added to the reaction solution and the product formed was extracted with ethyl acetate. The resulting extract was washed with water and brine in that order, dried over anhydrous sodium sulfate, and then concentrated under reduced pressure. Thereafter, the resulting residue was purified by silica gel column chromatography (eluent= hexane:ethyl acetate=4:1) to give ethyl 2-[4-[2-(2-benzothiazolyl)vinyl]benzoylamino]-4-[3-(4-chlorophenylsulfonyl)propyl]phenoxyacetate (219 mg, 0.32 mmol, 62%) as colorless solid.

The following compounds of Examples 82 to 89 were synthesized in the same manner as described in Example 81. Structures and physicochemical properties of these compounds are shown in Tables 21 to 24.

In this connection, the binding position shown in the tables means a binding position of

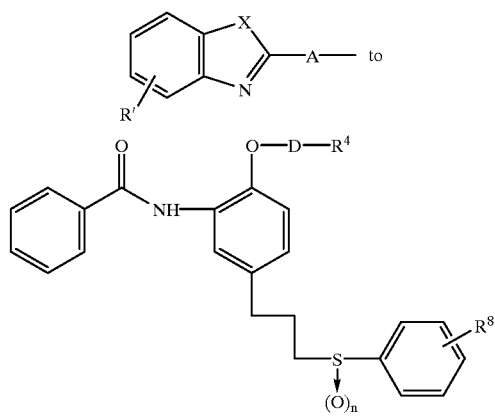

of the general formula (I). The same shall apply hereinafter.

EXAMPLE 82

Ethyl 2-[3-(2-benzothiazolylmethoxy)benzoylamino]-4-[3-(4-chlorophenylsulfonyl)propyl]phenoxyacetate

EXAMPLE 83

Ethyl 2-[3-[2-(2-benzothiazolyl)vinyl]benzoyl]amino]-4-[3-(4-chlorophenylsulfonyl)propyl]phenoxyacetate

EXAMPLE 84

Ethyl 2-[3-[(2-benzothiazolyl)thiomethyl]benzoylamino]-4-[3-(4-chlorophenylsulfonyl)propyl]phenoxyacetate

EXAMPLE 85

Ethyl 2-[3-[2-(5-chloro-2-benzothiazolyl)vinyl]benzoylamino]-4-[3-(4-chlorophenylsulfonyl)propyl]phenoxyacetate

EXAMPLE 86

Ethyl 2-[3-(2-benzoxazolylmethoxy)benzoylamino]-4-[3-(4-chlorophenylsulfonyl)propyl]phenoxyacetate

EXAMPLE 87

Ethyl 2-[3-(5-chloro-2-benzothiazolylmethoxy)benzoylamino]-4-[3-(4-chlorophenylsulfonyl)propyl]phenoxyacetate

EXAMPLE 88

Ethyl 4-[3-(4-chlorophenylsulfonyl)propyl]-2-[3-(5-trifluoromethyl-2-benzothiazolylmethoxy)benzoylamino]phenoxyacetate 0.5 hydrate

EXAMPLE 89

1,1-Dimethylethyl 2-[3-(2-benzothiazolylmethoxy)benzoylamino]-4-[3-(4-chlorophenylsulfonyl)propyl]phenoxyacetate

EXAMPLE 90

10% Sodium hydroxide aqueous solution (6 ml) was added at room temperature to a mixture of ethyl 2-[4-[2-(2-benzothiazolyl)vinyl]benzoylamino]-4-[3-(4-chlorophenylsulfonyl)propyl]phenoxyacetate (196 mg, 0.29 mmol) and tetrahydrofuran (10 ml), and the reaction solution was stirred at room temperature for 2 hours. The reaction solution was concentrated under reduced pressure, water was added the resulting residue, and then the solution was adjusted to pH 1 by adding concentrated hydrochloric acid. Thereafter, the solid material formed was collected by filtration, washed with water and ether in that order, dried under reduced pressure and then recrystallized from ethanol (50 ml) to give 2-[4-[2-(2-benzothiazolyl)vinyl]benzoylamino]-4-[3-(4-chlorophenylsulfonyl)propyl]phenoxyacetic acid (156 mg, 0.24 mmol, 83%) as colorless crystals.

The following compounds of Examples 91 to 97 represented by the general formula (I) were synthesized in the same manner as described in Example 90. Structures and physicochemical properties of these compounds are shown in Tables 25 and 26.

EXAMPLE 91

2-[3-(2-Benzothiazolylmethoxy)benzoylamino]-4-[3-(4-chlorophenylsulfonyl)propyl]phenoxyacetic acid-0.3H$_2$O

EXAMPLE 92

2-[3-[2-(2-Benzothiazolyl)vinyl]benzoyl]amino]-4-[3-(4-chlorophenylsulfonyl)propyl]phenoxyacetic acid-0.5H$_2$O

EXAMPLE 93

2-[3-[(2-Benzothiazolyl)thiomethyl]benzoylamino]-4-[3-(4-chlorophenylsulfonyl)propyl]phenoxyacetic acid

EXAMPLE 94

2-[3-[2-(5-Chloro-2-benzothiazolyl)vinyl]benzoylamino]-4-[3-(4-chlorophenylsulfonyl)propyl]phenoxyacetic acid-0.5H$_2$O

EXAMPLE 95

2-[3-(2-Benzoxazolylmethoxy)benzoylamino]-4-[3-(4-chlorophenylsulfonyl)propyl]phenoxyacetic acid

EXAMPLE 96

2-[3-(5-Chloro-2-benzothiazolylmethoxy)benzoylamino]-4-[3-(4-chlorophenylsulfonyl)propyl]phenoxyacetic acid

EXAMPLE 97

4-[3-(4-Chlorophenylsulfonyl)propyl]-2-[3-(5-trifluoromethyl-2-benzothiazolylmethoxy)benzoylamino]phenoxyacetic acid.hydrate The following compounds of Examples 98 to 102 were synthesized in the same manner as described in Example 81. Structures and physicochemical properties of these compounds are shown in Tables 27 and 28.

EXAMPLE 98

Ethyl 2-[3-(6-chloro-2-benzothiazolylmethoxy)benzoylamino]-4-[3-(4-chlorophenylsulfonyl)propyl]phenoxyacetate

EXAMPLE 99

Ethyl 2-[3-[2-(2-benzothiazolyl)ethyl]benzoylamino]-4-[3-(4-chlorophenylsulfonyl)propyl]phenoxyacetate

EXAMPLE 100

2-[2-[3-(2-Benzothiazolylmethoxy)benzoylamino]-4-[3-(4-chlorophenylsulfonyl)propyl]phenoxy]acetamide

EXAMPLE 101

3-[2-(2-Benzothiazolylmethoxy)benzoylamino]-5'-[3-(4-chlorophenylsulfonyl)propyl]-2'-(cyanomethoxy)benzanilide

EXAMPLE 102

Ethyl 2-[3-(2-benzoxazolylmethylthio)benzoylamino]-4-[3-(4-chlorophenylsulfonyl)propyl]phenoxyacetate The following compounds of Examples 103 to 106 were synthesized in the same manner as described in Example 90. Structures and physicochemical properties of these compounds are shown in Table 29.

EXAMPLE 103

2-[3-(6-Chloro-2-benzothiazolylmethoxy)benzoylamino]-4-[3-(4-chlorophenylsulfonyl)propyl]phenoxyacetic acid 0.5 hydrate

EXAMPLE 104

2-[3-[2-(2-benzothiazolyl)ethyl]benzoylamino]-4-[3-(4-chlorophenylsulfonyl)propyl]phenoxyacetic acid 0.3 hydrate

EXAMPLE 105

2-[3-(2-Benzothiazolylmethylthio)benzoylamino]-4-[3-(4-chlorophenylsulfonyl)propyl]phenoxyacetic acid

EXAMPLE 106

N-[[2-[3-(2-Benzothiazolylmethoxy)benzoylamino]-4-[3-(4-chlorophenylsulfonyl)propyl]phenoxy]acetyl]glycine

EXAMPLE 107

A mixture of 2-[3-(2-benzothiazolylmethoxy)benzoylamino]-4-[3-(4-chlorophenylsulfonyl)propyl]phenoxyacetic acid (200 mg, 0.31 mmol), methanesulfonamide (31 mg), 4-dimethylaminopyridine (45 mg), 1-ethyl-3-(3-dimethylaminopropyl)-carbodiimide hydrochloride (125 mg) and dichloromethane (10 ml) was stirred at room temperature for 3 days. The reaction solution was washed with 1 N hydrochloric acid, water and brine in that order, dried over anhydrous sodium sulfate, and then concentrated under reduced pressure. By recrystallizing the resulting solid material from acetonitrile (2 ml), 2-[2-[3-(2-benzothiazolylmethoxy)benzoylamino]-4-[3-(4-chlorophenylsulfonyl)propyl]phenoxy]-N-(methanesulfonyl)acetamide 0.5 hydrate (70 mg, 0.096 mmol, 31%) was obtained as colorless crystals.

Melting point: 153° C.

Elemental analysis data (for $C_{33}H_{30}N_3O_8S_3Cl.0.5H_2O$)

|  | C (%) | H (%) | N (%) | S (%) | Cl (%) |
|---|---|---|---|---|---|
| calcd. | 53.76 | 4.24 | 5.70 | 13.05 | 4.81 |
| found | 53.95 | 4.11 | 5.82 | 13.00 | 4.85 |

The following compound was synthesized in the same manner as described in Example 107.

EXAMPLE 108

2-[2-[3-(2-benzothiazolylmethoxy)benzoylamino]-4-[3-(4-chlorophenylsulfonyl)propyl]phenoxy]-N-(2-methylphenylsulfonyl)acetamide Melting point: 157° C.

Elemental analysis data (for $C_{39}H_{34}N_3O_8S_3Cl$)

|  | C (%) | H (%) | N (%) | S (%) | Cl (%) |
|---|---|---|---|---|---|
| calcd. | 58.24 | 4.26 | 5.22 | 11.96 | 4.41 |
| found | 58.26 | 4.25 | 5.22 | 12.04 | 4.59 |

EXAMPLE 109

Under ice-cooling, triethylamine (220 μl) was added to a mixture of 2-[3-(2-benzothiazolylmethoxy)benzoylamino]-4-[3-(4-chlorophenylsulfonyl)propyl]phenoxyacetic acid (400 mg, 0.62 mmol), glycine amide hydrochloride (86 mg), 1-hydroxybenzotriazole (125 mg), 1-ethyl-3-(3-dimethylaminopropyl)-carbodiimide hydrochloride (130 mg) and N,N-dimethylformamide (10 ml), and the mixture prepared was stirred at room temperature for 12 hours. Water and ethyl acetate were added to the reaction solution. The insoluble solid material formed was collected by filtration, washed with ethyl acetate, water, 1 N hydrochloric acid, water, ether, 1 N sodium hydroxide aqueous solution, water and ether in that order and then dried under reduced pressure. Acetonitrile (13 ml) was added to the resulting solid material, and the mixture was heated under reflux for 5 minutes with stirring and then cooled. The crystals formed were collected by filtration to give N-[[2-[3-(2-benzothiazolylmethoxy)benzoylamino]-4-[3-(4-chlorophenylsulfonyl)propyl]phenoxy]acetyl]glycine amide (170 mg, 0.24 mmol, 39%) as colorless crystals.

Melting point: 186–188° C.

Elemental analysis data (for $C_{34}H_{31}N_4O_7S_2Cl$)

|  | C (%) | H (%) | N (%) | S (%) | Cl (%) |
|---|---|---|---|---|---|
| calcd. | 57.74 | 4.42 | 7.92 | 9.07 | 5.01 |
| found | 57.57 | 4.32 | 7.91 | 9.29 | 4.89 |

The following compound was synthesized in the same manner as described in Example 109.

EXAMPLE 110

Ethyl N-[[2-[3-(2-benzothiazolylmethoxy)benzoylamino]-4-[3-(4-chlorophenylsulfonyl)propyl]phenoxy]acetyl]glycine.hydrate Melting point: 132–133° C.

Elemental analysis data (for $C_{36}H_{34}N_3O_8S_2Cl \cdot H_2O$)

|  | C (%) | H (%) | N (%) | S (%) |
|---|---|---|---|---|
| calcd. | 57.33 | 4.81 | 5.57 | 8.50 |
| found | 57.68 | 4.54 | 5.55 | 8.60 |

EXAMPLE 111

A mixture of 3-[2-(2-benzothiazolylmethoxy)benzoylamino]-5'-[3-(4-chlorophenylsulfonyl)propyl]-2'-(cyanomethoxy)benzanilide (390 mg, 0.62 mmol), tributyltin azide (4.2 g) and toluene (6 ml) was stirred for 2 hours with heating under reflux. The reaction solution was cooled and concentrated under reduced pressure. Methanol (15 ml) and 1 N hydrochloric acid (15 ml) were added to the resulting residue, and the mixture was stirred at room temperature for 30 minutes. The reaction solution was concentrated under reduced pressure and water and hexane were added to the resulting residue. The insoluble solid material formed was collected by filtration and washed with 1 N hydrochloric acid and hexane in that order. Hexane (70 ml) was added to the resulting solid material, the resulting mixture was heated under reflux for 5 minutes with stirring and then cooled. The resulting solid material was collected by filtration, ethanol (60 ml) was added to the solid, and the mixture was heated under reflux for 5 minutes and cooled. The solid was collected by filtration to give 3-(2-benzothiazolylmethoxy)-5'-[3-(4-chlorophenylsulfonyl)propyl]-2'-(1H-tetrazol-5-ylmethoxy)benzanilide (270 mg, 0.39 mmol, 63%) as colorless crystals.

Melting point: 189–191° C.

Elemental analysis data (for $C_{32}H_{27}N_6O_5S_2Cl$)

|  | C (%) | H (%) | N (%) | S (%) | Cl (%) |
|---|---|---|---|---|---|
| calcd. | 56.93 | 4.03 | 12.45 | 9.50 | 5.25 |
| found | 56.64 | 3.94 | 12.31 | 9.42 | 5.28 |

Structures of the compounds of Examples 107 to 111 are shown in Tables 38 and 39.

TABLE 12

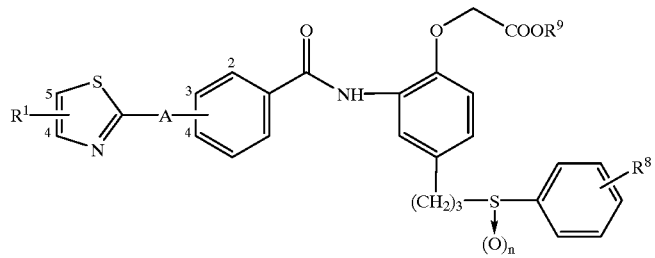

| Example No. | —A— | Binding position | $R^1$ | Binding position with thiazole ring | $R^8$ | n | $R^9$ | Physicochemical property |
|---|---|---|---|---|---|---|---|---|
| 1 | —CH=CH— | 3 | (phenyl) | 4 | 4-Cl | 2 | $C_2H_5$ | MS: (m/z)701(M⁺)NMR(CDCl₃) δ: 1.28(3H, t, J=7.3Hz), 2.00–2.09(2H, m), 2.71(2H, br-t, J=7.3Hz), 3.07–3.12 (2H, m), 4.35(2H, q, J=7.3Hz), 4.73(2H, s), 6.85(2H, s), 7.34(1H, br-t, J=7.3Hz), 7.37–7.50(3H, m), 7.51–7.56(5H, m), 7.71 (1H, br-d, J=7.8Hz), 7.68(2H, dd, J=6.9, 2.0Hz), 7.93(2H, d. J=7.3Hz), 7.99(1H, d, J=7.8Hz), 8.32(2H, d, J=8.3Hz), 9.43(1H, br-s) |
| 2 | —CH=CH— | 3 | (4-methylphenyl) | 4 | 4-Cl | 2 | $C_2H_5$ | MS: (m/z)715(M⁺)NMR(CDCl₃) δ: 1.28(3H, t, J=7.3Hz), 2.00–2.09(2H, m), 2.39(3H, s), 2.67–2.73(2H, m), 3.07–3.12(2H, m), 4.35(2H, q, J=7.3Hz), 4.72 (2H, s), 6.84(2H, s), 7.24(2H, d, J=7.7Hz), 7.37(1H, s), 7.50–7.55(5H, m), 7.75(1H, br-d, J=7.8Hz), 7.80–7.84(4H, m), 7.98(1H, br-d, J=7.8Hz), 8.32(2H, br-d, J=5.9Hz), 9.43(1H, br-s) |

TABLE 12-continued

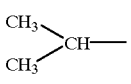

| Example No. | —A— | Binding position | $R^1$ | Binding position with thiazole ring | $R^8$ | n | $R^9$ | Physicochemical property |
|---|---|---|---|---|---|---|---|---|
| 3 | —CH=CH— | 3 | 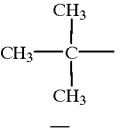 | 4 | 4-Cl | 2 | $C_2H_5$ | MS: (m/z)667(M⁺)NMR(CDCl₃) δ: 1.30(3H, t, J=7.3Hz), 1.34(6H, d, J=7.3Hz), 2.00–2.09(2H, m), 2.70(2H, br-t, J=7.3Hz), 3.07–3.13(3H, m), 4.34(2H, q, J=7.3Hz), 4.73(2H, s), 6.84(3H, br-s), 7.44(1H, d, J=16.1Hz), 7.47–7.54(4H, m), 7.68(1H, br-d, J=7.8Hz), 7.88(2H, dd, J=6.8, 2.0Hz), 7.96(1H, br-d, J=7.8Hz), 8.28(1H, br-s), 8.31(1H, br-s), 9.40(1H, br-s) |
| 4 | —CH=CH— | 3 | 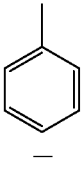 | 4 | 4-Cl | 2 | $C_2H_5$ | MS: (m/z)681(M⁺)NMR(CDCl₃) δ: 1.30(3H, t, J=7.3Hz), 1.38(9H, s), 2.00–2.09(2H, m), 2.70(2H, br-t, J=7.3Hz), 3.07–3.12(2H, m), 4.35(2H, q, J=7.3Hz), 4.73(2H, s), 6.84(3H, br-s), 7.43(1H, d, J=16.1Hz), 7.48–7.54(4H, m), 7.69(1H, br-d, J=7.8Hz), 7.83(2H, d, J=8.3Hz), 7.96(1H, br-d, J=7.8Hz), 8.29(1H, br-s), 8.31(1H, br-s), 9.40(1H, br-s) |

TABLE 13

| Example No. | —A— | Binding position | $R^1$ | Binding position with thiazole ring | $R^8$ | n | $R^9$ | Physicochemical property |
|---|---|---|---|---|---|---|---|---|
| 5 | —CH₂—O— | 3 | 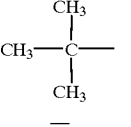 | 4 | 4-Cl | 2 | $C_2H_5$ | MS: (m/z)705(M⁺)NMR(CDCl₃) δ: 1.28(3H, t, J=7.3Hz), 1.99–2.08(2H, m), 2.69(2H, br-t, J=7.3Hz), 3.06–3.11(2H, m), 4.29(2H, q, J=7.3Hz), 4.69(2H, s), 5.53(2H, s), 6.82(2H, br-s), 7.24(1H, dd, J=8.3, 2.0Hz), 7.34(1H, m), 7.41–7.47(3H, m), 7.50–7.53(4H, m), 7.66(1H, br-d, J=7.8Hz), 7.60(1H, br-s), 7.82(2H, dt, J=8.8, 2.0Hz), 7.89(1H, br-s), 7.91(1H, br-s), 8.30(1H, br-s), 9.29(1H, br-s) |
| 6 | —CH₂—O— | 3 | 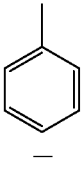 | 4 | 4-Cl | 2 | $C_2H_5$ | MS: (m/z)685(M⁺)NMR(CDCl₃) δ: 1.28(3H, t, J=7.3Hz), 1.35(9H, s), 2.00–2.08(2H, m), 2.69(2H, br-t, J=7.3Hz), 3.06–3.11(2H, m), 4.29(2H, q, J=7.3Hz), 4.71(2H, s), 5.44(2H, s), 6.82(2H, s), 6.93(1H, s), 7.21(1H, dd, J=8.3, 2.4Hz), 7.43(1H, t, J=8.3Hz), 7.52(2H, d, J=8.3Hz), 7.64(1H, br-d, J=8.3Hz), 7.72 (1H, br-s), 7.82(2H, d, J=8.3Hz), 8.30 (1H, br-s), 9.28(1H, br-s) |
| 7 | —CH=CH— | 3 | 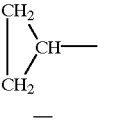 | 4 | 4-Cl | 2 | $C_2H_5$ | MS: (m/z)665(M⁺)NMR(CDCl₃) δ: 0.89–0.98(4H, m), 1.30(3H, t, J=7.3Hz), 2.00–2.08(3H, m), 2.70(2H, br-t, J=7.3Hz), 3.07–3.12(2H, m), 4.72(2H, s), 6.78(1H, s), 6.84(2H, br-s), 7.43(2H, br-s), 7.50(1H, br-t, J=7.8Hz), 7.53(2H, dd, J=6.8, 1.9Hz), 7.67(1H, br-d, J=7.8Hz), 7.83(2H, dd, J=6.8, 1.9Hz), 7.96(1H, br-d, J=7.8Hz), 7.83(2H, dd, J=6.8, 1.9Hz), 7.96(1H, br-d, 7.8Hz), 8.27 (1H, br-s), 8.30(1H, br-s), 9.39(1H, br-s) |

TABLE 14

Structure:

$R^1$-(thiazole, positions 4,5, S, N)-2-A-benzene(3)-C(=O)-NH-benzene-2-O-CH$_2$-COOH, with (CH$_2$)$_3$-S(=O)$_n$-C$_6$H$_4$-$R^8$ substituent

| Example No. | —A— | Binding position | $R^1$ | Binding position with thiazole ring | $R^8$ | n | Melting point (°C.) | Physicochemical property | | | | |
|---|---|---|---|---|---|---|---|---|---|---|---|---|
| 8 | —CH=CH— | 3 | phenyl | 4 | 4-Cl | 2 | 192–193 | ($C_{35}H_{29}N_2O_6S_2Cl$) | C(%) | H(%) | N(%) | S(%) Cl(%) |
| | | | | | | | | Calcd. | 62.44 | 4.34 | 4.16 | 9.53  5.27 |
| | | | | | | | | Found | 62.48 | 4.37 | 4.08 | 9.47  5.53 |
| 9 | —CH=CH— | 3 | 4-methylphenyl | 4 | 4-Cl | 2 | 198–200 | ($C_{36}H_{31}N_2O_6S_2Cl$) | C(%) | H(%) | N(%) | S(%) Cl(%) |
| | | | | | | | | Calcd. | 62.92 | 4.55 | 4.08 | 9.33  5.13 |
| | | | | | | | | Found | 62.84 | 4.53 | 4.06 | 9.21  5.38 |
| 10 | —CH=CH— | 3 | isopropyl | 4 | 4-Cl | 2 | 212–214 | ($C_{32}H_{31}N_2O_6S_2Cl$) | C(%) | H(%) | N(%) | S(%) Cl(%) |
| | | | | | | | | Calcd. | 60.14 | 4.89 | 4.38 | 10.03 5.55 |
| | | | | | | | | Found | 60.03 | 4.81 | 4.33 | 10.13 5.82 |
| 11 | —CH=CH— | 3 | tert-butyl | 4 | 4-Cl | 2 | 207–209 | ($C_{33}H_{33}N_2O_6S_2Cl$) | C(%) | H(%) | N(%) | S(%) Cl(%) |
| | | | | | | | | Calcd. | 60.68 | 5.09 | 4.29 | 9.82  5.43 |
| | | | | | | | | Found | 60.61 | 5.07 | 4.40 | 9.73  5.43 |
| 12 | —CH$_2$—O— | 3 | phenyl | 4 | 4-Cl | 2 | 175–177 | ($C_{34}H_{29}N_2O_7S_2Cl$) | C(%) | H(%) | N(%) | S(%) Cl(%) |
| | | | | | | | | Calcd. | 60.30 | 4.32 | 4.14 | 9.47  5.24 |
| | | | | | | | | Found | 60.32 | 4.24 | 4.12 | 9.28  5.46 |
| 13 | —CH$_2$—O— | 3 | tert-butyl | 4 | 4-Cl | 2 | 143–145 | ($C_{32}H_{33}N_2O_7S_2Cl$) | C(%) | H(%) | N(%) | S(%) Cl(%) |
| | | | | | | | | Calcd. | 58.48 | 5.06 | 4.26 | 9.76  5.39 |
| | | | | | | | | Found | 58.59 | 4.93 | 4.34 | 9.58  5.53 |

TABLE 14-continued

| Example No. | —A— | Binding position | $R^1$ | Binding position with thiazole ring | $R^8$ | n | Melting point (°C.) | Physicochemical property |
|---|---|---|---|---|---|---|---|---|
| 14 | —CH=CH— | 3 | 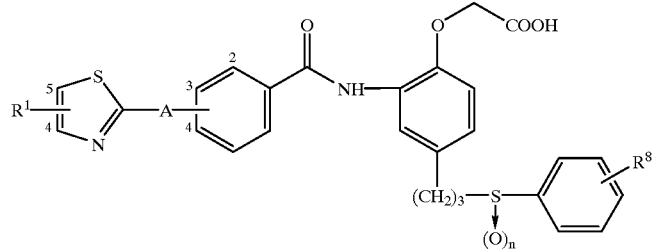 — | 4 | 4-Cl | 2 | 217–219 | NMR(DMSO-$d_6$) δ: 0.84–0.96(4H, m), 1.79–1.87(2H, m), 2.08–2.13(1H, m), 2.62(2H, br-t, J=7.8Hz), 3.36(2H, br-t, J=7.8Hz), 4.76 (2H, s), 6.93(1H, dd, J=8.3, 2.0Hz), 7.00 (1H, d, J=8.3Hz), 7.28(1H, s), 7.49(1H, d, J=16.1Hz), 7.54–7.59(3H, m), 7.73–7.79 (3H, m), 7.90–7.92(4H, m), 8.28(1H, br-s), 9.69(1H, br-s), 13.18(1H, br-s) |

TABLE 15

| Example No. | —A— | Binding position | $R^1$ | Binding position with thiazole ring | D | $R^4$ | n | Melting point (°C.) | Physicochemical property |
|---|---|---|---|---|---|---|---|---|---|
| 15 | —CH$_2$O— | 3 | 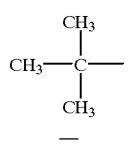 — | 4 | CH$_2$ | COOC$_2$H$_5$ | 2 | — | MS: (m/z)669(M$^+$) NMR δ: (CDCl$_3$)0.87–0.96(4H, m), 1.28(3H, t, J=7.3Hz), 2.00–2.08(2H, m), 2.69(2H, br-t, J=7.3Hz), 3.08(2H, br-t, J=7.9Hz), 4.28(2H, q, J=7.3Hz), 4.70(2H, s), 5.39(2H, s), 6.82(2H, s), 6.86(1H, s), 7.19(1H, dd, J=8.5, 2.4Hz), 7.43(1H, t, J=7.9Hz), 7.52(2H, br-d, J=8.6Hz), 7.64(1H, br-d, J=7.9Hz), 7.70(1H, br-s), 7.82(2H, br-d, J=8.6Hz), 8.30(1H, br-s), 9.26(1H, br-s) |
| 16 | —CH$_2$S— | 3 | CH$_3$—C(CH$_3$)(CH$_3$)— — | 4 | CH$_2$ | COOC$_2$H$_5$ | 2 | — | MS: (m/z)701(M$^+$) NMR δ: (CDCl$_3$)1.27(9H, s), 1.28(3H, t, J=7.3Hz), 2.01–2.05(1H, m), 2.69 (2H, br-t, J=7.3Hz), 3.06–3.11(2H, m), 4.28(2H, q, J=7.3Hz), 4.51(2H, s), 4.70 (2H, s), 6.78(1H, s), 6.82(2H, s), 7.39 (1H, t, J=7.8Hz), 7.53(2H, dd, J=6.4, 2.0Hz), 7.53(1H, br-d, J=6.4Hz), 7.82 (2H, dd, J=6.8, 2.0Hz), 7.82(1H, br-d, J=6.8Hz), 8.06(1H, br-s), 8.27(1H, br-s), 9.24(1H, br-s) |

TABLE 15-continued

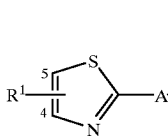

| Example No. | —A— | Binding position | R¹ | Binding position with thiazole ring | D | R⁴ | n | Melting point (° C.) | Physicochemical property |
|---|---|---|---|---|---|---|---|---|---|
| 17 | —CH₂—CH₂— | 3 | 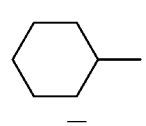 | 4 | CH₂ | COOC₂H₅ | 2 | — | MS: (m/z)683(M⁺)<br>NMR δ: (CDCl₃)1.28(3H, t, J=7.3Hz), 1.33(9H, s), 2.02–2.08(2H, m), 2.69 (2H, t, J=7.3Hz), 3.07–3.11(2H, m), 3.20(2H, br-t, J=9.3Hz), 3.36(2H, dd, J=9.3, 7.3Hz), 4.27(2H, q, J=7.3Hz), 4.70(2H, s), 6.71(1H, s), 6.81(2H, s), 7.38–7.43(2H, m), 7.53(2H, d, J=8.3Hz), 7.79–7.88(3H, m), 7.93(1H, br-s), 8.30(1H, br-s), 9.23(1H, br-s) |
| 18 | —CH₂O— | 3 | 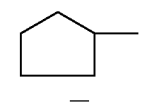 | 4 | CH₂ | COOC₂H₅ | 2 | — | MS: (m/z)711(M⁺)<br>NMR δ: (CDCl₃)1.28(3H, t, J=7.3Hz), 1.35–1.48(4H, m), 1.72–1.75(1H, m), 1.75–1.84(2H, m), 2.00–2.09(4H, m), 2.69(2H, t, J=7.3Hz), 2.74–2.79(1H, m), 3.07–3.10(2H, m), 4.28(2H, q, J=7.3Hz), 4.70(2H, s), 5.43(2H, s), 6.82(2H, s), 6.89(1H, s), 6.89(1H, s), 7.20(1H, dd, J=7.9, 2.4Hz), 7.43(1H, t, J=7.9Hz), 7.53(2H, d, J=8.6Hz), 7.64 (1H, br-d, J=7.9Hz), 7.71(1H, br-s), 7.82(2H, d, J=8.5Hz), 8.30(1H, br-s), 9.25(br-s) |

TABLE 16

| Example No. | —A— | Binding position | R¹ | Binding position with thiazole ring | D | R⁴ | n | Melting point (° C.) | Physicochemical property |
|---|---|---|---|---|---|---|---|---|---|
| 19 | —CH₂O— | 3 | 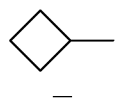 | 4 | CH₂ | COOC₂H₅ | 2 | — | MS: (m/z)697(M⁺)<br>NMR δ: (CDCl₃)1.28(3H, t, J=7.3Hz), 1.65–1.82(6H, m), 1.99–2.12(4H, m), 2.69(2H, br-t, J=7.3Hz), 3.06–3.11(2H, m), 3.18–3.25(1H, m), 4.28(2H, q, J=7.3Hz), 4.71(2H, s), 5.43(2H, s), 6.83(2H, s), 6.92(1H, s), 7.20(1H, dd, J=8.3, 2.4Hz), 7.26(1H, br-s), 7.43(1H, t, J=8.3Hz), 7.53(2H, d, J=8.3Hz), 7.71 (1H, br-s), 7.82(2H, d, J=8.3Hz), 8.30 (1H, br-s), 9.26(1H, br-s) |
| 20 | —CH₂O— | 3 |  | 4 | CH₂ | COOC₂H₅ | 2 | — | MS: (m/z)683(M⁺)<br>NMR δ: (CDCl₃)1.29(3H, t, J=7.3Hz), 1.88–1.95(1H, m), 1.99–2.08(3H, m), 2.23–2.31(2H, m), 2.34–2.40(2H, m), 2.70(2H, t, J=7.3Hz), 3.07–3.10(2H, m), 3.64–3.70(1H, m), 4.29(2H, q, J=7.3Hz), 4.71(2H, s), 5.44(2H, s), 6.82(2H, s), 6.93(1H, s), 7.20(1H, dd, J=7.9, 2.4Hz), 7.43(1H, t, J=7.9Hz), 7.53(2H, dd, J=8.6, 2.4Hz), 7.64(1H, br-d, J=7.3Hz), 7.70(1H, t, J=1.9Hz), 7.82(2H, dd, J=8.5, 2.4Hz), 8.30(1H, br-s), 9.25(1H, br-s) |

TABLE 16-continued

| Example No. | —A— | Binding position | R¹ | Binding position with thiazole ring | D | R⁴ | n | Melting point (° C.) | Physicochemical property |
|---|---|---|---|---|---|---|---|---|---|
| 21 | —CH(CH₃)—O— | 3 | CH₃—C(CH₃)(CH₃)— | 4 | CH₂ | COOC₂H₅ | 2 | — | MS: (m/z)699(M⁺) NMR δ: (CDCl₃)1.28–1.33(12H, m), 1.79(3H, d, J=6.4Hz), 2.01–2.06(2H, m), 2.69(2H, t, J=7.2Hz), 3.06–3.10 (2H, m), 4.30(2H, q, J=6.8Hz), 4.70 (2H, s), 5.80(1H, q, J=6.4Hz), 6.81–6.83(3H, m), 7.17(1H, dd, J=8.1, 2.2Hz), 7.38(1H, t, J=7.8Hz), 7.52–7.58 (3H, m), 7.67(1H, br-s), 7.82(2H, d, J=8.0Hz), 8.28(1H, br-s), 9.17(1H, br-s) |

TABLE 17

[Structure: thiazole (R¹ at 4/5 position) — A — benzamide with 2-position carbonyl, NH linked to phenyl ring bearing O—D—R⁴ and (CH₂)₃—S(→O)ₙ—C₆H₄—Cl]

| Example No. | —A— | Binding position | R¹ | Binding position with thiazole ring | D | R⁴ | n | Melting point (° C.) | Physicochemical property |
|---|---|---|---|---|---|---|---|---|---|
| 23 | —CH₂O— | 3 | CH₃—C(CH₃)(CH₃)— | 4 | (CH₂)₃ | COOC₂H₅ | 2 | — | MS: (m/z)713(M⁺) NMR(CDCl₃) δ: 1.18(3H, t, J=7.0Hz), 1.35(9H, s), 1.99–2.07(2H, m), 2.17–2.23(2H, m), 2.52(2H, br-t, J=7.0Hz), 2.68(2H, t, J=7.3Hz), 3.07–3.11(2H, m), 4.05(2H, br-q, J=7.0Hz), 4.11(2H, br-t, J=6.1Hz), 5.42(2H, s), 6.81(2H, br-s), 6.93(1H, s), 7.22(1H, br-dd, J=7.8, 2.4Hz), 7.43(1H, br-t, J=8.0Hz), 7.49(1H, br-d, J=7.8Hz), 7.53(2H, br-d, J=8.3Hz), 7.61(1H, s), 7.82(2H, br-d, J=8.8Hz), 8.29(1H, s), 8.55(1H, s) |
| 24 | —CH₂O— | 3 | CH₃—C(CH₃)(CH₃)— | 4 | —C(CH₃)(CH₃)— | COOC₂H₅ | 2 | — | MS: (m/z)712(M⁺) NMR δ: (CDCl₃)1.22(3H, br-t, J=7.0Hz), 1.35(9H, s), 1.66(6H, s), 2.01–2.07(2H, m), 2.69(2H, br-1, J=7.3Hz), 3.08–3.11(2H, m), 4.21–4.25 (2H, m), 5.44(2H, s), 6.74(1H, br-d, J=1.8Hz), 6.76(1H, br-d, J=2.5Hz), 6.93(1H, s), 7.21(1H, br-dd, J=7.9, 2.4Hz), 7.43(1H, t, J=7.9Hz), 7.53(2H, br-d, J=8.6Hz), 7.65(1H, d, J=7.9Hz), 7.69(1H, s), 7.83(2H, br-d, J=8.5Hz), 8.37(1H, br-s), 9.25(1H, s) |
| 25 | —CH₂O— | 3 | CH₃—C(CH₃)(CH₃)— | 4 | —CH(CH₃)— | COOC₂H₅ | 2 | — | MS: (m/z)698(M⁺) NMR δ: (CDCl₃)1.25(3H, br-t, J=7.3Hz), 1.35(9H, br-s), 1.71(3H, br-d, J=7.3Hz), 2.00–2.06(2H, m), 2.67–2.70(2H, m), 3.07–3.10(2H, m), 4.19–4.27(2H, m) 4.75–4.79(1H, m), 5.44 (2H, s), 6.79–6.84(2H, m), 6.92(1H, s), 7.20–7.22(1H, m), 7.43(1H, t, J=8.6Hz), 7.52–7.54(2H, m), 7.62(1H, d, J=7.9Hz), 7.73(1H, br-s), 7.81–7.83 (2H, m), 8.28(1H, br-s), 9.29(1H, br-s) |

TABLE 18

| Example No. | —A— | Binding position | R¹ | Binding position with thiazole ring | D | R⁴ | n | Melting point (° C.) | Physicochemical property |
|---|---|---|---|---|---|---|---|---|---|
| 26 | —CH₂O— | 3 | cyclopropyl | 4 | CH₂ | COOH | 2 | 165–167 | MS: (m/z)641(M⁺)<br>($C_{31}H_{29}N_2O_7S_2Cl$)<br>　　　C(%)　H(%)　N(%)　S(%)　Cl(%)<br>Calcd.　58.07　4.56　4.37　10.00　5.53<br>Found　57.77　4.51　4.37　10.10　5.82 |
| 27 | —CH₂S— | 3 | t-Bu | 4 | CH₂ | COOH | 2 | 158–159 | MS: (m/z)673(M⁺)<br>($C_{32}H_{33}N_2O_6S_3Cl$)<br>　　　C(%)　H(%)　N(%)　S(%)　Cl(%)<br>Calcd.　57.09　4.94　4.16　14.29　5.27<br>Found　57.01　4.85　4.14　14.50　5.33 |
| 28 | —CH₂CH₂— | 3 | t-Bu | 4 | CH₂ | COOH | 2 | 153–155 | MS: (m/z)655(M⁺)<br>($C_{33}H_{33}N_2O_6S_2Cl$)<br>　　　C(%)　H(%)　N(%)　S(%)　Cl(%)<br>Calcd.　60.49　5.38　4.28　9.79　5.41<br>Found　60.50　5.31　4.24　9.85　5.51 |
| 29 | —CH₂O— | 3 | cyclohexyl | 4 | CH₂ | COOH | 2 | 169–171 | MS: (m/z)683(M⁺)<br>($C_{34}H_{35}N_2O_7S_2Cl$)<br>　　　C(%)　H(%)　N(%)　S(%)　Cl(%)<br>Calcd.　59.77　5.16　4.10　9.39　5.19<br>Found　59.77　5.08　4.11　9.48　5.27 |
| 30 | —CH₂O— | 3 | cyclopentyl | 4 | CH₂ | COOH | 2 | 162–164 | MS: (m/z)669(M⁺)<br>($C_{33}H_{33}N_2O_7S_2Cl$)<br>　　　C(%)　H(%)　N(%)　S(%)　Cl(%)<br>Calcd.　59.23　4.97　4.19　9.58　5.30<br>Found　59.27　4.92　4.21　9.63　5.24 |
| 31 | —CH₂O— | 3 | cyclobutyl | 4 | CH₂ | COOH | 2 | 194–195 | MS: (m/z)655(M⁺)<br>($C_{32}H_{31}N_2O_7S_2Cl$)<br>　　　C(%)　H(%)　N(%)　S(%)　Cl(%)<br>Calcd.　58.66　4.77　4.28　9.79　5.41<br>Found　58.62　4.72　4.31　9.79　5.57 |
| 32 | CH₃—CH—O— | 3 | t-Bu | 4 | CH₂ | COOH | 2 | 70 | ($C_{33}H_{35}N_2O_7S_2Cl$)<br>　　　C(%)　H(%)　N(%)　S(%)　Cl(%)<br>Calcd.　59.05　5.26　4.17　9.55　5.28<br>Found　58.74　5.28　4.11　9.76　5.47 |

TABLE 19

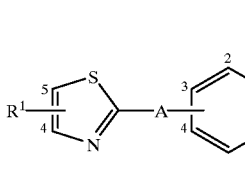

| Example No. | —A— | Binding position | R¹ | Binding position with thiazole ring | D | R⁴ | n | Melting point (° C.) | Physicochemical property |
|---|---|---|---|---|---|---|---|---|---|
| 34 | —CH₂O— | 3 |  | 4 | —(CH₂)₃— | COOH | 2 | 138.5–139.5 | MS: (m/z)685(M⁺)<br>(C₃₄H₃₇N₂O₇S₂Cl)<br>    C(%) H(%) N(%) S(%) Cl(%)<br>Calcd. 59.59 5.44 4.09 9.36 5.17<br>Found 59.40 5.35 4.16 9.31 5.33 |
| 35 | —CH₂O— | 3 | 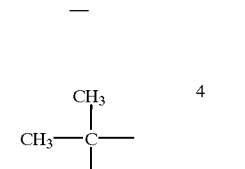 | 4 | 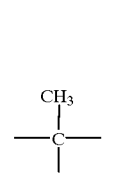 | COOH | 2 | — | MS: (m/z)685(M⁺)<br>(C₃₄H₃₇N₂O₇S₂Cl·0.5H₂O)<br>    C(%) H(%) N(%) S(%) Cl(%)<br>Calcd. 58.82 5.52 4.03 9.24 5.11<br>Found 58.77 5.49 3.89 9.02 5.11 |
| 36 | —CH₂O— | 3 | 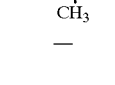 | 4 |  | COOH | 2 | — | MS: (m/z)671(M⁺)<br>(C₃₃H₃₅N₂O₇S₂Cl·0.5H₂O)<br>    C(%) H(%) N(%) S(%) Cl(%)<br>Calcd. 58.27 5.33 4.12 9.43 5.21<br>Found 58.26 5.33 3.97 9.41 5.11 |

TABLE 20

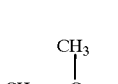

| Example No. | —A— | Binding position | R¹ | Binding position with thiazole ring | D | R⁴ | n | Melting point (° C.) | Physicochemical property |
|---|---|---|---|---|---|---|---|---|---|
| 39 | —CH₂O— | 3 | 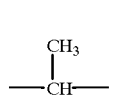 | 4 | CH₂ | 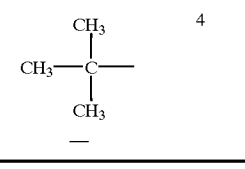 | 2 | 161–163 | MS: (m/z)681(M⁺)<br>(C₃₂H₃₃N₆O₅S₂Cl)<br>    C(%) H(%) N(%) S(%) Cl(%)<br>Calcd. 56.42 4.88 12.34 9.41 5.20<br>Found 56.27 4.90 12.38 9.43 5.18 |

TABLE 20-continued

[Structure: R¹-thiazole(5,4,N,S positions)-A-benzene(2,3,4)-C(=O)-NH-benzene-O-D-R⁴ with (CH₂)₃-S(=O)ₙ-C₆H₄-Cl substituent]

| Example No. | —A— | Binding position | R¹ | Binding position with thiazole ring | D | R⁴ | n | Melting point (° C.) | Physicochemical property |
|---|---|---|---|---|---|---|---|---|---|
| 40 | —CH₂S— | 3 | CH₃-C(CH₃)(CH₃)- | 4 | CH₂ | tetrazole (N–N=N–NH–) with CH₃ | 2 | — | MS: (m/z)697(M⁺) (C₃₂H₃₃N₆O₄S₃Cl·0.7H₂O)<br>C(%) H(%) N(%) S(%) Cl(%)<br>Calcd. 54.14 4.88 11.84 13.55 4.99<br>Found 54.50 4.91 11.83 13.15 4.99 |
| 41 | —CH₂CH₂— | 3 | cyclobutyl | 4 | CH₂ | tetrazole | 2 | 187.5–188.5 | MS: (m/z)677(M⁺) (C₃₃H₃₃N₆O₄S₂Cl)<br>C(%) H(%) N(%) S(%) Cl(%)<br>Calcd. 58.53 4.91 12.41 9.47 5.23<br>Found 58.26 4.82 12.37 9.45 5.23 |

TABLE 21

[Structure: benzo-fused X-N heterocycle(positions 4,5,6,7) with R'-A-benzene(2,3,4)-C(=O)-NH-benzene-O-CH₂-COOR⁹ with (CH₂)₃-SO₂-C₆H₄-Cl substituent]

| Example No. | X | —A— | Binding position | R' | R⁹ | Physicochemical property |
|---|---|---|---|---|---|---|
| 81 | S | —CH=CH— | 4 | H | CH₂CH₃ | Melting point: 127–129° C.<br>Elemental analysis (C₃₅H₃₁N₂O₆S₂Cl)<br>C(%) H(%) N(%) S(%) Cl(%)<br>Calcd. 62.26 4.63 4.15 9.50 5.25<br>Found 62.22 4.55 3.93 9.48 5.38 |
| 82 | S | —CH₂—O— | 3 | H | CH₂CH₃ | Melting point: 92–95° C.<br>Elemental analysis (C₃₄H₃₁N₂O₇S₂Cl)<br>C(%) H(%) N(%) S(%) Cl(%)<br>Calcd. 60.12 4.60 4.12 9.44 5.22<br>Found 59.96 4.63 3.98 9.39 5.47 |

TABLE 22

| Example No. | X | —A— | Binding position | R' | R⁹ | Physicochemical property |
|---|---|---|---|---|---|---|
| 83 | S | —CH=CH— | 3 | H | CH$_2$CH$_3$ | MS: (m/z) 675 (M⁺)<br>NMR (CDCl$_3$)<br>δ: 1.33 (3H, t, J=7.1Hz), 2.01–2.09 (2H, m), 2.71 (2H, t, J=7.2Hz), 3.08–3.12 (2H, m), 4.39 (2H, q, J=7.1Hz), 4.74 (2H, s), 6.86 (2H, br), 7.37–7.41 (1H, m), 7.47–7.58 (4H, m), 7.63 (2H, br), 7.74 (1H, d, J=8.0Hz), 7.82–7.89 (3H, m), 7.98–8.03 (2H, m), (1H, br), 8.37 (1H, br), 9.47 (1H, s) |
| 84 | S | —S—CH$_2$— | 3 | H | CH$_2$CH$_3$ | Melting point 94° C.<br>Elemental analysis (C$_{34}$H$_{31}$N$_2$O$_6$S$_2$Cl)<br>　　　　C (%)　H (%)　N (%)　S (%)　Cl (%)<br>Calcd.　58.74　4.49　4.03　13.84　5.10<br>Found　58.83　4.46　3.77　13.51　4.99 |

TABLE 23

| Example No. | X | —A— | Binding position | R' | R⁹ | Physicochemical property |
|---|---|---|---|---|---|---|
| 85 | S | —CH=CH— | 3 | 5-Cl | CH$_2$CH$_3$ | MS: (m/z) 709 (M⁺)<br>NMR (CDCl$_3$)<br>δ: 1.33 (3H, t, J=6.9Hz), 2.04–2.09 (2H, m), 2.72 (2H, t, J=7.3Hz), 3.08–3.11 (2H, m), 3.38 (2H, q, J=6.9Hz), 4.74 (2H, s), 6.86 (2H, br), 7.37 (1H, dd, J=8.5, 2.0Hz), 7.52–7.58 (3H, m), 7.61–7.62 (2H, m), 7.73 (1H, d, J=7.5Hz), 7.78 (1H, d, J=8.5Hz), 7.82–7.85 (2H, m), 7.96 (1H, d, J=1.5Hz), 8.03 (1H, d, J=8.0Hz), 8.31 (1H, br), 8.38 (1H, br), 9.47 (1H, s) |
| 86 | O | —CH$_2$—O— | 3 | H | CH$_2$CH$_3$ | MS: (m/z) 663 (M⁺)<br>NMR (CDCl$_3$)<br>δ: 1.27 (3H, t, J=7.1Hz), 2.00–2.07 (2H, m), 2.69 (2H, t, J=7.4Hz), 3.06–3.10 (2H, m), 4.26 (2H, q, J=7.1Hz), 4.69 (2H, s), 5.44 (2H, s), 6.82 (2H, br), 7.26–7.28 (1H, m), 7.35–7.40 (2H, m), 7.45 (1H, t, J=7.8Hz), 7.53–7.58 (3H, m), 7.66 (1H, d, J=8.0Hz), 7.75–7.78 (2H, m), 7.81–7.83 (2H, m), 8.30 (1H, br), 9.25 (1H, s) |

TABLE 24

| Example No. | X | —A— | Binding position | R' | R⁹ | Physicochemical property |
|---|---|---|---|---|---|---|
| 87 | S | —CH$_2$—O— | 3 | 5-Cl | CH$_2$CH$_3$ | MS: (m/z)713(M⁺)<br>NMR(CDCl$_3$)<br>δ: 1.30(3H, t, J=7.1Hz), 2.00–2.07(2H, m), 2.69(2H, t, J=7.4Hz), 3.06–3.10(2H, m), 4.29(2H, q, J=7.1Hz), 4.70 (2H, s), 5.58(2H, s), 6.83(2H, br), 7.22–7.26(1H, m), 7.39(1H, dd, J=8.8, 2.0Hz), 7.46(1H, t, J=8.0Hz), 7.53 (1H, d, J=8.4Hz), 7.67(1H, d, J=7.6Hz), 7.75(1H, br), 7.81–7.83(3H, m), 8.01(1H, d, J=2.0Hz), 8.29(1H, br), 9.30(1H, s)<br>Melting point: 140° C.<br>Elemental Analysis (C$_{35}$H$_{30}$N$_2$O$_7$S$_2$ClF$_3$·0.5H$_2$O) |
| 88 | S | —CH$_2$—O— | 3 | 5-CF$_3$ | CH$_2$CH$_3$ | 　　　　C(%)　H(%)　N(%)　S(%)　Cl(%)　F(%)<br>Calcd.　55.59　4.13　3.70　8.48　4.69　7.54<br>Found　55.61　4.09　3.67　8.72　4.79　7.54<br>Melting point: 81–83° C.<br>Elemental Analysis (C$_{36}$H$_{35}$N$_2$O$_7$S$_2$Cl) |
| 89 | S | —CH$_2$—O— | 3 | H | CH$_3$—C(CH$_3$)(CH$_3$)— | 　　　　C(%)　H(%)　N(%)　S(%)　Cl(%)<br>Calcd.　61.14　4.99　3.96　9.07　5.01<br>Found　60.98　4.85　3.88　9.24　5.07 |

TABLE 25

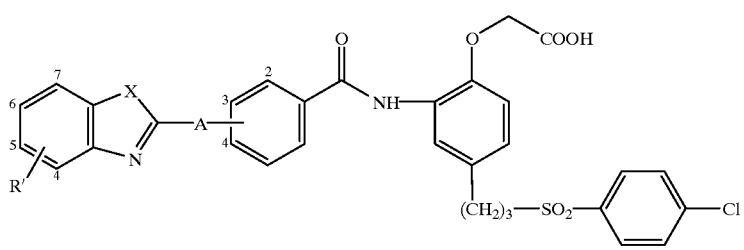

| Example No. | X | —A— | Binding position | R' | Melting Point | Elemental analysis | | | | |
|---|---|---|---|---|---|---|---|---|---|---|
| 90 | S | —CH=CH— | 4 | H | 202 | $C_{33}H_{27}N_2O_6S_2Cl \cdot H_2O$ | | | | |
| | | | | | | | C(%) | H(%) | N(%) | S(%) | Cl(%) |
| | | | | | | Calcd. | 59.59 | 4.39 | 4.21 | 9.64 | 5.33 |
| | | | | | | Found | 59.67 | 4.16 | 4.09 | 9.65 | 5.50 |
| 91 | S | —CH$_2$—O— | 3 | H | 207–209 | $C_{32}H_{27}N_2O_7S_2Cl \cdot 0.3H_2O$ | | | | |
| | | | | | | | C(%) | H(%) | N(%) | Cl(%) |
| | | | | | | Calcd. | 58.54 | 4.24 | 4.27 | 5.40 |
| | | | | | | Found | 58.57 | 4.14 | 4.23 | 5.42 |
| 92 | S | —CH=CH— | 3 | H | 246 | $C_{33}H_{27}N_2O_6S_2Cl \cdot 0.5H_2O$ | | | | |
| | | | | | | | C(%) | H(%) | N(%) | S(%) | Cl(%) |
| | | | | | | Calcd. | 60.40 | 4.30 | 4.27 | 9.77 | 5.40 |
| | | | | | | Found | 60.60 | 4.25 | 4.19 | 9.68 | 5.35 |

TABLE 26

| Example No. | X | —A— | Binding position | R' | Melting point | Elemental analysis | | | | | |
|---|---|---|---|---|---|---|---|---|---|---|---|
| 93 | S | —S—CH$_2$— | 3 | H | 213 | $C_{32}H_{27}N_2O_6S_3Cl$ | | | | | |
| | | | | | | | C (%) | H (%) | N (%) | S (%) | Cl (%) |
| | | | | | | Calcd. | 57.60 | 4.08 | 4.20 | 14.42 | 5.31 |
| | | | | | | Found | 57.60 | 4.06 | 4.17 | 14.11 | 5.48 |
| 94 | S | —CH=CH— | 3 | 5-Cl | 223–224 | $C_{33}H_{26}N_2O_6S_2Cl_2 \cdot 0.5H_2O$ | | | | | |
| | | | | | | | C (%) | H (%) | N (%) | S (%) | Cl (%) |
| | | | | | | Calcd. | 57.39 | 3.94 | 4.06 | 9.29 | 10.27 |
| | | | | | | Found | 57.61 | 3.75 | 3.90 | 9.04 | 10.45 |
| 95 | O | —CH$_2$—O— | 3 | H | 172 | $C_{32}H_{27}N_2O_8SCl \cdot 0.5H_2O$ | | | | | |
| | | | | | | | C (%) | H (%) | N (%) | S (%) | Cl (%) |
| | | | | | | Calcd. | 59.67 | 4.38 | 4.35 | 4.98 | 5.50 |
| | | | | | | Found | 59.77 | 4.33 | 4.31 | 4.90 | 5.50 |
| 96 | S | —CH$_2$—O— | 3 | 5-Cl | 204~206 | $C_{32}H_{26}N_2O_7S_2Cl_2$ | | | | | |
| | | | | | | | C (%) | H (%) | N (%) | S (%) | Cl (%) |
| | | | | | | Calcd. | 56.06 | 3.82 | 4.09 | 9.35 | 10.34 |
| | | | | | | Found | 26.00 | 3.82 | 4.08 | 9.12 | 10.48 |
| 97 | S | —CH$_2$—O— | 3 | 5-CF$_3$ | 195~196 | $C_{33}H_{26}N_2O_7S_2ClF_3 \cdot H_2O$ | | | | | |
| | | | | | | | C (%) | H (%) | N (%) | S (%) | Cl (%) | F (%) |
| | | | | | | Calcd. | 53.77 | 3.83 | 3.80 | 8.70 | 4.81 | 7.73 |
| | | | | | | Found | 53.98 | 3.91 | 3.65 | 8.64 | 4.66 | 7.58 |

TABLE 27

[Structure: benzoxazole/benzothiazole-A-phenyl-C(O)NH-phenyl(O-D-R⁴)(CH₂)₃SO₂-C₆H₄-Cl]

| Example No. | X | —A— | Binding position | R' | D | R⁴ | Melting point(° C.) | Physicochemical property |
|---|---|---|---|---|---|---|---|---|
| 98 | S | —CH₂O— | 3 | 6-Cl | CH₂ | COOC₂H₅ | 146–148 | Elemental analysis ($C_{34}H_{30}N_2O_7S_2Cl_2$)<br>　　　C(%)　H(%)　N(%)　S(%)　Cl(%)<br>Calcd.　57.22　4.24　3.93　8.99　9.94<br>Found　57.25　4.15　3.99　8.86　9.86<br>MS: (m/z)677(M⁺) |
| 99 | S | —CH₂CH₂— | 3 | H | CH₂ | COOC₂H₅ | — | NMR(CDCl₃)<br>δ: 1.26(3H, t, J=7.0Hz), 2.01–2.07(2H, m), 2.70 (2H, t, J=7.5Hz), 3.07–3.10(2H, m), 3.22(2H, t, J=8.3Hz), 3.50–3.53(2H, m), 4.26(2H, q, J=7.0Hz), 4.69(2H, s), 6.82(2H, br), 7.36(2H, t, J=7.8Hz), 7.42–7.48(3H, m), 7.52(2H, d, J=8.6Hz), 7.80–7.87 (4H, m), 7.98–8.00(3H, m), 8.31(1H, br), 9.25(1H, br) |
| 100 | S | —CH₂O— | 3 | H | CH₂ | CONH₂ | 179 | Elemental analysis ($C_{32}H_{28}N_3O_6S_2Cl$)<br>　　　C(%)　H(%)　N(%)　S(%)　Cl(%)<br>Calcd.　59.12　4.34　6.46　9.86　5.45<br>Found　58.84　4.28　6.38　9.82　5.50 |

TABLE 28

| Example No. | X | —A— | Binding position | R' | D | R⁴ | Melting point(° C.) | Physicochemical property |
|---|---|---|---|---|---|---|---|---|
| 101 | S | —CH₂O— | 3 | H | CH₂ | CN | 105–107 | Elemental analysis ($C_{32}H_{26}N_3O_5S_2Cl_2$)<br>　　　C (%)　H (%)　N (%)　S (%)　Cl (%)<br>Calcd.　60.80　4.15　6.65　10.14　5.61<br>Found　60.83　4.08　6.68　10.15　5.74 |
| 102 | S | —CH₂S— | 3 | H | CH₂ | COOC₂H₅ | — | MS: (m/z) 695 (M⁺)<br>NMR (CDCl₃)<br>δ: 1.26 (3H, t, J=7.3Hz), 1.99–2.06 (2H, m), 2.69 (2H, t, J=7.3Hz), 3.06–3.10(2H, m), 4.25 (2H, q, J=7.3Hz), 4.63 (2H, s), 4.67 (2H, s), 6.82 (2H, s), 7.34–7.46 (3H, m), 7.52 (2H, d, J=8.6Hz), 7.56 (1H, br-d, J=7.9Hz), 7.80–7.84 (2H, m), 7.83 (2H, d, J=8.5Hz), 7.95 (1H, br-d, J=7.9Hz), 8.12 (1H, s), 8.26 (1H, s), 9.25 (br-s) |

TABLE 29

[Structure: benzoxazole/benzothiazole-A-phenyl-C(O)NH-phenyl(O-D-R⁴)(CH₂)₃SO₂-C₆H₄-Cl]

| Example No. | X | —A— | Binding position | R' | D | R⁴ | Melting point (° C.) | Physicochemical property |
|---|---|---|---|---|---|---|---|---|
| 103 | S | —CH₂O— | 3 | 6-Cl | CH₂ | COOH | 212 | Elemental analysis ($C_{32}H_{26}N_2O_7S_2Cl_2 \cdot 0.5H_2O$)<br>　　　C(%)　H(%)　N(%)　S(%)　Cl(%)<br>Calcd.　55.33　3.92　4.03　9.23　10.21<br>Found　55.37　3.69　3.98　9.33　10.13<br>Elemental analysis ($C_{33}H_{29}N_2O_6S_2Cl \cdot 0.3H_2O$) |

TABLE 29-continued

| Example No. | X | —A— | Binding position | R' | D | R⁴ | Melting point (° C.) | Physicochemical property | | | | | |
|---|---|---|---|---|---|---|---|---|---|---|---|---|---|
| 104 | S | —CH$_2$CH$_2$— | 3 | H | CH$_2$ | COOH | 176–178 | | C(%) | H(%) | N(%) | S(%) | Cl(%) |
| | | | | | | | | Calcd. | 60.55 | 4.56 | 4.28 | 9.80 | 5.42 |
| | | | | | | | | Found | 60.63 | 4.45 | 4.27 | 9.90 | 5.52 |
| | | | | | | | | MS: (m/z)667(M⁺) | | | | | |
| | | | | | | | | Elemental analysis (C$_{32}$H$_{27}$N$_2$O$_6$S$_3$Cl) | | | | | |
| 105 | S | —CH$_2$S— | 3 | H | CH$_2$ | COOH | 80–82 | | C(%) | H(%) | N(%) | S(%) | Cl(%) |
| | | | | | | | | Calcd. | 57.60 | 4.08 | 4.20 | 14.42 | 5.31 |
| | | | | | | | | Found | 57.43 | 4.05 | 4.20 | 14.14 | 5.09 |
| | | | | | | | | Elemental analysis (C$_{34}$H$_{30}$N$_3$O$_8$S$_2$Cl) | | | | | |
| 106 | S | —CH$_2$O— | 3 | H | CH$_2$ | (CONHCH$_2$COOH group) | 200 | | C(%) | H(%) | N(%) | S(%) | Cl(%) |
| | | | | | | | | Calcd. | 57.66 | 4.27 | 5.93 | 9.06 | 5.01 |
| | | | | | | | | Found | 57.40 | 4.21 | 5.95 | 9.03 | 4.98 |

TABLE 30

| Example No. | Chemical Formula |
|---|---|
| 22 | |
| 33 | |
| 37 | |

TABLE 30-continued

| Example No. | Chemical Formula |
|---|---|
| 38 | |
| 42 | |

TABLE 31

| Example No. | Chemical Formula |
|---|---|
| 43 | |
| 44 | |
| 45 | |

TABLE 31-continued
| Example No. | Chemical Formula |
|---|---|
| 46 | 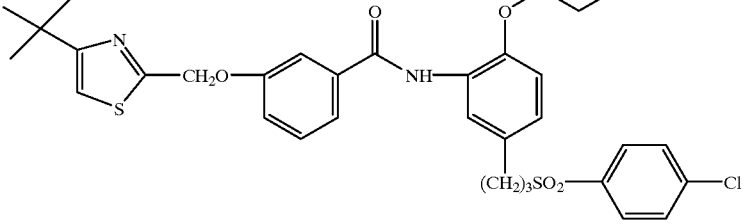 |
| 47 | 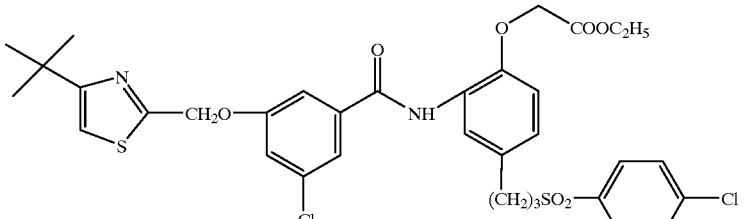 |
TABLE 32
| Example No. | Chemical Formula |
|---|---|
| 48 | 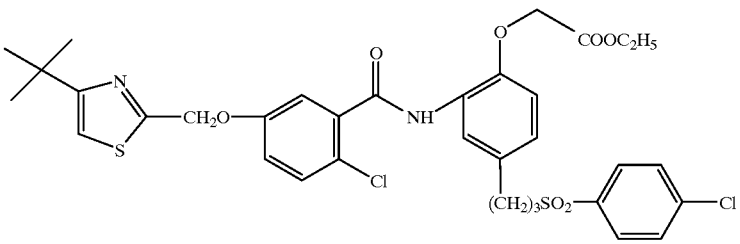 |
| 49 | 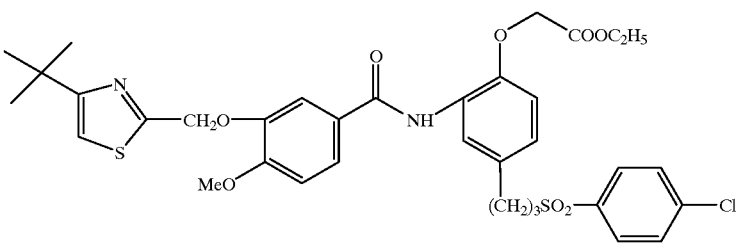 |
| 50 | 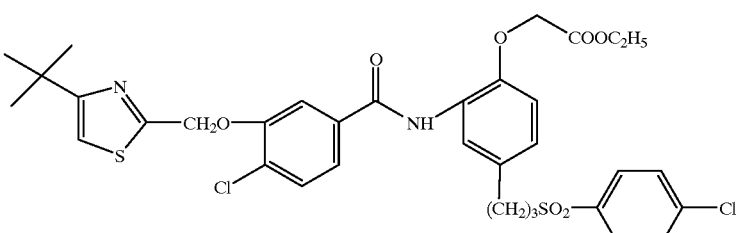 |

TABLE 32-continued

| Example No. | Chemical Formula |
|---|---|
| 51 | |
| 52 | |

TABLE 33

| Example No. | Chemical Formula |
|---|---|
| 53 | |
| 54 | |
| 55 | |

TABLE 33-continued
| Example No. | Chemical Formula |
|---|---|
| 56 | 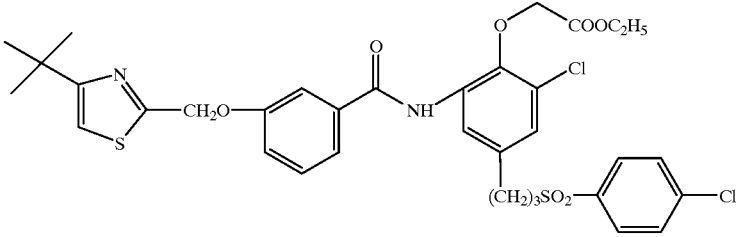 |
| 57 | 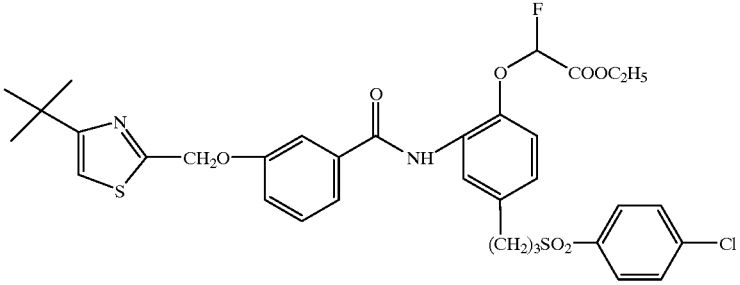 |
TABLE 34
| Example No. | Chemical Formula |
|---|---|
| 58 | 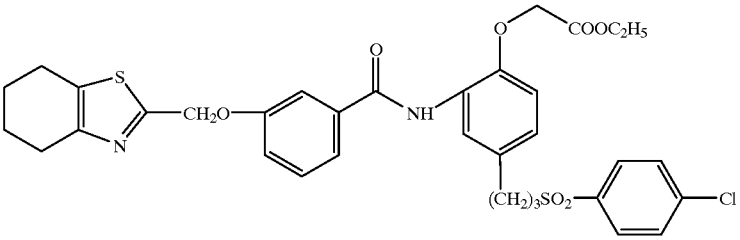 |
| 59 | 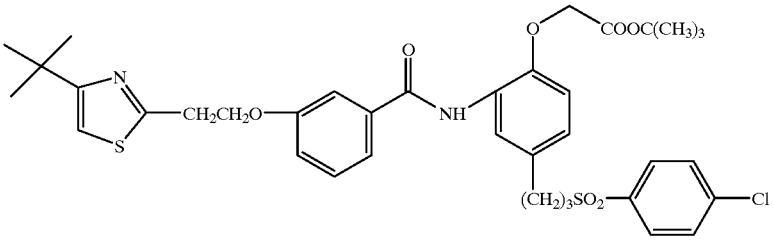 |
| 60 | 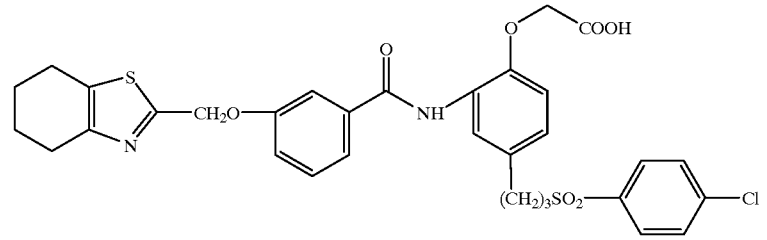 |

TABLE 34-continued

| Example No. | Chemical Formula |
| --- | --- |
| 61 | (4-tert-butylthiazol-2-yl)-CH2O-(5-Cl-phenyl)-C(O)NH-[2-(OCH2COOH)-4-((CH2)3SO2-(4-Cl-phenyl))phenyl] |
| 62 | (4-tert-butylthiazol-2-yl)-CH2O-(2-Cl-phenyl)-C(O)NH-[2-(OCH2COOH)-4-((CH2)3SO2-(4-Cl-phenyl))phenyl] · 0.85H2O |

TABLE 35

| Example No. | Chemical Formula |
| --- | --- |
| 63 | (4-tert-butylthiazol-2-yl)-CH2O-(4-OCH3-phenyl)-C(O)NH-[2-(OCH2COOH)-4-((CH2)3SO2-(4-Cl-phenyl))phenyl] · 0.5H2O |
| 64 | (4-tert-butylthiazol-2-yl)-CH2O-(4-Cl-phenyl)-C(O)NH-[2-(OCH2COOH)-4-((CH2)3SO2-(4-Cl-phenyl))phenyl] |
| 65 | (4-tert-butylthiazol-2-yl)-CH2O-(4-CH3-phenyl)-C(O)NH-[2-(OCH2COOH)-4-((CH2)3SO2-(4-Cl-phenyl))phenyl] · H2O |

TABLE 35-continued
| Example No. | Chemical Formula |
|---|---|
| 66 | 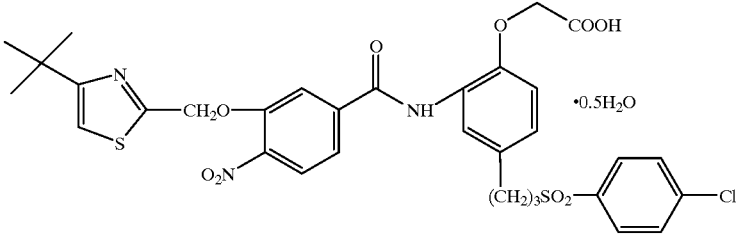 ·0.5H₂O |
| 67 | 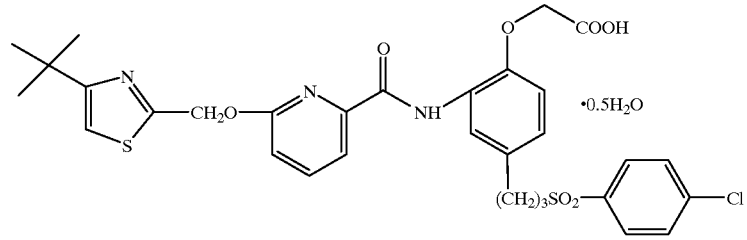 ·0.5H₂O |
TABLE 36
| Example No. | Chemical Formula |
|---|---|
| 68 | 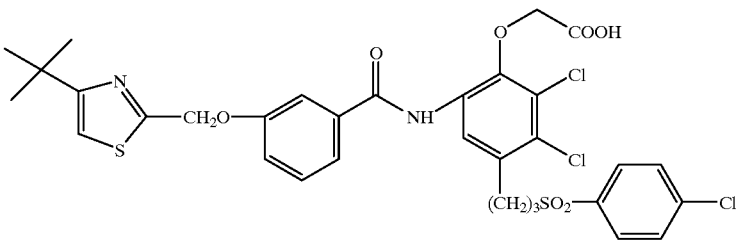 |
| 69 | 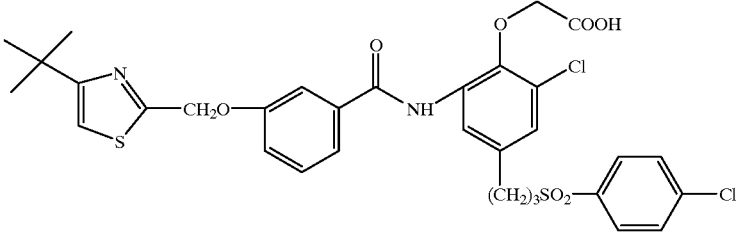 |
| 70 | 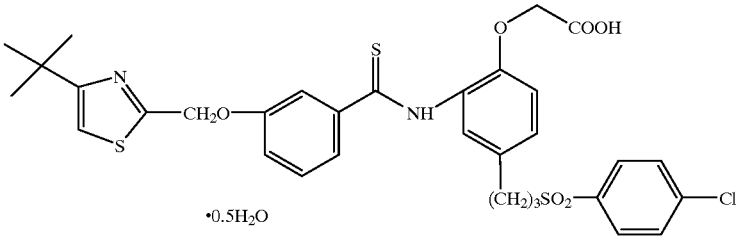 ·0.5H₂O |

TABLE 36-continued

| Example No. | Chemical Formula |
|---|---|
| 71 | |
| 72 | |

TABLE 37

| Example No. | Chemical Formula |
|---|---|
| 73 | |
| 74 | |
| 75 | |

TABLE 37-continued
| Example No. | Chemical Formula |
|---|---|
| 76 | 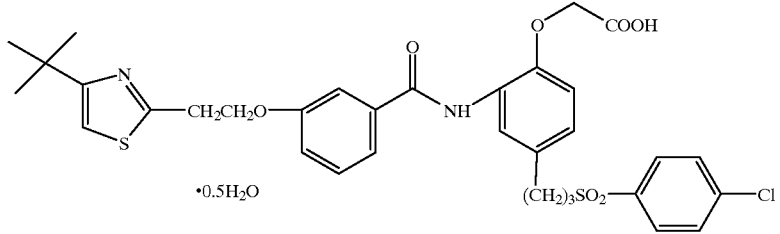 ·0.5H₂O |
| 77 | 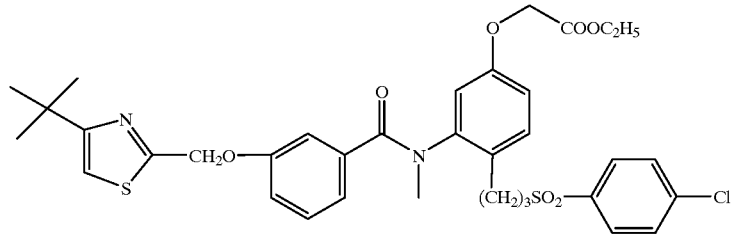 |
TABLE 38
| Example No. | Chemical Formula |
|---|---|
| 78 | 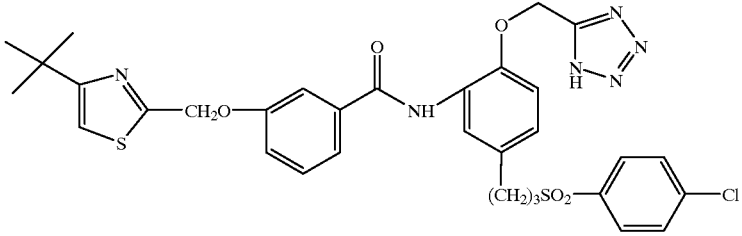 |
| 79 | 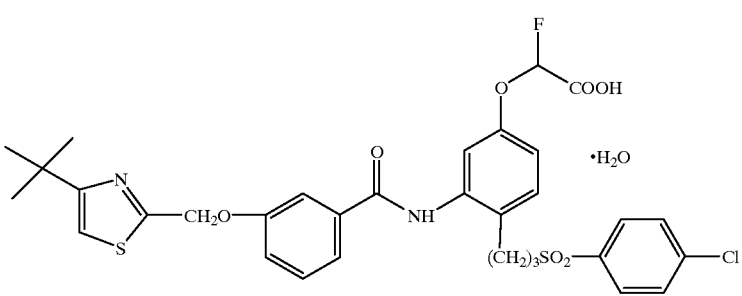 ·H₂O |
| 80 | 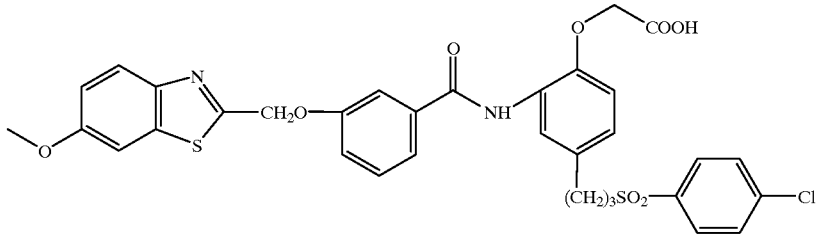 |

TABLE 38-continued
| Example No. | Chemical Formula |
|---|---|
| 107 | 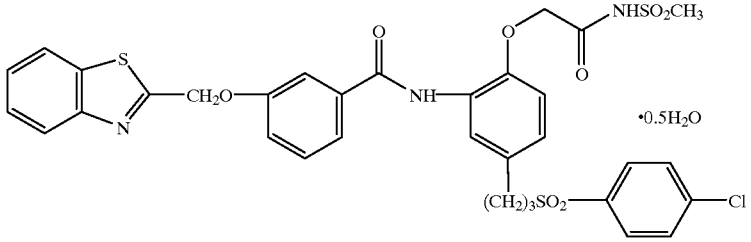 •0.5H₂O |
TABLE 39
| Example No. | Chemical Formula |
|---|---|
| 108 | 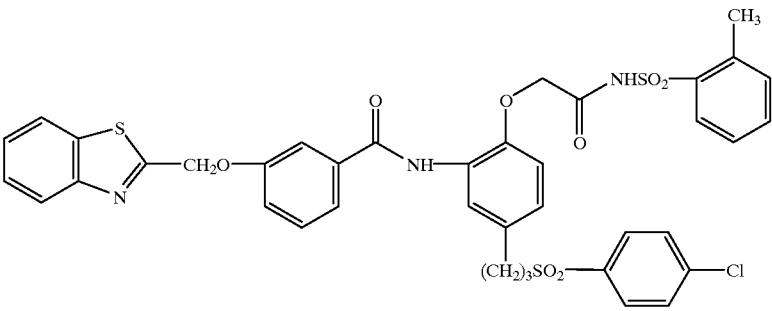 |
| 109 | 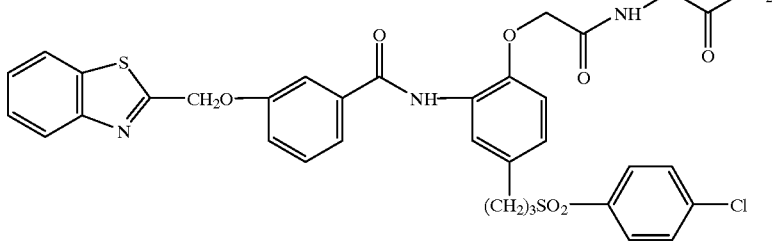 |
| 110 | 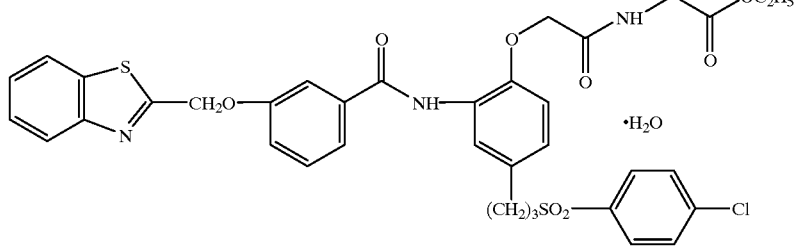 •H₂O |
| 111 | 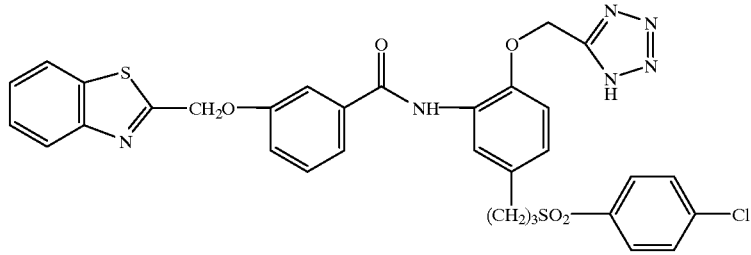 |

We claim:
1. An azole derivative represented by the following general formula (I):

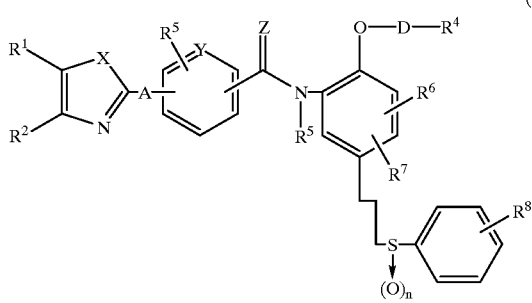

wherein the symbols in the above formula are defined as follows;

R₁ and R²: these may be the same or different from each other and each represents a hydrogen atom, a cycloalkyl group, a lower alkyl group which may be substituted or an aryl group which may be substituted, or R¹ and R² may be combined with a ring

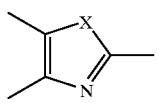

to form a condensed ring represented by a formula

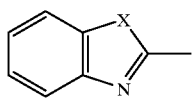

or a formula

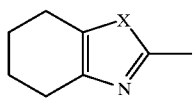

and these condensed rings may be substituted with a lower alkyl group which may be substituted, an amino group, a cyano group, a nitro group, a hydroxyl group, a halogen atom or a lower alkoxy group, R³, R⁶, R⁷ and R⁸: these may be the same or different from one another and each represents a hydrogen atom, an amino group, a cyano group, a nitro group, a hydroxyl group, a halogen atom, a lower alkoxy group or a lower alkyl group which may be substituted, R⁴: a cyano group, a tetrazolyl group, a group represented by a formula —COOR⁹ or a group represented by a formula —E—NH—F—R¹⁰, R⁹: a hydrogen atom or an ester residue, E: a single bond or a carbonyl group, F: a single bond or a lower alkylene group, R¹⁰: a hydrogen atom; a carbamoyl group; a mono- or di-lower alkylcarbamoyl group; a carboxyl group; a lower alkoxycarbonyl group; an arylcarbonyl group which may be substituted with a lower alkyl group; a lower alkanoyl group; a lower alkylsulfonyl group; or an arylsulfonyl group which may be substituted with a lower alkyl group, R⁵: a hydrogen atom or a lower alkyl group, D: a lower alkylene group which may be substituted, X represents a sulfur atom (S) and Z represents an oxygen atom (O) or a sulfur atom (S), Y: a nitrogen atom (—N═) or a methine group (—CH═), A: a group represented by the following formula —O—B—, —B—O—, —S—B—, —B—S— or —B—, B: a lower alkylene group or a lower alkyenylene group, and n: 0, 1 or 2, or a pharmaceutically acceptable salt thereof, a hydrate thereof or a solvate thereof.

2. The azole derivative, a pharmaceutically acceptable salt thereof, a hydrate thereof or a solvate thereof according to claim 1, wherein R⁴ is
1) a tetrazolyl group,
2) a group represented by a formula —COOR⁹ R⁹ where is a hydrogen atom or an ester residue, or
3) a group represented by the formula —E—NH—F—R¹⁰ wherein E is a single bond or a carbonyl group, F is a single bond or a lower alkylene group and R¹⁰ is a hydrogen atom, a carbamoyl group, a carboxyl or a lower alkoxycarbonyl group, a lower alkanoyl group, a lower alkylsulfonyl group or an arylsulfonyl group which may be substituted with a lower alkyl group.

3. The azole derivative, a pharmaceutically acceptable salt thereof, a hydrate thereof or a solvate thereof according to claim 1, wherein Y is methine group (—CH═).

4. The azole derivative, a pharmaceutically acceptable salt thereof, a hydrate thereof or a solvate thereof according to claim 2, wherein R¹ and R² may be the same or different from each other and each represents a hydrogen atom, a cycloalkyl group, a lower alkyl group, a phenyl group which may be substituted with a lower alkyl group, or R¹ and R² may be combined with a ring

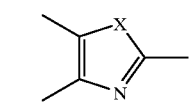

to form a condensed ring represented by a formula

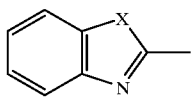

or a formula

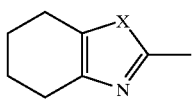

and these condensed rings may be substituted with a lower alkyl group which may be substituted with 1 to 3 halogen atoms, or with an amino group, a cyano group, a nitro group, a hydroxyl group, a halogen atom or a lower alkoxy group, D is a lower alkylene group which may be substituted with a halogen atom, and A is a group represented by a formula —B—O—, a formula —S—B—, a formula —B—S— or a formula —B— wherein B is a lower alkylene group or a lower alkenylene group.

5. The azole derivative or a pharmaceutically acceptable salt thereof according to claim 4, wherein $R^1$ and $R^2$ may be the same or different from each other and each represents a hydrogen atom, a cycloalkyl group, a lower alkyl group or phenyl group which may be substituted with a lower alkyl group, each of $R^3$, $R^6$ and $R^7$ is a hydrogen atom, $R^8$ is a halogen atom, $R^5$ is a hydrogen atom, D is a methylene group, X is a sulfur atom, Y is a methine group (—CH═), Z is an oxygen atom, A is a group represented by the formula —CH$_2$O— and n is 2.

6. 2-[3-(4-tert-Butyl-2-thiazolylmethoxy)benzoylamino]-4-[3-(4-chlorophenylsulfonyl)propyl]phenoxyacetic acid, 4-[3-(4-chlorophenylsulfonyl)propyl]-2-[3-[(4-cyclobutyl-2-thiazolyl)methoxy]benzoylamino]phenoxyacetic acid, 3-[(4-tert-butyl-2-thiazolyl)methoxy]-5'-[3-(4-chlorophenylsulfonyl)propyl]-2'-(1H-tetrazol-5-ylmethoxy)benzanilide, 3-(2-benzothiazolylmethoxy)-5'-[3-(4-chlorophenylsulfonyl)propyl]-2'-(1H-tetrazol-5-ylmethoxy)benzanilide, or a pharmaceutically acceptable salt thereof, a hydrate thereof or a solvate thereof.

7. A pharmaceutical composition which comprises the azole derivative of any one of claims 1,2,4,5,6, or 7 a pharmaceutically acceptable salt thereof, a hydrate thereof or a solvate thereof and a pharmaceutically acceptable carrier.

8. A method of antagonizing leukotriene or thromboxane $A_2$, which comprises administering a therapeutically effective amount of the azole derivative of any one of claims 1,2,3,4,5 or 6, a pharmaceutically acceptable salt thereof, a hydrate thereof or a solvate thereof as the active ingredient to a subject in need of the same.

9. The method according to claim 8, which is a preventive or therapeutic agent of an allergic disease.

10. The method according to claim 9, wherein the allergic disease is bronchial asthma, allergic rhinitis or urticaria.

11. The method according to claim 8, which is a preventive or therapeutic agent of ischemic heart disease or ischemic cerebral disease.

* * * * *